United States Patent
Nuytkens et al.

(10) Patent No.: US 11,890,489 B2
(45) Date of Patent: *Feb. 6, 2024

(54) TREATMENT OF NEUROLOGICAL ABNORMALITIES USING DYNAMIC ELECTROENCEPHALOGRAPHY

(71) Applicant: Diagnostyx, Inc., Middletown, RI (US)

(72) Inventors: Peter R. Nuytkens, Franklin, MA (US); Joseph Kulinets, Laguna Hills, CA (US); Hans J. Weedon, Salem, MA (US); Mark H. Nuytkens, Mystic, CT (US)

(73) Assignee: Diagnostyx, Inc., Middletown, RI (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/824,375

(22) Filed: May 25, 2022

(65) Prior Publication Data

US 2022/0280810 A1 Sep. 8, 2022

Related U.S. Application Data

(63) Continuation of application No. 17/349,332, filed on Jun. 16, 2021, now Pat. No. 11,344,745.

(60) Provisional application No. 63/040,556, filed on Jun. 18, 2020.

(51) Int. Cl.
*A61N 5/06* (2006.01)

(52) U.S. Cl.
CPC ......... *A61N 5/0622* (2013.01); *A61N 5/0618* (2013.01); *A61N 2005/0626* (2013.01); *A61N 2005/0647* (2013.01)

(58) Field of Classification Search
CPC ............... A61N 5/0622; A61N 5/0618; A61N 2005/0626; A61N 2005/0647
See application file for complete search history.

(56) References Cited

U.S. PATENT DOCUMENTS

| | | |
|---|---|---|
| 5,458,117 A | 10/1995 | Chamoun et al. |
| 8,025,687 B2 | 9/2011 | Streeter et al. |
| 8,167,921 B2 | 5/2012 | Streeter et al. |
| 8,303,636 B2 | 11/2012 | Schiffer |
| 8,307,784 B2 | 11/2012 | Nadreau et al. |
| 8,364,271 B2 | 1/2013 | De Ridder |

(Continued)

FOREIGN PATENT DOCUMENTS

| | | |
|---|---|---|
| EP | 3429682 B | 1/2020 |
| WO | 2019053625 A1 | 3/2019 |

OTHER PUBLICATIONS

"Photobiomodulation Helmet," Suyzeko, dated Dec. 10, 2020, 19 pages.

(Continued)

*Primary Examiner* — Jonathan T Kuo
(74) *Attorney, Agent, or Firm* — Sterne, Kessler, Goldstein & Fox P.L.L.C.

(57) ABSTRACT

A method of treating a neurological disorder and/or disease includes positioning a stimulation apparatus on a patient. The stimulation apparatus includes an electrode array having a plurality of electrodes and an emitter array having a plurality of emitters. The method further includes measuring electroencephalography (EEG) signals of the patient with the electrode array. The method further includes emitting radiation into the patient's brain from the emitter array based on the measured EEG signals in order to treat the neurological disorder and/or disease.

26 Claims, 23 Drawing Sheets

(56) References Cited

U.S. PATENT DOCUMENTS

| | | | |
|---|---|---|---|
| 8,574,279 | B2 | 11/2013 | Schiffer |
| 8,790,383 | B2 | 7/2014 | Aunio et al. |
| 8,936,630 | B2 | 1/2015 | Denison et al. |
| 9,238,142 | B2 | 1/2016 | Heldman et al. |
| 9,522,278 | B1 | 12/2016 | Heldman et al. |
| 9,717,920 | B1 | 8/2017 | Heldman et al. |
| 9,795,803 | B2 | 10/2017 | Streeter et al. |
| 9,884,164 | B2 | 2/2018 | Tass |
| 9,956,425 | B2 | 5/2018 | Peyman |
| 10,155,121 | B2 | 12/2018 | Zao et al. |
| 10,178,952 | B2 | 1/2019 | Westermann et al. |
| 10,188,872 | B2 | 1/2019 | De Taboada et al. |
| 10,279,192 | B2 | 5/2019 | Malchano et al. |
| 10,293,177 | B2 | 5/2019 | Malchano et al. |
| 10,307,611 | B2 | 6/2019 | Malchano et al. |
| 10,471,276 | B2 | 11/2019 | Beckner et al. |
| 10,575,783 | B2 | 3/2020 | Oxley |
| 10,660,572 | B2 | 5/2020 | Gunasekar et al. |
| 2003/0181961 | A1 | 9/2003 | Kamei |
| 2010/0016841 | A1 | 1/2010 | De Taboada et al. |
| 2012/0065709 | A1 | 3/2012 | Dunning et al. |
| 2013/0138182 | A1 | 5/2013 | Nissila et al. |
| 2014/0058483 | A1 | 2/2014 | Zao et al. |
| 2016/0008628 | A1 | 1/2016 | Morries et al. |
| 2016/0106950 | A1 | 4/2016 | Vasapollo |
| 2017/0231058 | A1 | 8/2017 | Sadwick |
| 2018/0133431 | A1 | 5/2018 | Malchano et al. |
| 2018/0133504 | A1 | 5/2018 | Malchano et al. |
| 2018/0133507 | A1 | 5/2018 | Malchano et al. |
| 2018/0153470 | A1 | 6/2018 | Gunasekar et al. |
| 2018/0169436 | A1 | 6/2018 | Shanks |
| 2018/0317848 | A1 | 11/2018 | Gunasekar et al. |
| 2018/0333590 | A1 | 11/2018 | Millard et al. |
| 2019/0083785 | A1 | 3/2019 | Tass et al. |
| 2019/0240443 | A1 | 8/2019 | Tsai et al. |
| 2019/0255350 | A1 | 8/2019 | Malchano et al. |
| 2019/0269936 | A1 | 9/2019 | Malchano et al. |
| 2019/0299021 | A1 | 10/2019 | Kamei |
| 2019/0314641 | A1 | 10/2019 | Malchano et al. |
| 2019/0351252 | A1 | 11/2019 | Taboada et al. |
| 2020/0069959 | A1 | 3/2020 | Johnson et al. |
| 2020/0093687 | A1 | 3/2020 | Thomas |
| 2020/0360715 | A1 | 11/2020 | Lim |

OTHER PUBLICATIONS

"Photobiomodulation Brain Helmet," gr8 Solutions, dated Dec. 10, 2020, 6 pages.

Berman et al., "Photobiomodulation with Near Infrared Light Helmet in a Pilot, Placebo Controlled Clinical Trial in Dementia Patients Testing Memory and Cognition," J. Neurol. Neurosci., vol. 8, No. 1:176, dated Feb. 28, 2017, 8 pages.

Michael R. Hamblin, "Photobiomodulation for Alzheimer's Disease: Has the Light Dawned?," Photonics, vol. 6, No. 3, dated Sep. 1, 2019, 27 pages.

Enengl et al., "Photobiomodulation for Alzheimer's Disease: Translating Basic Research to Clinical Application," J. Alzheimer's Dis., vol. 75, No. 4, pp. 1073-1082, dated Jun. 15, 2020, 10 pages.

Blivet et al., "Neuroprotective effect of a new photobiomodulation technique against Aß25-35 peptide-induced toxicity in mice: Novel hypothesis for therapeutic approach of Alzheimer's disease suggested," Alzheimer's & Dementia: Translational Research & Clinical Interventions, vol. 4, No. 1, pp. 54-63, dated Feb. 2018, 10 pages.

International Search Report and Written Opinion of the International Searching Authority for International Application No. PCT/US2021/037412, European Patent Office, Rijswijk, The Netherlands, dated Nov. 26, 2021, 15 pages.

TREATMENT OF NEUROLOGICAL ABNORMALITIES USING DYNAMIC ELECTROENCEPHALOGRAPHY

CROSS REFERENCE TO RELATED APPLICATIONS

This application is a continuation of U.S. application Ser. No. 17/349,332, filed Jun. 16, 2021, which claims priority to U.S. Provisional Application No. 63/040,556, filed Jun. 18, 2020, which are hereby incorporated herein in their entireties by reference.

BACKGROUND

Field

The present disclosure relates to stimulation apparatuses, systems, and methods, for example, dynamic stimulation apparatuses, systems, and methods for treatment of a neurological abnormality.

Background

Neurological abnormalities can cause a loss of cognitive ability that can interfere with a person's daily functions. Neurological abnormalities can include a collection of symptoms caused by a variety of different disorders, diseases, and/or conditions. For example, Alzheimer's disease is a neurodegenerative disease associated with the buildup of plaque, for example, on the surface of the brain.

High-energy laser therapy has been used to surgically cut, cauterize, and/or ablate biological tissue. Low-level or low-power laser therapy has been used for treating different ailments by administering therapeutic light energy at low power to the surface of the body for biostimulation of tissues. Low-level light therapy can be applied to a patient's head to enhance neurological functions by controlling various parameters of the light energy. Light energy can be delivered through the skull of a patient to a target area in the patient's brain to enhance neurologic functioning.

Electroencephalography (EEG) is an electrophysiological monitoring method to observe and record electrical activity of a patient's brain. EEG signals measure the brain's spontaneous electrical activity over a period of time as recorded from multiple electrodes placed on a patient's scalp. EEG signals can reflect electrical activity in different regions of the patient's brain (e.g., neural oscillations) over time in the frequency domain. Neural oscillations or brain waves are rhythmic or repetitive patterns of neural activity. Brain waves have been categorized into five different types based on dominant frequency signatures: delta, theta, alpha, beta, and gamma. Gamma waves are correlated with large scale brain network activity and cognitive phenomena.

Altered gamma activity has been observed in cognitive disorders (e.g., Alzheimer's disease). Synchronization of gamma oscillations via non-invasive stimuli in the gamma frequency band (e.g., about 40 Hz), for example, by flashes of light or pulses of sound can to some degree promote detoxification of the brain and improve neurologic functioning. However, the precise molecular and cellular mechanisms by which gamma band stimulation (e.g., constant 40 Hz frequency) produce any cognitive improvements in certain neurological abnormalities (e.g., Alzheimer's disease) is unknown. Further, gamma band stimulation is a static constant emission therapy (e.g., 40 Hz frequency) that does not take into account physical states of a patient's brain over time.

SUMMARY

Accordingly, there is a need to dynamically monitor physical states of a patient's brain (e.g., via measuring EEG signals) and dynamically stimulate the patient's brain (e.g., via emitting light energy) based on those measured physical states to provide higher efficacy of treatment, enhance neurologic functioning, and/or increase detoxification of the brain with a single stimulation apparatus.

In some embodiments, a method of treating a neurological disorder and/or disease includes positioning a stimulation apparatus on a patient. The stimulation apparatus includes an electrode array having a plurality of electrodes and an emitter array having a plurality of emitters. In some embodiments, the method further includes measuring electroencephalography (EEG) signals of the patient with the electrode array. In some embodiments, the method further includes emitting radiation into the patient's brain from the emitter array based on the measured EEG signals in order to treat the neurological disorder and/or disease.

In some embodiments, the emitting includes emitting a sequence of optical macro pulses, each having a defined shape, based on the measured EEG signals. In some embodiments, each optical macro pulse has an envelope and is composed of a sequence of pulse width modulation (PWM) filling pulses. In some embodiments, the method further includes adjusting a frequency and/or a duty cycle of the sequence of PWM filling pulses in order to reduce heating of the patient's tissues and/or to control a penetration depth of the radiation into the patient's tissues. In some embodiments, the method further includes adjusting a shape of the envelope and a time between sequential envelopes of the optical macro pulses based on the measured EEG signals. In some embodiments, the method further includes adjusting a spatial control of the radiation based on the measured EEG signals. In some embodiments, the radiation includes a spatial moving wave of radiation.

In some embodiments, the method further includes scanning the plurality of electrodes to determine which electrodes contact the patient within a pre-determined threshold. In some embodiments, the pre-determined threshold is based on a resistance value between the patient and the electrode or an amplitude of the measured EEG signals from the electrode.

In some embodiments, the measuring includes measuring a local EEG signal obtained from an electrode in the electrode array. In some embodiments, the measuring includes measuring a global synthesized EEG signal obtained from a combination of local EEG signals obtained from electrodes in the electrode array. In some embodiments, the method further includes filtering the global synthesized EEG signal in a pre-determined frequency range and/or by a specific signal processing algorithm.

In some embodiments, the method further includes determining an awake-sleep cycle of the patient based on the measured EEG signals. In some embodiments, the method further includes adjusting a pulse shape of the radiation based on the determined awake-sleep cycle in an awake configuration. In some embodiments, the method further includes adjusting a pulse shape of the radiation based on the determined awake-sleep cycle in a sleep configuration.

In some embodiments, the method further includes measuring a patient's tremors, pulse, temperature, oxygen saturation ($SpO_2$), or a combination thereof, with a sensor affixed to the patient.

In some embodiments, the neurological disorder and/or disease includes amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

In some embodiments, the method further includes determining peak brain wave frequencies of the patient with a control unit coupled to the stimulation apparatus based on the measured EEG signals. In some embodiments, the determining includes utilizing an active dynamic feedback loop between measured signals of the stimulation apparatus and stimulation signals of the control unit. In some embodiments, the method further includes operating the active dynamic feedback loop in real time. In some embodiments, the determining peak brain wave frequencies of the patient is based on a fast Fourier transform (FFT) of the measured EEG signals.

In some embodiments, the emitting includes inducing photobiomodulation in the patient's brain to treat the neurological disorder and/or disease.

In some embodiments, the measuring includes individually taking measurements of each electrode in the electrode array. In some embodiments, the emitting includes individually controlling each emitter in the emitter array.

In some embodiments, the emitting includes uniform emission for all emitters in the emitter array. In some embodiments, the emitting includes static emission based on different emissions from different emitters in the emitter array. In some embodiments, the different emissions are based on different optical macro pulses emitted from different areas of the emitter array.

In some embodiments, the emitting includes dynamic emission based on spatial patterns changing in time and dynamically applied to individual emitters. In some embodiments, a frequency of the emitters in the emitter array is the same.

In some embodiments, the patient is a human.

In some embodiments, a system for treatment of a neurological disorder and/or disease includes a stimulation apparatus having an electrode array configured to dynamically measure electroencephalography (EEG) signals of a patient and an emitter array configured to dynamically emit radiation based on the measured EEG signals for treatment of the neurological disorder and/or disease. In some embodiments, the system further includes a control unit coupled to the stimulation apparatus and configured to control the emitter array based on the measured EEG signals.

In some embodiments, the emitted radiation is composed of a sequence of optical macro pulses, each having a defined shape, based on the measured EEG signals. In some embodiments, each optical macro pulse is composed of a sequence of pulse width modulation (PWM) filling pulses. In some embodiments, the control unit adjusts a frequency and/or a duty cycle of the sequence of PWM filling pulses to reduce heating of the patient's tissues and/or to control a penetration depth of the radiation into the patient's tissues. In some embodiments, each optical macro pulse has an envelope and the control unit adjusts a shape of the envelope and a time between sequential envelopes of the optical macro pulses based on the measured EEG signals. In some embodiments, the shape of the envelope includes a rectangular shape, a triangular shape, a Gaussian shape, an exponential shape, a raised cosine-based shape, or a combination thereof. In some embodiments, the control unit includes a spatial wave controller coupled to the emitter array and configured to generate radiation as a spatial moving wave of radiation based on the measured EEG signals.

In some embodiments, an electrode in the electrode array has a conical shape having a plurality of sub-electrodes.

In some embodiments, the EEG signals are based on local EEG signals obtained from electrodes in the electrode array. In some embodiments, the EEG signals are based on a global synthesized EEG signal obtained from a combination of local EEG signals obtained from electrodes in the electrode array. In some embodiments, the global synthesized EEG signal is filtered in a pre-determined frequency range and/or by a specific signal processing algorithm.

In some embodiments, the system further includes an active dynamic feedback loop between measured signals of the stimulation apparatus and stimulation signals of the control unit. In some embodiments, the active dynamic feedback loop operates in real time.

In some embodiments, the control unit is configured to determine peak brain wave frequencies of the patient based on the measured EEG signals. In some embodiments, the peak brain wave frequencies of the patient are determined based on a fast Fourier transform (FFT) of the measured EEG signals.

In some embodiments, the control unit includes a circadian rhythm detector configured to determine an awake-sleep cycle of the patient based on the measured EEG signals. In some embodiments, in an awake configuration, the control unit adjusts the shape of the sequence of optical macro pulses based on the determined awake-sleep cycle. In some embodiments, in a sleep configuration, the control unit adjusts the shape of the sequence of optical macro pulses based on the determined awake-sleep cycle.

In some embodiments, the neurological disorder and/or disease includes amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

In some embodiments, the stimulation apparatus includes a headpiece affixed to the patient's head, and the EEG signals comprise transcranial EEG signals. In some embodiments, the stimulation apparatus further includes a second electrode array configured to dynamically measure second transcranial EEG signals of the patient and a second emitter array configured to dynamically emit second radiation based on the measured second transcranial EEG signals for treatment of the neurological disorder and/or disease. In some embodiments, a frequency range of radiation emitted by the second emitter array is different than a frequency range of radiation emitted by the emitter array.

In some embodiments, the stimulation apparatus further includes an eyepiece affixed to the patient's eye and having a third emitter array configured to dynamically emit warm white light radiation based on the measured transcranial EEG signals.

In some embodiments, the stimulation apparatus further includes an earpiece affixed to the patient's ear and having an acoustic emitter array configured to dynamically emit acoustic radiation based on the measured transcranial EEG signals.

In some embodiments, the stimulation apparatus further includes a nosepiece affixed to the patient's nose and having a fourth emitter array configured to dynamically emit fourth radiation based on the measured transcranial EEG signals.

In some embodiments, the system further includes a sensor coupled to the control unit and affixed to the patient. In some embodiments, the sensor includes a tremor sensor, an accelerometer, a pulse sensor, a temperature sensor, an oxygen saturation ($SpO_2$) sensor, or a combination thereof.

Implementations of any of the techniques described above can include a system, a method, a process, a device, and/or an apparatus. The details of one or more implementations are set forth in the accompanying drawings and the description below. Other features will be apparent from the description and drawings, and from the claims.

Further features and exemplary aspects of the embodiments, as well as the structure and operation of various embodiments, are described in detail below with reference to the accompanying drawings. It is noted that the embodiments are not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the embodiments and, together with the description, further serve to explain the principles of the embodiments and to enable a person skilled in the relevant art(s) to make and use the embodiments.

Figure 1:
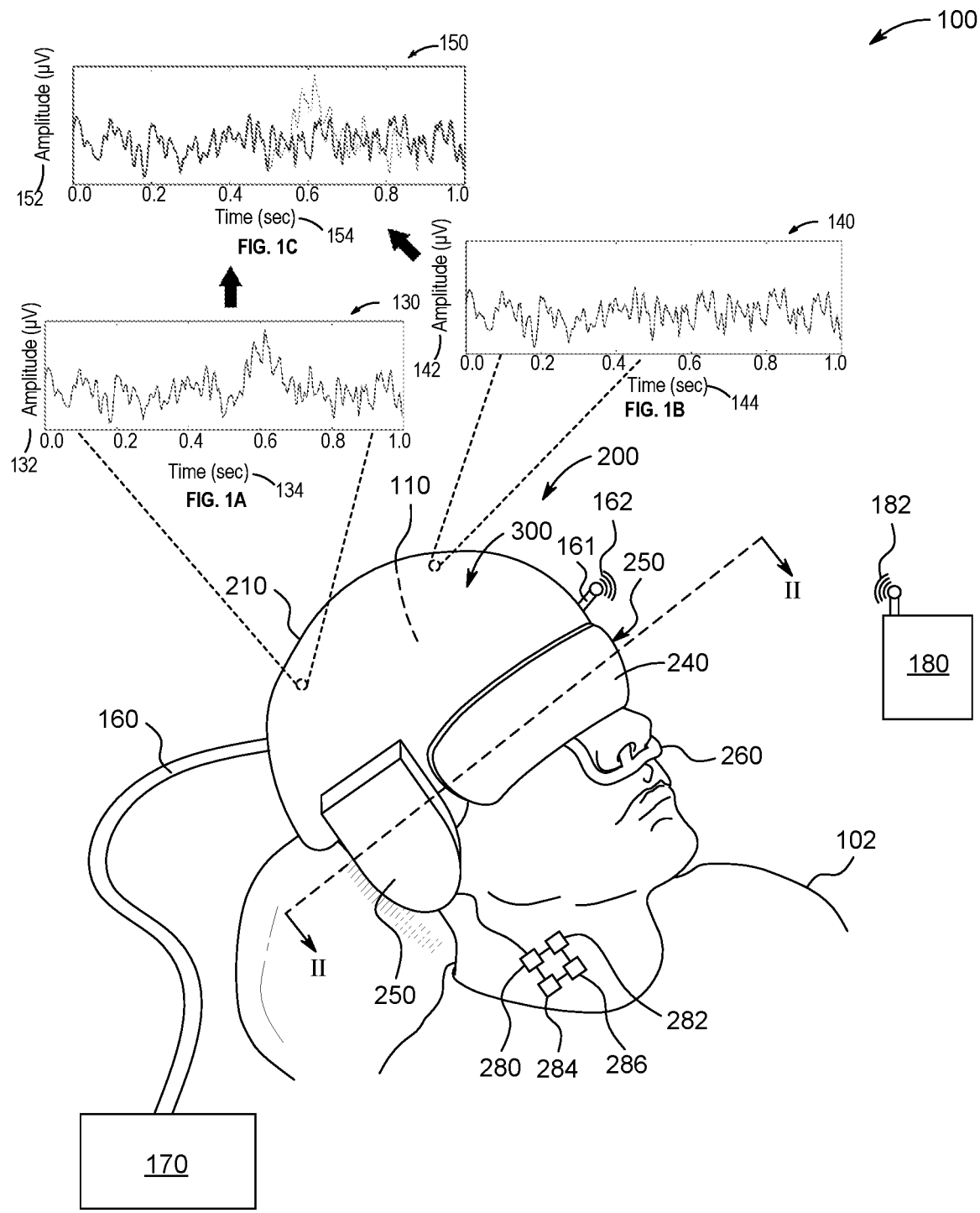
FIG. 1 is a schematic perspective illustration of a stimulation system with a stimulation apparatus, according to an exemplary embodiment.

The features and exemplary aspects of the embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. Additionally, generally, the left-most digit(s) of a reference number identifies the drawing in which the reference number first appears. Unless otherwise indicated, the drawings provided throughout the disclosure should not be interpreted as to-scale drawings.

DETAILED DESCRIPTION

This specification discloses one or more embodiments that incorporate the features of this present invention. The disclosed embodiment(s) merely exemplify the present invention. The scope of the invention is not limited to the disclosed embodiment(s). The present invention is defined by the claims appended hereto.

The embodiment(s) described, and references in the specification to "one embodiment," "an embodiment," "an example embodiment," "an exemplary embodiment," etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Spatially relative terms, such as "beneath," "below," "lower," "above," "on," "upper" and the like, can be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus can be otherwise oriented (rotated 90 degrees or at other orientations) and the spatially relative descriptors used herein can likewise be interpreted accordingly.

The term "about" or "substantially" or "approximately" as used herein indicates the value of a given quantity that can vary based on a particular technology. Based on the particular technology, the term "about" or "substantially" or "approximately" can indicate a value of a given quantity that varies within, for example, 1-15% of the value (e.g., ±1%, ±2%, ±5%, ±10%, or ±15% of the value).

The term "EEG" stands for electroencephalography or an electroencephalogram that is an electrophysiological monitoring method or output that observes and records electrical activity of a patient's brain. For example, EEG signals can be measured locally (e.g., individually) or combined to form a global synthesized EEG signal.

The term "PWM" stands for pulsed width modulation that can control an average power and/or peak power delivered from a signal by discretizing the signal into a series of pulses. For example, an EEG signal can be discretized into a series of rectangular pulse waves or a dynamic light emitter waveform can be formed from a series of rectangular pulse waves.

The term "pre-determined range" stands for a threshold value calculated prior to administration of the stimulation system. For example, a maximum surface temperature of a patient's scalp for safe application of light energy therapy can be calculated (e.g., about 104° F. to about 110° F.) and implemented as a threshold value not to be exceeded (e.g., not to exceed 106° F.).

The term "awake-sleep cycle" stands for a cycle within the circadian rhythm of a patient which is based on the patient's 24 hour biological clock.

The term "SpO$_2$" stands for oxygen saturation that represents the percentage of hemoglobin (e.g., oxygen transport in red blood cells) binding sites in a patient's bloodstream occupied by oxygen. For example, SpO$_2$ can be measured by calculating the fraction of oxygen saturated hemoglobin relative to the total hemoglobin (e.g., unsaturated plus saturated) in a patient's blood.

The term "neurological disorder" or "neurological disease" stands for a type of neurological abnormality. For example, amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

The term "FFT" stands for fast Fourier transform that is an algorithm to convert a signal from an original domain (e.g., time, space, etc.) to a representation in the frequency domain. For example, an EEG signal measured over time can be converted to frequencies as a discrete Fourier transform of the EEG signal.

The term "photobiomodulation" stands for a form of light therapy that utilizes low-level non-ionizing light sources to stimulate photochemical changes within cellular structures that are receptive to photons. For example, light energy can be applied to a patient's head, ear, eye, and/or nose and be absorbed by cells (e.g., by mitochondria within the cell) that can accept photonic energy of certain wavelengths.

The term "uniform emission" stands for emission that is isotropic or evenly distributed by all emitters. For example, each emitter in an emitter array can emit radiation of the same intensity, power, frequency, and/or wavelength.

The term "static emission" stands for emission that is anisotropic and does not change over time. For example, different emitters in an emitter array can emit different radiation (e.g., different intensity, power, frequency, and/or wavelength) but not change over time so that the emission remains static (e.g., unchanging).

The term "dynamic emission" stands for emission that can be isotropic or anisotropic and does change over time. For example, different emitters in an emitter array can emit different radiation (e.g., different intensity, power, frequency, and/or wavelength) and change over time so that the emission is dynamic (e.g., changing).

The term "real time" stands for operations or processes that respond to inputs reliably within a specified time interval. For example, a frame rate of 2.56 seconds or less can be considered to operate in real time.

Numerical values, including endpoints of ranges, can be expressed herein as approximations preceded by the term "about," "substantially," "approximately," or the like. In such cases, other embodiments include the particular numerical values. Regardless of whether a numerical value is expressed as an approximation, two embodiments are included in this disclose: one expressed as an approximation, and another not expressed as an approximation. It will be further understood that an endpoint of each range is significant both in relation to another endpoint, and independently of another endpoint.

Embodiments of the disclosure can be implemented in hardware, firmware, software, or any combination thereof. Embodiments of the disclosure can also be implemented as instructions stored on a machine-readable medium, which can be read and executed by one or more processors. A machine-readable medium can include any mechanism for storing or transmitting information in a form readable by a machine (e.g., a computing device). For example, a machine-readable medium can include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, and/or instructions can be described herein as performing certain actions. However, it should be appreciated that such descriptions are merely for convenience and that such actions in fact result from computing devices, processors, controllers, or other devices executing the firmware, software, routines, instructions, etc.

Aspect 1 of the description—A method of treating a neurological disorder and/or disease includes positioning a stimulation apparatus on a patient, the stimulation apparatus includes an electrode array having a plurality of electrodes and an emitter array having a plurality of emitters; measuring electroencephalography (EEG) signals of the patient with the electrode array; and emitting radiation into the patient's brain from the emitter array based on the measured EEG signals in order to treat the neurological disorder and/or disease.

Aspect 2 of the description—The method of aspect 1, wherein the emitting includes emitting a sequence of optical macro pulses, each having a defined shape, based on the measured EEG signals.

Aspect 3 of the description—The method of aspect 2, wherein each optical macro pulse has an envelope and is composed of a sequence of pulse width modulation (PWM) filling pulses.

Aspect 4 of the description—The method of aspect 3, further includes adjusting a frequency and/or a duty cycle of the sequence of PWM filling pulses in order to reduce heating of the patient's tissues and/or to control a penetration depth of the radiation into the patient's tissues.

Aspect 5 of the description—The method of aspect 3, further includes adjusting a shape of the envelope and a time between sequential envelopes of the optical macro pulses based on the measured EEG signals.

Aspect 6 of the description—The method of aspect 3, further includes adjusting a spatial control of the radiation based on the measured EEG signals, wherein the radiation includes a spatial moving wave of radiation.

Aspect 7 of the description—The method of any one of aspects 1-6, further includes scanning the plurality of electrodes to determine which electrodes contact the patient within a pre-determined threshold.

Aspect 8 of the description—The method of aspect 7, wherein the pre-determined threshold is based on a resistance value between the patient and the electrode or an amplitude of the measured EEG signals from the electrode.

Aspect 9 of the description—The method of any one of aspects 1-8, wherein the measuring includes measuring a local EEG signal obtained from an electrode in the electrode array.

Aspect 10 of the description—The method of any one of aspects 1-9, wherein the measuring includes measuring a global synthesized EEG signal obtained from a combination of local EEG signals obtained from electrodes in the electrode array.

Aspect 11 of the description—The method of aspect 10, further includes filtering the global synthesized EEG signal in a pre-determined frequency range and/or by a specific signal processing algorithm.

Aspect 12 of the description—The method of any one of aspects 1-11, further includes determining an awake-sleep cycle of the patient based on the measured EEG signals.

Aspect 13 of the description—The method of aspect 12, further includes adjusting a pulse shape of the radiation based on the determined awake-sleep cycle in an awake configuration.

Aspect 14 of the description—The method of aspect 12, further includes adjusting a pulse shape of the radiation based on the determined awake-sleep cycle in a sleep configuration.

Aspect 15 of the description—The method of any one of aspects 1-14, further includes measuring a patient's tremors, pulse, temperature, oxygen saturation ($SpO_2$), or a combination thereof, with a sensor affixed to the patient.

Aspect 16 of the description—The method of any one of aspects 1-15, wherein the neurological disorder and/or disease includes amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

Aspect 17 of the description—The method of any one of aspects 1-16, further includes determining peak brain wave frequencies of the patient with a control unit coupled to the stimulation apparatus based on the measured EEG signals.

Aspect 18 of the description—The method of aspect 17, wherein the determining includes utilizing an active dynamic feedback loop between measured signals of the stimulation apparatus and stimulation signals of the control unit.

Aspect 19 of the description—The method of aspect 18, further includes operating the active dynamic feedback loop in real time.

Aspect 20 of the description—The method of aspect 17, wherein the determining peak brain wave frequencies of the patient is based on a fast Fourier transform (FFT) of the measured EEG signals.

Aspect 21 of the description—The method of aspect 1, wherein the emitting includes inducing photobiomodulation in the patient's brain to treat the neurological disorder and/or disease.

Aspect 22 of the description—The method of aspect 1, wherein the measuring includes individually taking measurements of each electrode in the electrode array.

Aspect 23 of the description—The method of aspect 1, wherein the emitting includes individually controlling each emitter in the emitter array.

Aspect 24 of the description—The method of aspect 1, wherein the emitting includes uniform emission for all emitters in the emitter array.

Aspect 25 of the description—The method of aspect 1, wherein the emitting includes static emission based on different emissions from different emitters in the emitter array.

Aspect 26 of the description—The method of aspect 25, wherein the different emissions are based on different optical macro pulses emitted from different areas of the emitter array.

Aspect 27 of the description—The method of aspect 1, wherein the emitting includes dynamic emission based on spatial patterns changing in time and dynamically applied to individual emitters.

Aspect 28 of the description—The method of aspect 27, wherein a frequency of the emitters in the emitter array is the same.

Aspect 29 of the description—The method of aspect 1, wherein the patient is a human.

Aspect 30 of the description—A system for treatment of a neurological disorder and/or disease includes a stimulation apparatus having an electrode array configured to dynamically measure electroencephalography (EEG) signals of a patient and an emitter array configured to dynamically emit radiation based on the measured EEG signals for treatment of the neurological disorder and/or disease; and a control unit coupled to the stimulation apparatus and configured to control the emitter array based on the measured EEG signals.

Aspect 31 of the description—The system of aspect 30, wherein the emitted radiation is composed of a sequence of optical macro pulses, each having a defined shape, based on the measured EEG signals.

Aspect 32 of the description—The system of aspect 31, wherein each optical macro pulse is composed of a sequence of pulse width modulation (PWM) filling pulses.

Aspect 33 of the description—The system of aspect 32, wherein the control unit adjusts a frequency and/or a duty cycle of the sequence of PWM filling pulses to reduce heating of the patient's tissues and/or to control a penetration depth of the radiation into the patient's tissues.

Aspect 34 of the description—The system of any one of aspects 31-33, wherein each optical macro pulse has an envelope and the control unit adjusts a shape of the envelope and a time between sequential envelopes of the optical macro pulses based on the measured EEG signals.

Aspect 35 of the description—The system of aspect 34, wherein the shape of the envelope includes a rectangular shape, a triangular shape, a Gaussian shape, an exponential shape, a raised cosine-based shape, or a combination thereof.

Aspect 36 of the description—The system of any one of aspects 30-35, wherein the control unit includes a spatial wave controller coupled to the emitter array and configured to generate radiation as a spatial moving wave of radiation based on the measured EEG signals.

Aspect 37 of the description—The system of any one of aspects 30-36, wherein an electrode in the electrode array has a conical shape having a plurality of sub-electrodes.

Aspect 38 of the description—The system of any one of aspects 30-37, wherein the EEG signals are based on local EEG signals obtained from electrodes in the electrode array.

Aspect 39 of the description—The system of any one of aspects 30-38, wherein the EEG signals are based on a global synthesized EEG signal obtained from a combination of local EEG signals obtained from electrodes in the electrode array.

Aspect 40 of the description—The system of aspect 39, wherein the global synthesized EEG signal is filtered in a pre-determined frequency range and/or by a specific signal processing algorithm.

Aspect 41 of the description—The system of any one of aspects 30-40, further includes an active dynamic feedback loop between measured signals of the stimulation apparatus and stimulation signals of the control unit.

Aspect 42 of the description—The system of aspect 41, wherein the active dynamic feedback loop operates in real time.

Aspect 43 of the description—The system of any one of aspects 30-42, wherein the control unit is configured to determine peak brain wave frequencies of the patient based on the measured EEG signals.

Aspect 44 of the description—The system of aspect 43, wherein the peak brain wave frequencies of the patient are determined based on a fast Fourier transform (FFT) of the measured EEG signals.

Aspect 45 of the description—The system of any one of aspects 30-44, wherein the control unit includes a circadian rhythm detector configured to determine an awake-sleep cycle of the patient based on the measured EEG signals.

Aspect 46 of the description—The system of aspect 45, wherein, in an awake configuration, the control unit adjusts the shape of the sequence of optical macro pulses based on the determined awake-sleep cycle.

Aspect 47 of the description—The system of aspect 45, wherein, in a sleep configuration, the control unit adjusts the shape of the sequence of optical macro pulses based on the determined awake-sleep cycle.

Aspect 48 of the description—The system of any one of aspects 30-47, wherein the neurological disorder and/or disease includes amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

Aspect 49 of the description—The system of any one of aspects 30-48, wherein the stimulation apparatus includes a headpiece affixed to the patient's head, and the EEG signals include transcranial EEG signals.

Aspect 50 of the description—The system of aspect 49, wherein the stimulation apparatus further includes a second electrode array configured to dynamically measure second transcranial EEG signals of the patient; and a second emitter array configured to dynamically emit second radiation based on the measured second transcranial EEG signals for treatment of the neurological disorder and/or disease.

Aspect 51 of the description—They system of aspect 50, wherein a frequency range of radiation emitted by the second emitter array is different than a frequency range of radiation emitted by the emitter array.

Aspect 52 of the description—The system of any one of aspects 49-51, wherein the stimulation apparatus further includes an eyepiece affixed to the patient's eye and having a third emitter array configured to dynamically emit warm white light radiation based on the measured transcranial EEG signals.

Aspect 53 of the description—The system of any one of aspects 49-52, wherein the stimulation apparatus further includes an earpiece affixed to the patient's ear and having an acoustic emitter array configured to dynamically emit acoustic radiation based on the measured transcranial EEG signals.

Aspect 54 of the description—The system of any one of aspects 49-53, wherein the stimulation apparatus further includes a nosepiece affixed to the patient's nose and having a fourth emitter array configured to dynamically emit fourth radiation based on the measured transcranial EEG signals.

Aspect 55 of the description—The system of any one of aspects 30-54, further includes a sensor coupled to the control unit and affixed to the patient, wherein the sensor includes a tremor sensor, an accelerometer, a pulse sensor, a temperature sensor, an oxygen saturation ($SpO_2$) sensor, or a combination thereof.

In some embodiments, dynamically monitoring a physical state of the brain (e.g., via measuring dynamic EEG signals) can provide higher efficacy of treatment, enhancement of neurologic functioning, and increase detoxification of the brain (e.g., reducing plaque, amyloid aggregates, etc.). For example, an active dynamic feedback loop, as compared to an open loop feedback system (e.g., constant 40 Hz sinusoidal waveform), can improve efficacy by monitoring dynamic EEG signals (e.g., in real time).

In some embodiments, independent electrodes can be used to individually detect signals in one or more areas of the brain. For example, one or more local EEG signals can be measured by respective individually controlled electrodes (e.g., as part of a transcranial electrode array). In some embodiments, a global EEG signal can be measured and calculated by combining two or more local EEG signals (e.g., via a heuristic model). In some embodiments, measured EEG signals can be modulated or altered to generate specific waveforms. For example, an amplitude of an EEG waveform can be increased to account for a specific frequency of the brain (e.g., active photobiomodulation absorption frequency). In some embodiments, multiple signals can be taken from different clusters or areas of an electrode array (e.g., a transcranial electrode array). For example, different EEG signals can be detected in different areas of the patient's brain (e.g., multiple local EEG signals).

In some embodiments, EEG signals can be converted over time to frequencies by a fast Fourier transform (FFT). A FFT is an algorithm that converts a signal from a domain (e.g., time or space) to a representation in the frequency domain to generate a discrete Fourier transform of a sequence. For example, a FFT of EEG signals can be calculated and a peak frequency can be determined in different frequency ranges (e.g., 10 Hz, 100 Hz, 1 kHz). In some embodiments, a moving average of FFT frequencies, based on measured EEG signals, can be computed to generate a peak frequency of a patient's brain. For example, the peak frequency can be outputted to an oscillator (e.g., a voltage controlled oscillator (VCO), a numerically controlled oscillator (NCO), etc.) coupled to an emitter array to synchronize the detected EEG signals to the emitter array for dynamic radiation therapy (e.g., dynamic light emission therapy).

In some embodiments, independent emitters with individual drivers (e.g., LED drivers) can be used to individually apply therapy (e.g., light pulse, acoustic pulses) in one or more areas of the brain. For example, individually applied light pulses from independent light emitters can be based on individually detected EEG signals in one or more areas of the brain. In some embodiments, a floating (e.g., dynamic) frequency of a measured EEG signal can be determined. For example, one or more emitters can match and be synchronized with the determined floating frequency. In some embodiments, individually controlled light emitters can be synchronized and combined to generate a dynamic spatial wave (e.g., a moving light wave) over a patient's brain. For example, optical surface waves can be utilized to increase mitochondria activity in the patient's brain. In some embodiments, emitters can be configured in a master-slave relationship so that individual emitters (e.g., active "master") can control one or more other emitters (e.g., passive "slave"). In some embodiments, multiple emitters can be applied from different clusters or areas of an emitter array (e.g., a transcranial light emitter array). For example, different light emitters can be applied in different areas of the patient's brain (e.g., local light emitter therapy).

In some embodiments, a light emitter array of independent light emitters can generate light energy (e.g., photons) based on measured EEG signals to interact with a neuron in a variety of different ways. For example, a light emitter can include bandgap engineering to produce a specific wavelength, frequency, intensity, power density, and/or impulse for stimulation of the brain. In some embodiments, emitters can generate pulsed therapy using pulsed width modulation (PWM). PWM is a method to control an average power delivered by a signal by discretizing the signal into a series of pulses (e.g., rectangular pulse waves). For example, PWM energy can be adjusted or controlled based on one or more parameters (e.g., measured EEG signals, frequency, duty cycle, etc.). In some embodiments, independent light emitters can have different irradiation parameters. For example, each independent light emitter can have a different wavelength (nm), frequency (Hz), power (W), beam area ($cm^2$), and/or pulse waveform structure. In some embodiments, a control unit can control independent emitters for different dose parameters. For example, the control unit can control the energy (J), energy density ($J/cm^2$), irradiation time (s), and/or irradiation area ($cm^2$) of independent light emitters.

In some embodiments, a penetration depth into the patient's brain can be changed by adjusting a duty cycle of the PWM energy pulses. A duty cycle is the fraction of one period in which a signal is active (e.g., 50% duty cycle). Penetration depth roughly follows a linear relationship with the duty cycle since the duty cycle is proportional to the average power over the peak power (e.g., as the duty cycle increases, the average power increases). For example, a high duty cycle (e.g., 80% duty cycle) can produce a deep penetration depth (e.g., about 40 mm) while a low duty cycle (e.g., 20% duty cycle) can produce a shallow penetration depth (e.g., about 10 mm). The frequency of the PWM energy pulses can also adjust the penetration depth. For example, a high frequency (e.g., 100 kHz, 50% duty cycle) can produce a shallow penetration depth (e.g., about 10 mm) while a low frequency (e.g., 100 Hz, 50% duty cycle) can produce a deep penetration depth (e.g., about 40 mm). In some embodiments, PWM energy can control a power density and/or an impulse of the energy to avoid overheating of a patient's scalp. For example, a duty cycle of light energy pulses (e.g., using a constant frequency of 40 Hz) can be adjusted for a deeper penetration depth without exceeding a pre-determined threshold (e.g., surface temperature of 106° F.) on the scalp. In some embodiments, a three-dimensional depth profile can be calculated (e.g., using a volumetric algorithm) to model the light pulse energy penetration depth into a patient's brain.

In some embodiments, an envelope of an EEG signal can be measured. For example, the envelope of the EEG signal can be completely mapped by conducting a frequency sweep (e.g., 20-100 Hz). In some embodiments, a magnitude of an envelope of an EEG signal can be monitored based on a FFT frequency of the EEG signal. For example, the FFT frequency can be based on a local EEG signal and/or a global EEG signal. In some embodiments, an envelope of an EEG signal can be followed by one or more emitters. For example, a FFT frequency of the envelope can be measured and applied to light emitters to follow the envelope shape of the EEG signal. In some embodiments, a time between pulse envelopes of light emitters can be determined by an algorithm based on an FFT of the EEG signal (e.g., within ±40 Hz). In some embodiments, an entire EEG signal can be integrated continuously to provide a closer approximation to the natural EEG frequency of a patient's brain. For example, a control unit (e.g., using a FFT unit) can integrate the measured EEG signal at the start of a pulse envelope of light emitters and continue to integrate until the end of that envelope.

In some embodiments, low-level light therapies can be combined to enhance cell and neurological functions in the brain. For example, transcranial light pulses (e.g., NIR wavelength) and retina warm white light (e.g., broadband) can be applied simultaneously and be synchronized to a characteristic of a patient. For example, the characteristic can include a dominant frequency of the patient's circadian rhythm (e.g., sleep-wake cycle, 24-hour biological clock), brain state (e.g., delta brain waves, theta brain waves, alpha brain waves, beta brain waves, gamma brain waves), and/or measured EEG signals. In some embodiments, treatment can be applied during a sleep mode (resting) or during an awake mode (active) for different effects.

Exemplary Stimulation System and Apparatus

As discussed above, neurological abnormalities (e.g., disorders, diseases, dementia, epilepsy, etc.) can cause a loss of cognitive ability that can interfere with a person's daily functions (e.g., thinking, learning, knowing, memory, recall, recognition, perception, judgment, etc.). Neurological abnormalities can include a collection of symptoms caused by a variety of different disorders, diseases, and/or conditions. For example, Alzheimer's disease is a neurodegenerative disease associated with the buildup of plaque (e.g., amyloid aggregates) on the surface of the brain.

High-energy laser therapy has been used to surgically cut, cauterize, and/or ablate biological tissue. Low-level or low-power laser therapy has been used to treat different ailments (e.g., muscle pain, headaches, inflammation, etc.) by administering therapeutic light energy at low power to the surface of the body for biostimulation of tissues. Low-level light therapy can be applied to a patient's head to enhance neurological functions of neurons in both healthy and diseased states by controlling various parameters of the light energy (e.g., power density, intensity, wavelength, etc.). Light energy can be delivered through the skull of a patient to a target area in the patient's brain to enhance neurologic functioning (e.g., via photobiomodulation, photochemical reactions, etc.).

Photobiomodulation is a form of light therapy utilizing low-level non-ionizing light sources (e.g., lasers, light emitting diodes (LEDs), and/or broadband light) in the visible (VIS) (e.g., 400 nm to 700 nm) and near-infrared (NIR) (e.g., 700 nm to 1100 nm) wavelengths to stimulate photochemical changes within cellular structures that are receptive to certain photons. The application of a therapeutic dose of light to impaired or dysfunctional tissue can lead to a cellular response mediated by, for example, mitochondrial mechanisms that can reduce pain, inflammation, and/or encourage healing.

At the cellular level, light energy (e.g., VIS, NIR) can be absorbed by mitochondria, which produce cellular energy (e.g., ATP). The primary element for the absorption process is a chromophore, which is a part of a molecule responsible for its color. For example, cytochrome c complex located in the inner membrane of the cell mitochondria can accept photonic energy of certain wavelengths when functioning poorly (e.g., unhealthy, abnormal). Photobiomodulation is a nonthermal process that can involve endogenous (e.g., within cells or tissues) chromophores eliciting photophysical (e.g., linear and nonlinear photoexcitations) and photochemical reactions at various biological scales. A photochemical reaction occurs when a chemical substance (e.g., a neuron, a cell) absorbs light.

A neuron or nerve cell is an electrically excitable cell. Cell excitability is the change in membrane potential necessary for cellular responses in various tissues. The resting and threshold potentials form the basis of cell excitability and generate graded and action potentials. In a human, there are roughly 10-20 billion neurons in the cerebral cortex and 55-70 billion neurons in the cerebellum. Neural tissue can generate oscillatory activity in many ways including by mechanisms within individual neurons or by interactions between neurons. In an individual neuron, oscillations can arise in the membrane potential or as rhythmic patterns of action potentials. Neural ensembles can give rise to macroscopic oscillations that can be observed by electrophysiological methods (e.g., an electroencephalogram).

Electroencephalography (EEG) is an electrophysiological monitoring method to observe and record electrical activity of a patient's brain. EEG measures voltage fluctuations resulting from ionic current within the neurons of the brain. EEG signals measure the brain's spontaneous electrical activity over a period of time as recorded from multiple electrodes placed on a patient's scalp. EEG signals can measure neural oscillations (e.g., brain waves) of the patient's brain over time in the frequency domain.

Neural oscillations or brain waves are rhythmic or repetitive patterns of neural activity. Brain waves have been categorized into five different types based on dominant frequency signatures: delta, theta, alpha, beta, and gamma. Delta waves are neural oscillations in the frequency range of about 0.1-4 Hz and occur when a patient is in a deep, dreamless sleep (e.g., loss of bodily awareness). Theta waves are neural oscillations in the frequency range of about 4-8 Hz and occur when a patient has a reduced consciousness (e.g., deep meditation, dreams, light sleep, REM sleep). Alpha waves are neural oscillations in the frequency range of about 8-12 Hz and occur when a patient is physically and mentally relaxed (e.g., awake but drowsy). Beta waves are neural oscillations in the frequency range of about 12-30 Hz and occur when a patient is awake and conscious (e.g., alert). Gamma waves are neural oscillations in the frequency range of about 30-140 Hz (e.g., 40 Hz) and occur when a patient has heightened perception.

Gamma waves are correlated with large scale brain network activity and cognitive phenomena. Altered gamma activity has been observed in cognitive disorders (e.g., Alzheimer's disease). Synchronization of gamma oscillations via non-invasive stimuli in the gamma frequency band (e.g., 40 Hz), for example, by flashes of light or pulses of sound can reduce amyloid aggregates (e.g., amyloid beta Aβ) and activate microglia (e.g., non-neuronal cells throughout the brain and spinal cord). However, the precise molecular and cellular mechanisms by which gamma band stimulation (e.g., constant 40 Hz frequency) produce cognitive improvements in certain neurological abnormalities (e.g., Alzheimer's disease) is unknown.

Embodiments of stimulation apparatuses, systems, and methods as discussed below can provide higher efficacy of treatment of neurological abnormalities, enhance neurologic functioning, and increase detoxification of the brain.

Figure 1A:
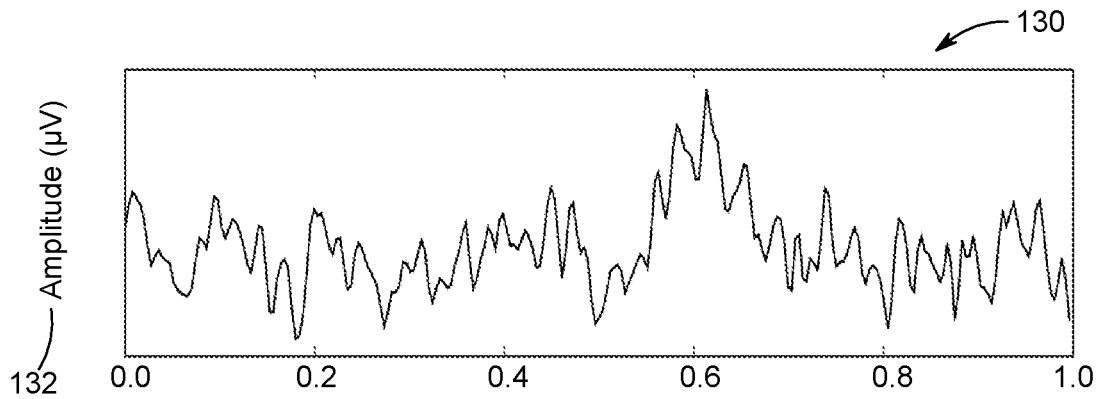
FIG. 1A is a schematic illustration of a local electroencephalogram from the stimulation system shown in FIG. 1, according to an exemplary embodiment.
Figure 1B:
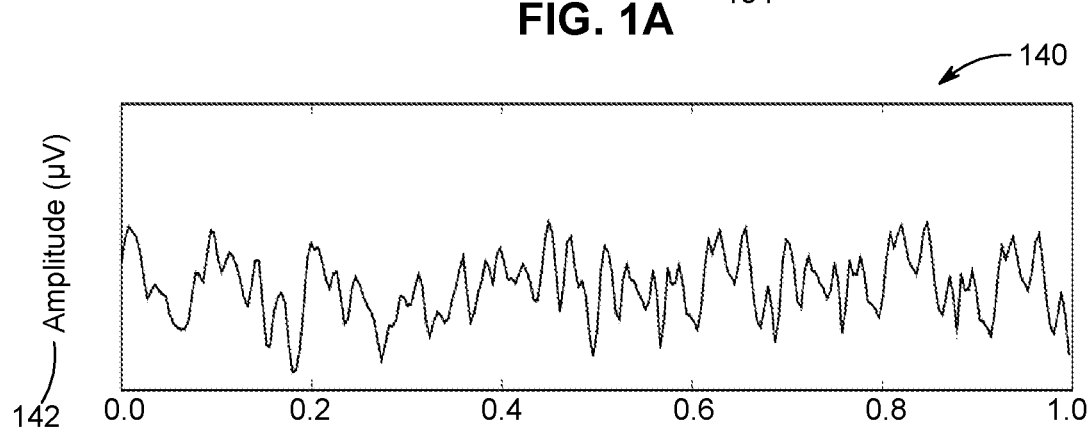
FIG. 1B is a schematic illustration of a local electroencephalogram from the stimulation system shown in FIG. 1, according to an exemplary embodiment.
Figure 1C:
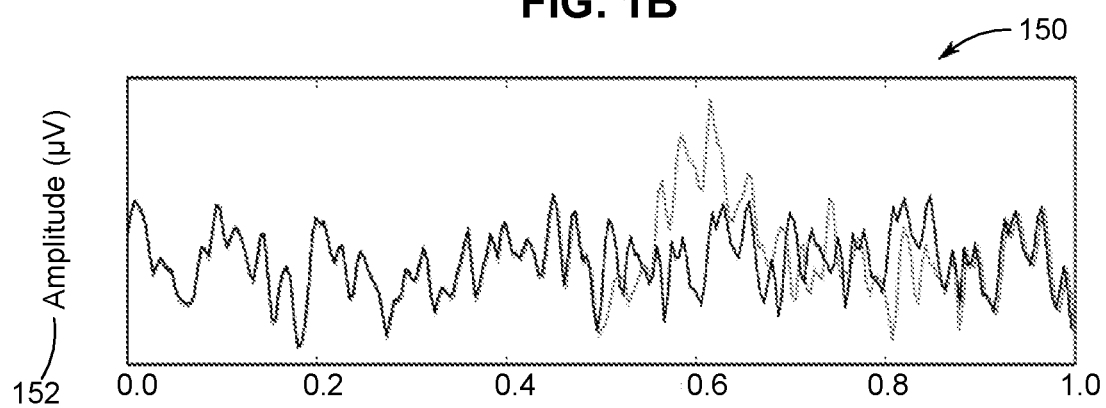
FIG. 1C is a schematic illustration of a global electroencephalogram from the stimulation system shown in FIG. 1, according to an exemplary embodiment.

FIGS. 1-4 illustrate stimulation system 100 with stimulation apparatus 200, according to various exemplary embodiments. FIG. 1 is a schematic perspective illustration of stimulation system 100 with stimulation apparatus 200, according to an exemplary embodiment. FIG. 1A is a schematic illustration of local EEG signal 130 from stimulation system 100 shown in FIG. 1, according to an exemplary embodiment. FIG. 1B is a schematic illustration of local EEG signal 140 from stimulation system 100 shown in FIG. 1, according to an exemplary embodiment. FIG. 1C is a schematic illustration of global EEG signal 150 from stimulation system 100 shown in FIG. 1, according to an exemplary embodiment.

Figure 2A:
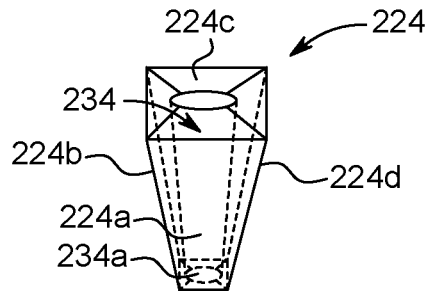
FIG. 2A is a schematic perspective illustration of an electrode of the stimulation apparatus shown in FIG. 1, according to an exemplary embodiment.
Figure 2:
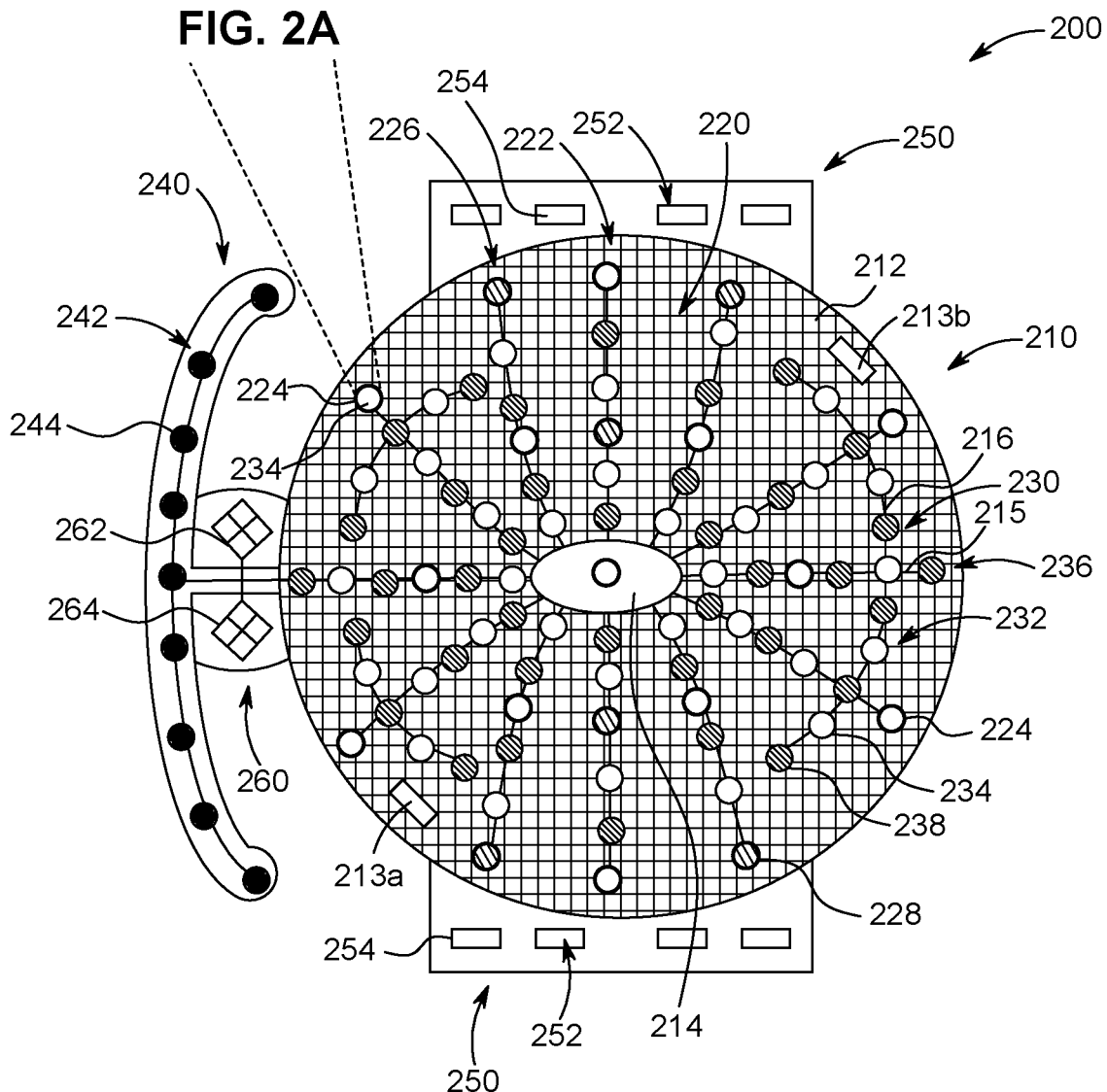
FIG. 2 is a schematic cross-sectional plan view of the stimulation apparatus shown in FIG. 1, according to an exemplary embodiment.
Figure 3:
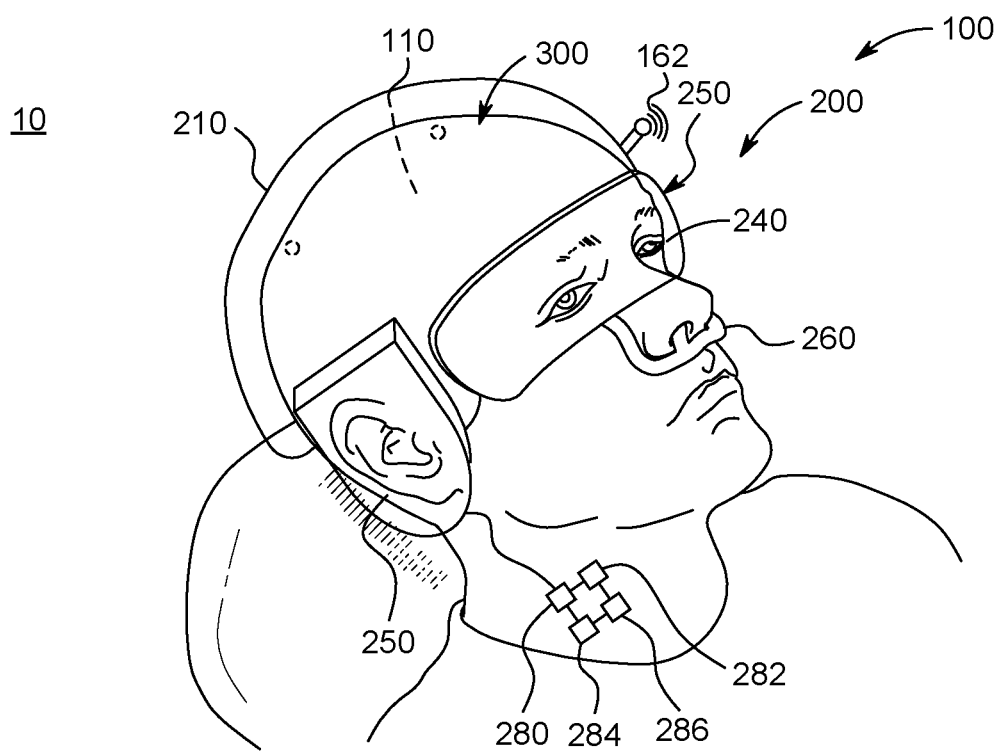
FIG. 3 is a schematic perspective illustration of the stimulation system shown in FIG. 1 during an awake configuration, according to an exemplary embodiment.
Figure 4:
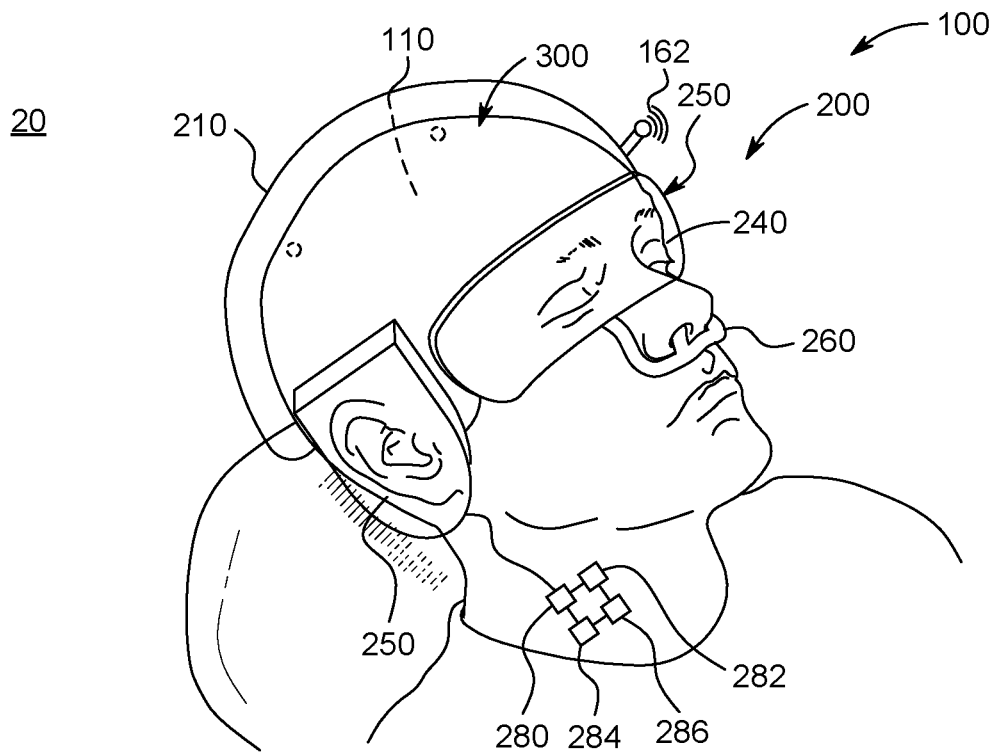
FIG. 4 is a schematic perspective illustration of the stimulation system shown in FIG. 1 during a sleep configuration, according to an exemplary embodiment.

FIG. 2 is a schematic cross-sectional plan view of stimulation apparatus 200 shown in FIG. 1 (along the plane indicated by II-II in FIG. 1), according to an exemplary embodiment. FIG. 2A is a schematic perspective illustration of electrode 224 of stimulation apparatus 200 shown in FIG. 1, according to an exemplary embodiment. FIG. 3 is a schematic perspective illustration of stimulation system 100 shown in FIG. 1 during an awake configuration, according to an exemplary embodiment. FIG. 4 is a schematic perspective illustration of stimulation system 100 shown in FIG. 1 during a sleep configuration, according to an exemplary embodiment. Although stimulation system 100 and stimulation apparatus 200 are shown in FIGS. 1-4 as a stand-alone apparatus and/or system, the embodiments of this disclosure can be used with other apparatuses and/or systems, such as, but not limited to, processor 170, smart phone 180, tremor sensor 280, pulse sensor 282, temperature sensor 284, oxygen saturation ($SpO_2$) sensor 286, and/or control unit 300.

As shown in FIG. 1, stimulation system 100 can include connector 160, processor 170, smart device 180, stimulation apparatus 200, and/or control unit 300. Stimulation system 100 can be configured to dynamically measure EEG signals (e.g., local EEG signal 130, local EEG signal 140, global EEG signal 150) from brain waves 110 of patient 102 and dynamically stimulate the brain of patient 102 by emitting energy based on the measured EEG signals (e.g., local EEG signal 130, local EEG signal 140, global EEG signal 150) to treat a neurological disorder and/or disease of patient 102.

Connector 160 can be configured to provide an electrical and/or optical link between processor 170 and stimulation apparatus 200. Connector 160 can be further configured to provide a wireless connection between smart phone 180 and stimulation apparatus 200. Connector 160 can include transceiver 161 capable of receiving wireless signals (e.g., wireless signals 182 from smart device 180) and sending wireless signals 162. In some embodiments, connector 160 can be coupled to processor 170 and stimulation apparatus 200. In some embodiments, connector 160 can be wirelessly coupled to smart device 180 and stimulation apparatus 200. In some embodiments, connector 160 can transmit wireless signals 162 and receive wireless signals 182 via a transceiver 161 to and from smart device 180. For example, wireless signals 182 from smart device 180 can provide data inputs and/or instructions to connector 160 that can be transferred to processor 170 and/or stimulation apparatus 200.

Processor 170 can be configured to communicate with stimulation apparatus 200. Processor 170 can be coupled to stimulation apparatus 200 via connector 160. In some embodiments, processor 170 can be external to stimulation apparatus 200. In some embodiments, processor 170 can be part of stimulation apparatus 200. For example, processor 170 can be coupled to or part of control unit 300 of stimulation apparatus 200. In some embodiments, processor 170 can perform calculations and/or implement algorithms based on data received from stimulation apparatus 200 (e.g., measured EEG signals). For example, processor 170 can perform FFT analysis and/or spectrum analysis of measured EEG signals from stimulation apparatus 200. In some embodiments, processor 170 can compute a global combined EEG signal based on local EEG signals from stimulation apparatus 200. For example, as shown in FIG. 1, processor 170 can receive local EEG signals 130, 140 from stimulation apparatus 200 and calculate global EEG signal 150 based on a heuristic model and/or statistical algorithm (e.g., averaging, median, Antonyan Vardan Transform (AVT), cascaded AVT, reverse AVT, neural network, machine-learning, etc.). In some embodiments, processor 170 can be part of a computer processing unit (CPU), a server, and/or a cluster.

Smart device 180 can be configured to provide data and/or instructions to stimulation apparatus 200. Smart device 180 can be coupled to stimulation apparatus 200 via wireless communication. In some embodiments, smart device 180 can be controlled by patient 102 in order to operate stimulation apparatus 200 unaccompanied. For example, patient 102 can specify a time period for stimulation apparatus 200 to be applied to patient 102 (e.g., during sleep configuration 20 shown in FIG. 4). In some embodiments, smart device 180 can control stimulation apparatus 200 through wireless signals 182. For example, smart device 180 can initiate one or more programs or stimulation routines in stimulation apparatus 200. In some embodiments, smart device 180 can receive data and/or information from stimulation apparatus 200. For example, smart device 180 can receive periodic updates and/or time graphs (e.g., daily, weekly, monthly, etc.) regarding programs or stimulation routines implemented by stimulation apparatus 200. In some embodiments, smart device 180 can receive data and/or information from stimulation apparatus 200 regarding enhanced neurological functioning of patient 102. For example, smart device 180 can receive values and/or time graphs (e.g., daily, weekly, monthly, etc.) regarding certain parameters positively correlated with enhanced neurological functioning of patient 102, for example, reduced tremors (e.g., tremor sensor 280), improved oxygen saturation (e.g., $SpO_2$ sensor 286), etc.

As shown in FIGS. 1 and 2, stimulation apparatus 200 can include headpiece 210, eyepiece 240, earpiece 250, nosepiece 260, tremor sensor 280, pulse sensor 282, temperature sensor 284, $SpO_2$ sensor 286, and/or control unit 300. Stimulation apparatus 200 can be configured to dynamically measure EEG signals (e.g., local EEG signal 130, local EEG signal 140, global EEG signal 150) of patient 102 and dynamically emit radiation to patient 102 based on the measured EEG signals for treatment of a neurological abnormality.

As shown in FIG. 1A, local EEG signal 130 can be measured by stimulation apparatus 200, which includes amplitude (μV) 132 measured over time (sec) 134 from a particular electrode of stimulation apparatus 200. As shown in FIG. 1B, local EEG signal 140 can be measured by stimulation apparatus 200, which includes amplitude (μV) 142 measured over time (sec) 144 from a particular electrode of stimulation apparatus 200 (e.g., separate from local EEG signal 130). As shown in FIG. 1C, global EEG signal 150 can be measured and/or calculated by stimulation apparatus 200, which includes amplitude (μV) 152 measured over time (sec) 154 from a combination of electrodes of stimulation apparatus 200 (e.g., combination of local EEG signals 130, 140). In some embodiments, global EEG signal 150 can be measured and/or calculated by combining one or more local EEG signals (e.g., local EEG signals 130, 140) of stimulation apparatus 200. For example, processor 170 and/or stimulation apparatus 200 can receive local EEG signals 130, 140 and calculate global EEG signal 150 based on a heuristic model and/or statistical algorithm (e.g., averaging, median, AVT, cascaded AVT, reverse AVT, neural network, machine-learning, etc.).

As shown in FIG. 2, headpiece 210 can include elastic mesh 212, flexible printed circuit board (PCB) 214, electrode array 220, and/or light emitter array 230. Headpiece 210 can be configured to dynamically measure transcranial EEG signals from the head of patient 102 (e.g., local EEG signals 130, 140) and dynamically emit radiation to the head of patient 102 based on the measured transcranial EEG signals (e.g., local EEG signals 130, 140). In some embodiments, headpiece 210 can be shaped as a headband, a patch, a cap, a helmet, a strap, and/or any other suitable covering that can be adhered to the head of patient 102. For example, as shown in FIGS. 1 and 2, stimulation apparatus 200 can be a helmet adhered to the head of patient 102.

Elastic mesh 212 can be configured to adhere to the scalp of patient 102. Elastic mesh can be coupled to flexible PCB 214. In some embodiments, elastic mesh 212 can be disposed along an interior of headpiece 210 to provide a snug fit with the head of patient 102. In some embodiments, elastic mesh 212 can include one or more cooling agents 213a and/or temperature sensors 213b to regulate a surface temperature of the scalp of patient 102. For example, elastic mesh 212 can include temperature sensor 213b (e.g., similar to temperature sensor 284 shown in FIG. 1).

Flexible PCB 214 can be configured to be coupled to electrode array 220 and light emitter array 230 and provide necessary power and electrical and/or optical communication to electrode array 220 and light emitter array 230, for example, from control unit 300 and/or processor 170. In some embodiments, flexible PCB 214 can be patterned to include one or more radial fingers 215 extending from a center of headpiece 210 and/or one or more circumferential portions 216 coupled to radial fingers 215 and extending circumferentially (e.g., a ring) from the center of headpiece 210. For example, as shown in FIG. 2, flexible PCB 214 can include symmetrically arranged radial fingers 215 coupled to circumferential portions 216. In some embodiments, flexible PCB 214 can extend beyond a perimeter of headpiece 210 to form eyepiece 240, earpiece 250, and/or nosepiece 260. For example, as shown in FIG. 2, flexible PCB 214 can be coupled to eyepiece 240, earpiece 250, and nosepiece 260. In some embodiments, flexible PCB 214 can be patterned in optimal electrode detection positions. For example, as shown in FIG. 2, flexible PCB 214 can include symmetrically arranged radial fingers 215 and circumferential portions 216.

As shown in FIG. 2, electrode array 220 can include first electrode array 222 and second electrode array 226. Electrode array 220 can be configured to dynamically measure EEG signals (e.g., local EEG signal 130 shown in FIG. 1A, local EEG signal 140 shown in FIG. 1B) from brain waves 110 of patient 102. First electrode array 222 can be configured to measure first transcranial EEG signals of patient 102 (e.g., local EEG signal 130 shown in FIG. 1A). First electrode array 222 can include a plurality of first electrodes 224, for example, first electrode 224 shown in FIG. 2A. Second electrode array 226 can be configured to measure second transcranial EEG signals of patient 102 (e.g., local EEG signal 140 shown in FIG. 1B). Second electrode array 226 can include a plurality of second electrodes 228, for example, similar to first electrode 224 shown in FIG. 2A. In some embodiments, first and second electrodes 224, 228 can be hollow electrodes configured to surround a corresponding light emitter. For example, as shown in FIGS. 2 and 2A, first and second electrodes 224, 228 can be arranged around corresponding light emitters 234, 238, respectively, in optimal EEG electrode positions.

In some embodiments, electrode array 220 can include one or more electrodes having a conical and/or pyramidal shape with a plurality of sub-electrodes for measuring EEG signals. For example, as shown in FIG. 2A, electrode array 220 can include first electrode 224 with sub-electrodes 224a, 224b, 224c, 224d forming a conical and/or pyramidal shape. In some embodiments, first electrode array 222 and/or second electrode array 226 can include first and second electrodes 224, 228 having a conical and/or pyramidal shape with a plurality of sub-electrodes for measuring EEG signals (e.g., similar to sub-electrodes 224a, 224b, 224c, 224d shown in FIG. 2A).

As shown in FIGS. 2 and 2A, light emitter array 230 can include first light emitter array 232 and second light emitter array 236. Light emitter array 230 can be configured to dynamically emit light energy based on the measured EEG signals (e.g., local EEG signal 130 shown in FIG. 1A, local EEG signal 140 shown in FIG. 1B) for treatment of a neurological abnormality of patient 102. In some embodiments, light emitter array 230 can include one or more light sources (e.g., lasers, light emitting diodes (LEDs), and/or broadband light), to provide light energy therapy. For example, light emitter array 230 can include LEDs emitting pulsed light. In some embodiments, light emitter array 230 can emit light in the visible (VIS) (e.g., 400 nm to 700 nm), near-infrared (NIR) (e.g., 700 nm to 1100 nm), and/or broadband (e.g., white light) wavelengths. For example, light emitter array 230 can emit light having a VIS wavelength (e.g., about 670 nm) and/or a NIR wavelength (e.g., about 850 nm).

First light emitter array 232 can be configured to dynamically emit first radiation based on first transcranial EEG signals of patient 102 (e.g., local EEG signal 130 shown in FIG. 1A). First light emitter array 232 can include a plurality of first light emitters 234, for example, first light emitter 234 shown in FIG. 2A. In some embodiments, first light emitter 234 can include lens 234a for focusing first radiation onto the head of patient 102. For example, as shown in FIG. 2A, lens 234a can be positioned at a distal end of first light emitter 234. In some embodiments, one or more first light emitters 234 can be enclosed by first electrodes 224 of first electrode array 222. For example, as shown in FIG. 2A, first light emitter 234 can be embedded and/or disposed within a hollow cavity of first electrode 224. In some embodiments, lens 234a can have a conical and/or pyramidal shape in order to part hair of patient 102 and directly contact the scalp of patient 102. In some embodiments, first light emitter 234 can include a laser, an LED, or a broadband light source. For example, first light emitter 234 can be an LED emitting pulsed light. In some embodiments, first light emitter 234 can emit light in the visible (VIS) (e.g., 400 nm to 700 nm), near-infrared (NIR) (e.g., 700 nm to 1100 nm), and/or broadband (e.g., white light) wavelengths. For example, first light emitter 234 can emit light having a VIS wavelength, for example, at about 670 nm to target specific absorption bands in the tissues of patient 102.

Second light emitter array 236 can be configured to dynamically emit second radiation based on second transcranial EEG signals of patient 102 (e.g., local EEG signal 140 shown in FIG. 1B). Second light emitter array 236 can include a plurality of second light emitters 238, for example, similar to first light emitter 234 shown in FIG. 2A. In some embodiments, second light emitter 238 can include a lens (e.g., similar to lens 234a shown in FIG. 2A) for focusing second radiation onto the head of patient 102. In some embodiments, one or more second light emitters 238 can be enclosed by second electrodes 228 of second electrode array 226. For example, as shown in FIG. 2, second light emitter 238 can be embedded and/or disposed within a hollow cavity of second electrode 228 (e.g., similar to first light emitter 234 shown in FIG. 2A). In some embodiments, second light emitter 238 can include a laser, an LED, or a broadband light source. For example, second light emitter 238 can be an LED emitting pulsed light. In some embodiments, second light emitter 238 can emit light in the visible (VIS) (e.g., 400 nm to 700 nm), near-infrared (NIR) (e.g., 700 nm to 1100 nm), and/or broadband (e.g., white light) wavelengths. For example, second light emitter 238 can emit light having a NIR wavelength, for example, at about 850 nm to target specific absorption bands in the tissues of patient 102.

In some embodiments, light emitter array 230 can be controlled by control unit 300. For example, control unit 300 can receive measured EEG signals (e.g., local EEG signal 130 shown in FIG. 1A, local EEG signal 140 shown in FIG.

Figure 19:
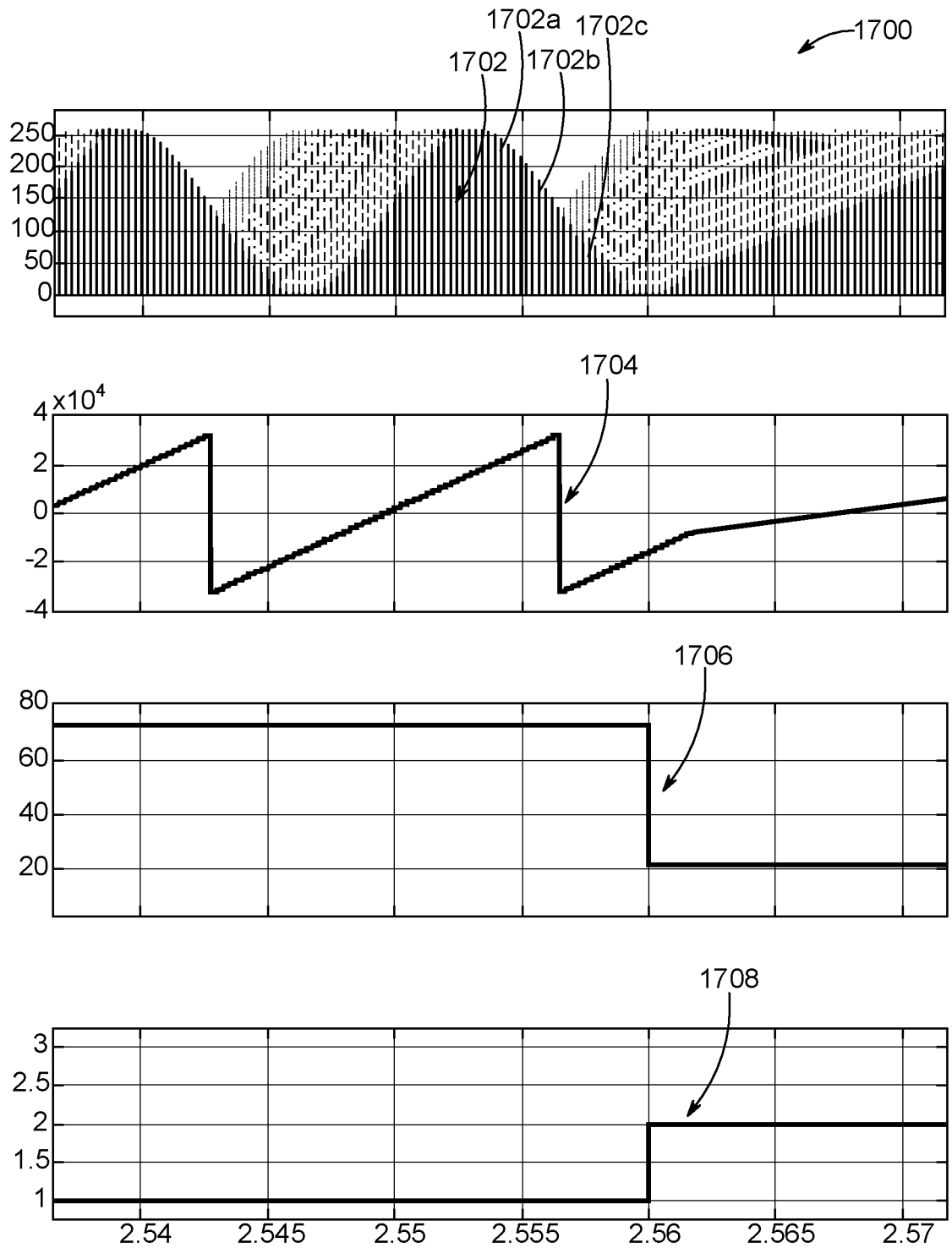
FIG. 19 is an enhanced view of the pulsed (PWM) waveform shown in FIG. 18, according to an exemplary embodiment.
Figure 20A:
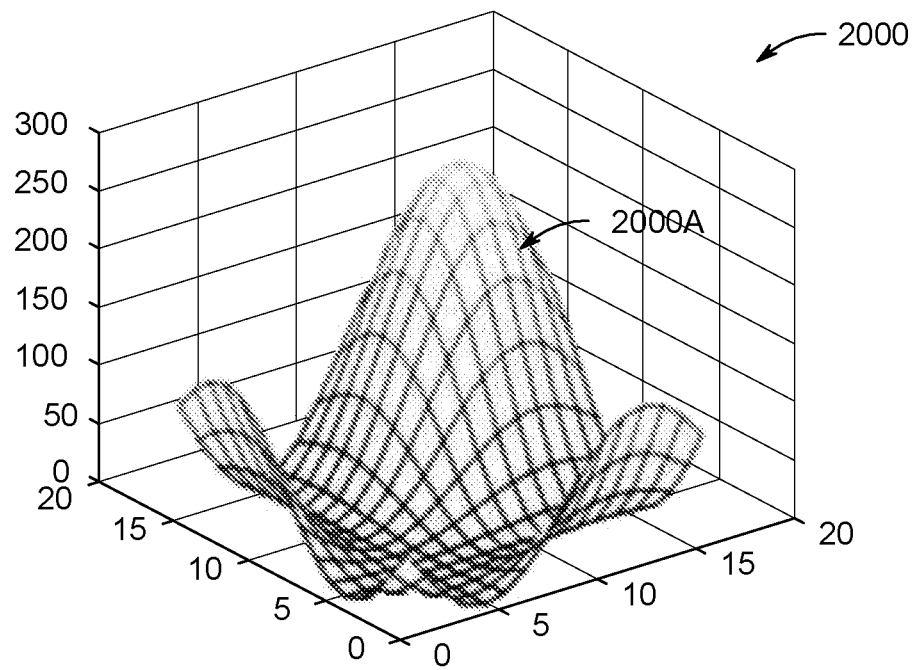
FIGS. 20A-20D are a schematic illustration of a spatial wave of a pulsed emitter array over increments of $\pi/4$, according to an exemplary embodiment.
Figure 20B:
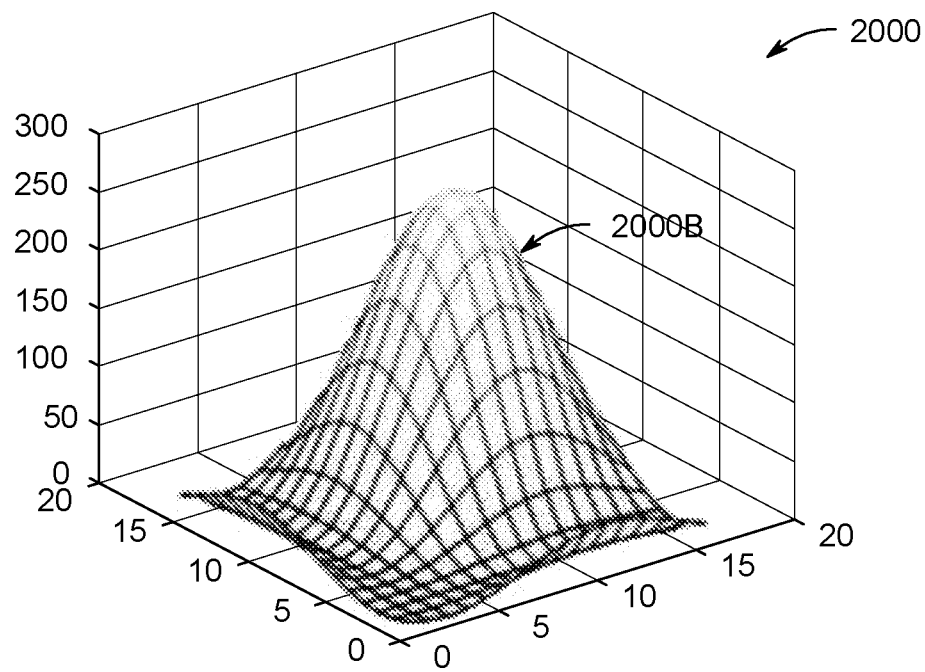
Figure 20C:
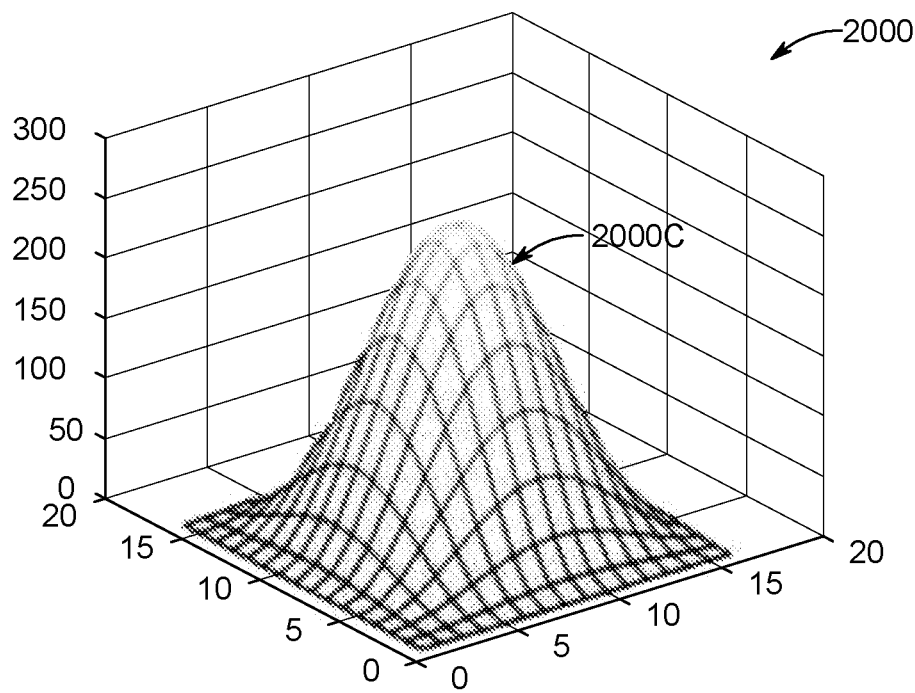
Figure 20D:
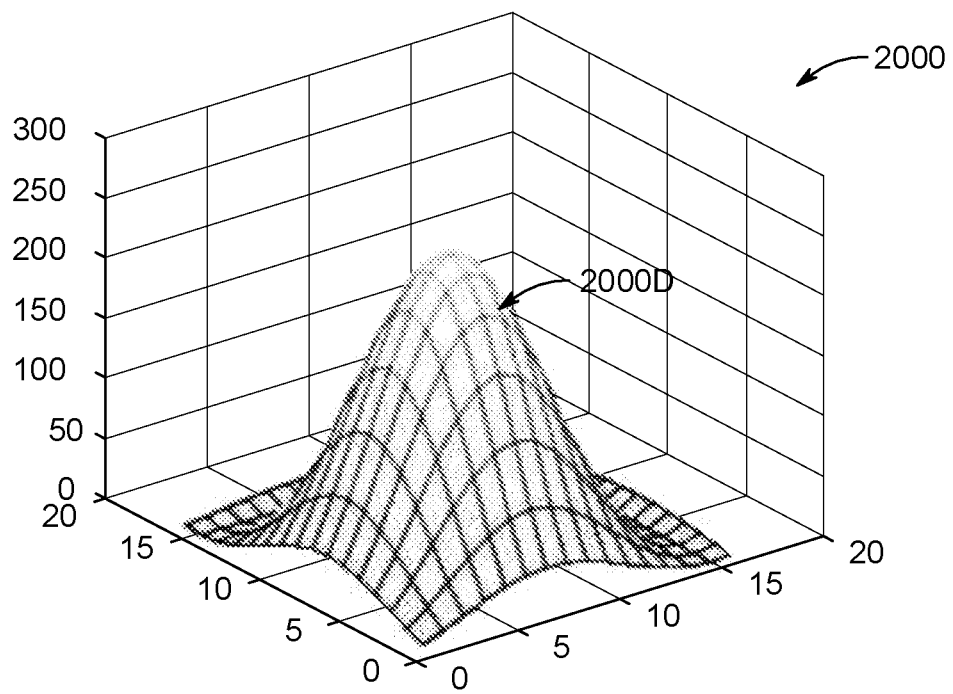
Figure 21A:
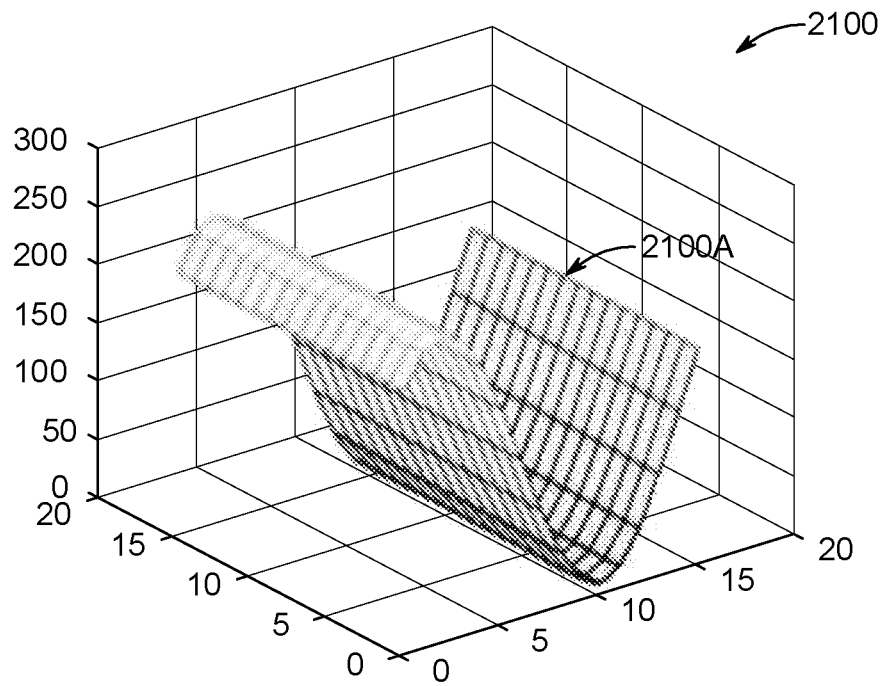
FIGS. 21A-21D are a schematic illustration of a spatial wave of a pulsed emitter array over increments of $\pi/4$, according to an exemplary embodiment.
Figure 21B:
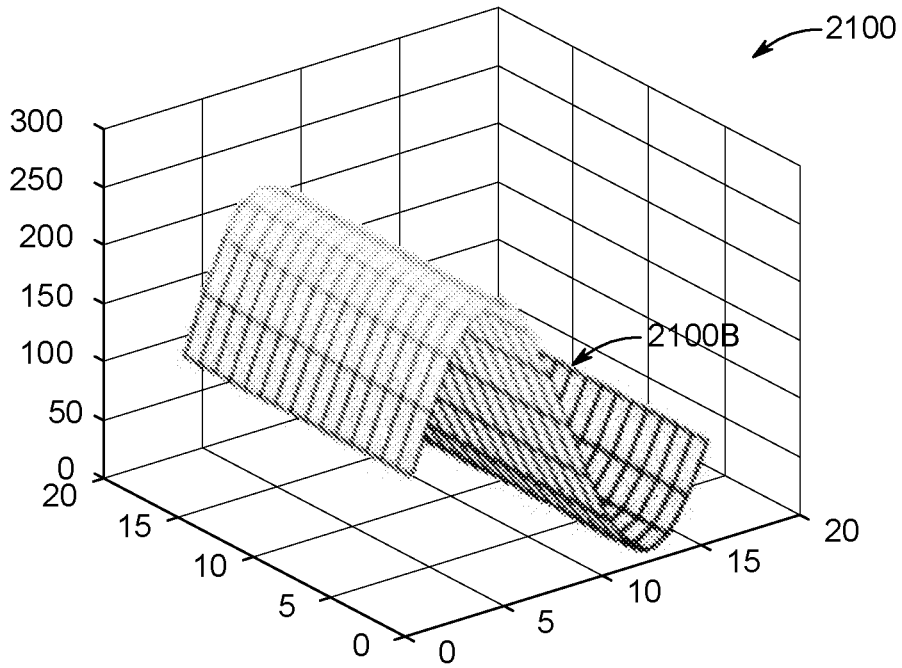
Figure 21C:
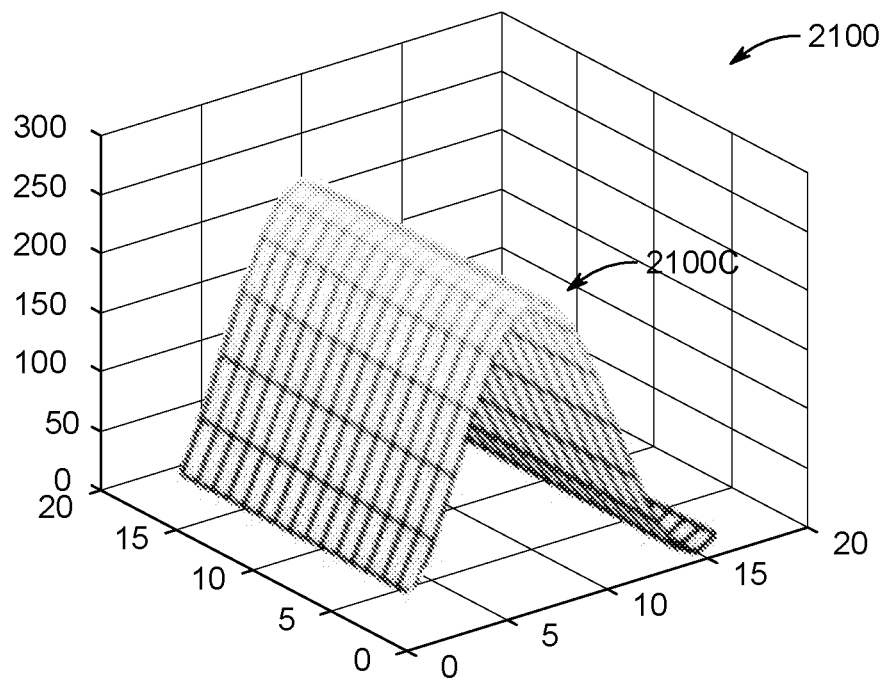
Figure 21D:
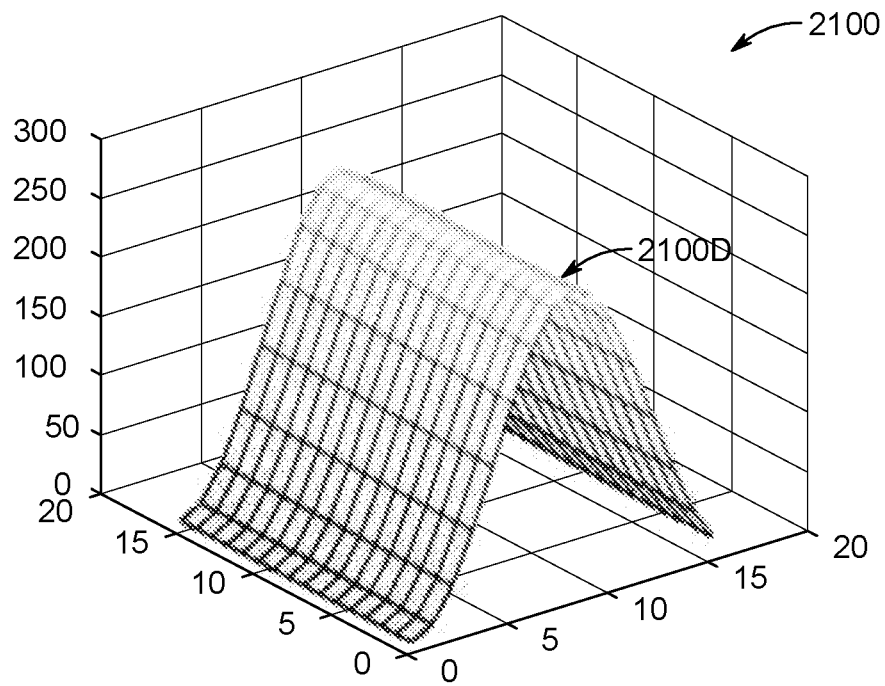

1B) from electrode array 220 and control (e.g., via electrical control signals) light emitter array 230 to emit a sequence of optical macro pulses (e.g., macro pulse 1702 shown in FIG. 19, spatial wave 2000 shown in FIGS. 20A-20D, spatial wave 2100 shown in FIGS. 21A-21D), each having a defined shape, based on the measured EEG signals (e.g., local EEG signal 130 shown in FIG. 1A, local EEG signal 140 shown in FIG. 1B). In some embodiments, each optical macro pulse of the sequence of optical macro pulses (e.g., macro pulse 1702 shown in FIG. 19) can be composed of a sequence of PWM filling pulses. For example, as shown in FIG. 19, macro pulse 1702 can include PWM fillings pulses 1702*a*, 1702*b*, 1702*c*, etc.

As shown in FIGS. 1 and 2, eyepiece 240 can include third light emitter array 242 having a plurality of third light emitters 244. Eyepiece 240 can be configured to dynamically emit warm white light radiation (e.g., broadband) based on measured transcranial EEG signals of patient 102 (e.g., local EEG signal 130 shown in FIG. 1A, local EEG signal 140 shown in FIG. 1B) for treatment of a neurological abnormality of patient 102. Eyepiece 240 can be coupled to flexible PCB 214 and disposed below an underside of headpiece 210 to be in line with the eyes of patient 102. In some embodiments, third light emitter 244 can include a laser, an LED, or a broadband light source. For example, third light emitter 244 can be a white light LED emitting broadband pulsed light. In some embodiments, third light emitter 244 can emit warm white light (e.g., broadband) to target specific absorption bands in the tissues (e.g., retina, occipital lobe, etc.) of patient 102.

In some embodiments, third light emitter array 242 can be controlled by control unit 300. For example, control unit 300 can receive measured EEG signals (e.g., local EEG signal 130 shown in FIG. 1A, local EEG signal 140 shown in FIG. 1B) from electrode array 220 and control (e.g., via electrical control signals) third light emitter array 242 to emit a sequence of optical macro pulses (e.g., macro pulse 1702 shown in FIG. 19), each having a defined shape, based on the measured EEG signals (e.g., local EEG signal 130 shown in FIG. 1A, local EEG signal 140 shown in FIG. 1B). In some embodiments, each optical macro pulse of the sequence of optical macro pulses (e.g., macro pulse 1702 shown in FIG. 19) can be composed of a sequence of PWM filling pulses. For example, as shown in FIG. 19, macro pulse 1702 can include PWM fillings pulses 1702*a*, 1702*b*, 1702*c*, etc.

As shown in FIGS. 1 and 2, earpiece 250 can include acoustic emitter array 252 having a plurality of acoustic emitters 254. Earpiece 250 can be configured to dynamically emit acoustic radiation based on measured transcranial EEG signals of patient 102 (e.g., local EEG signal 130 shown in FIG. 1A, local EEG signal 140 shown in FIG. 1B) for treatment of a neurological abnormality of patient 102. Earpiece 250 can be coupled to flexible PCB 214 and disposed radially exterior to headpiece 210 to be aligned with the ears of patient 102. In some embodiments, acoustic emitter array 252 can include a speaker, a MEMS oscillator, an acoustic transducer, and/or any other device that can convert electrical energy to acoustic energy (e.g., pressure waves). For example, acoustic emitter 254 can be a speaker emitting pulsed sounds. In some embodiments, acoustic emitter 254 can emit pulsed sounds having a frequency from about 0.1 Hz to about 20,000 Hz to target specific absorption bands in the tissues (e.g., cochlea, temporal lobe, etc.) of patient 102. For example, acoustic emitter 254 can emit pulsed sounds at a frequency of about 40 Hz.

In some embodiments, acoustic emitter array 252 can be controlled by control unit 300. For example, control unit 300 can receive measured EEG signals (e.g., local EEG signal 130 shown in FIG. 1A, local EEG signal 140 shown in FIG. 1B) from electrode array 220 and control (e.g., via electrical control signals) acoustic emitter array 252 to emit a sequence of acoustic macro pulses (e.g., similar to macro pulse 1702 shown in FIG. 19), each having a defined shape, based on the measured EEG signals (e.g., local EEG signal 130 shown in FIG. 1A, local EEG signal 140 shown in FIG. 1B). In some embodiments, each acoustic macro pulse of the sequence of acoustic macro pulses (e.g., similar to macro pulse 1702 shown in FIG. 19) can be composed of a sequence of PWM filling pulses (e.g., similar to PWM fillings pulses 1702*a*, 1702*b*, 1702*c*).

As shown in FIGS. 1 and 2, nosepiece 260 can include fourth light emitter array 262 having a plurality of fourth light emitters 264. Nosepiece 260 can be configured to dynamically emit light energy based on the measured EEG signals (e.g., local EEG signal 130 shown in FIG. 1A, local EEG signal 140 shown in FIG. 1B) for treatment of a neurological abnormality of patient 102. Nosepiece 260 can be coupled to flexible PCB 214 and disposed below an underside of headpiece 210 to be in line with the nostrils of patient 102. In some embodiments, fourth light emitter 264 can include a laser, an LED, or a broadband light source. For example, fourth light emitter 264 can be an LED emitting pulsed light. In some embodiments, fourth light emitter 264 can emit light in the visible (VIS) (e.g., 400 nm to 700 nm), near-infrared (NIR) (e.g., 700 nm to 1100 nm), and/or broadband (e.g., white light) wavelengths. For example, fourth light emitter 264 can emit light having a VIS wavelength (e.g., about 670 nm) and/or a NIR wavelength (e.g., about 850 nm) to target specific absorption bands in the tissues (e.g., olfactory neurons, parietal lobe, etc.) of patient 102.

In some embodiments, fourth light emitter array 262 can be controlled by control unit 300. For example, control unit 300 can receive measured EEG signals (e.g., local EEG signal 130 shown in FIG. 1A, local EEG signal 140 shown in FIG. 1B) from electrode array 220 and control (e.g., via electrical control signals) fourth light emitter array 262 to emit a sequence of optical macro pulses (e.g., macro pulse 1702 shown in FIG. 19), each having a defined shape, based on the measured EEG signals (e.g., local EEG signal 130 shown in FIG. 1A, local EEG signal 140 shown in FIG. 1B). In some embodiments, each optical macro pulse of the sequence of optical macro pulses (e.g., similar to macro pulse 1702 shown in FIG. 19) can be composed of a sequence of PWM filling pulses (e.g., similar to PWM fillings pulses 1702*a*, 1702*b*, 1702*c*).

As shown in FIG. 1, tremor sensor 280, pulse sensor 282, temperature sensor 284, and/or SpO$_2$ sensor 286 can be coupled to patient 102 to monitor specific parameters and/or conditions of patient 102 over time. In some embodiments, tremor sensor 280, pulse sensor 282, temperature sensor 284, and/or SpO$_2$ sensor 286 can be coupled to one another (e.g., electrically) so that an output of each sensor can be simultaneously received by stimulation apparatus 200. In some embodiments, tremor sensor 280, pulse sensor 282, temperature sensor 284, and/or SpO$_2$ sensor 286 can be formed in a single device and disposed on a body part or extremity (e.g., a finger) of patient 102. For example, as shown in FIG. 1, tremor sensor 280, pulse sensor 282, temperature sensor 284, and SpO$_2$ sensor 286 can be formed as a patch disposed on the neck of patient 102. In some embodiments, tremor sensor 280, pulse sensor 282, temperature sensor 284, and/or SpO$_2$ sensor 286 can be disposed within headpiece 210, eyepiece 240, earpiece 250, and/or nosepiece 260 of stimulation apparatus 200.

Tremor sensor 280 can be configured to measure tremors (e.g., vibrations) of patient 102. In some embodiments, tremor sensor 280 can include a MEMS sensor, an accelerometer, a gyroscope, and/or a magnetometer to measure vibrations of patient 102. Pulse sensor 282 can be configured to measure the pulse of patient 102. In some embodiments, control unit 300 can receive data from pulse sensor 282 to determine an awake-sleep cycle and/or physical state of patient 102 (e.g., sleep, awake, heightened perception, etc.). Temperature sensor 284 can be configured to measure the temperature of patient 102. In some embodiments, control unit 300 can receive data from temperature sensor 284 to determine if a temperature threshold has been exceed (e.g., over 106° F.) and adjust the emitter pulses accordingly (e.g., adjust to a lower duty cycle and/or adjust to a higher pulse frequency). $SpO_2$ sensor 286 can be configured to measure the oxygen saturation of patient 102. In some embodiments, control unit 300 can receive data from $SpO_2$ sensor 286 to determine the efficacy of treatment of patient 102 for a particular stimulation routine.

Control unit 300 can be configured to control one or more emitter arrays of stimulation apparatus 200 based on measured EEG signals (e.g., local EEG signal 130, local EEG signal 140, global EEG signal 150) for treatment of a neurological abnormality of patient 102. In some embodiments, control unit 300 can control headpiece 210, eyepiece 240, earpiece 250, and/or nosepiece 260 to dynamically emit radiation (e.g., light energy, acoustic energy) based on measured EEGs signals (e.g., local EEG signal 130, local EEG signal 140) from electrode array 220 and/or data from tremor sensor 280, pulse sensor 282, temperature sensor 284, and/or $SpO_2$ sensor 286.

As shown in FIG. 3, stimulation system 100 can operate in an awake configuration 10, when patient 102 is in an awake cycle (e.g., alpha waves, beta waves, gamma waves). As shown in FIG. 4, stimulation system 100 can operate in a sleep configuration 20, when patient 102 is a sleep cycle (e.g., delta waves, theta waves). In some embodiments, control unit 300 can determine an awake-sleep cycle of patient 102 based on the measured EEG signals (e.g., local EEG signal 130, local EEG signal 140) from electrode array 220. In some embodiments, control unit 300 can adjust a shape of the sequence of optical and/or acoustic macro pulses based on the determined awake-sleep cycle of patient 102. For example, in awake configuration 10, control unit 300 can adjust the shape of the sequence of optical and/or acoustic macro pulses to target the awake cycle of patient 102 (e.g., alpha waves, beta waves, gamma waves—frequency of about 8 Hz to about 140 Hz). For example, in sleep configuration 20, control unit 300 can adjust the shape of the sequence of optical and/or acoustic macro pulses to target the sleep cycle of patient 102 (e.g., delta waves, theta waves—frequency of about 0.1 Hz to about 8 Hz).

Exemplary Control Unit

Figure 5:
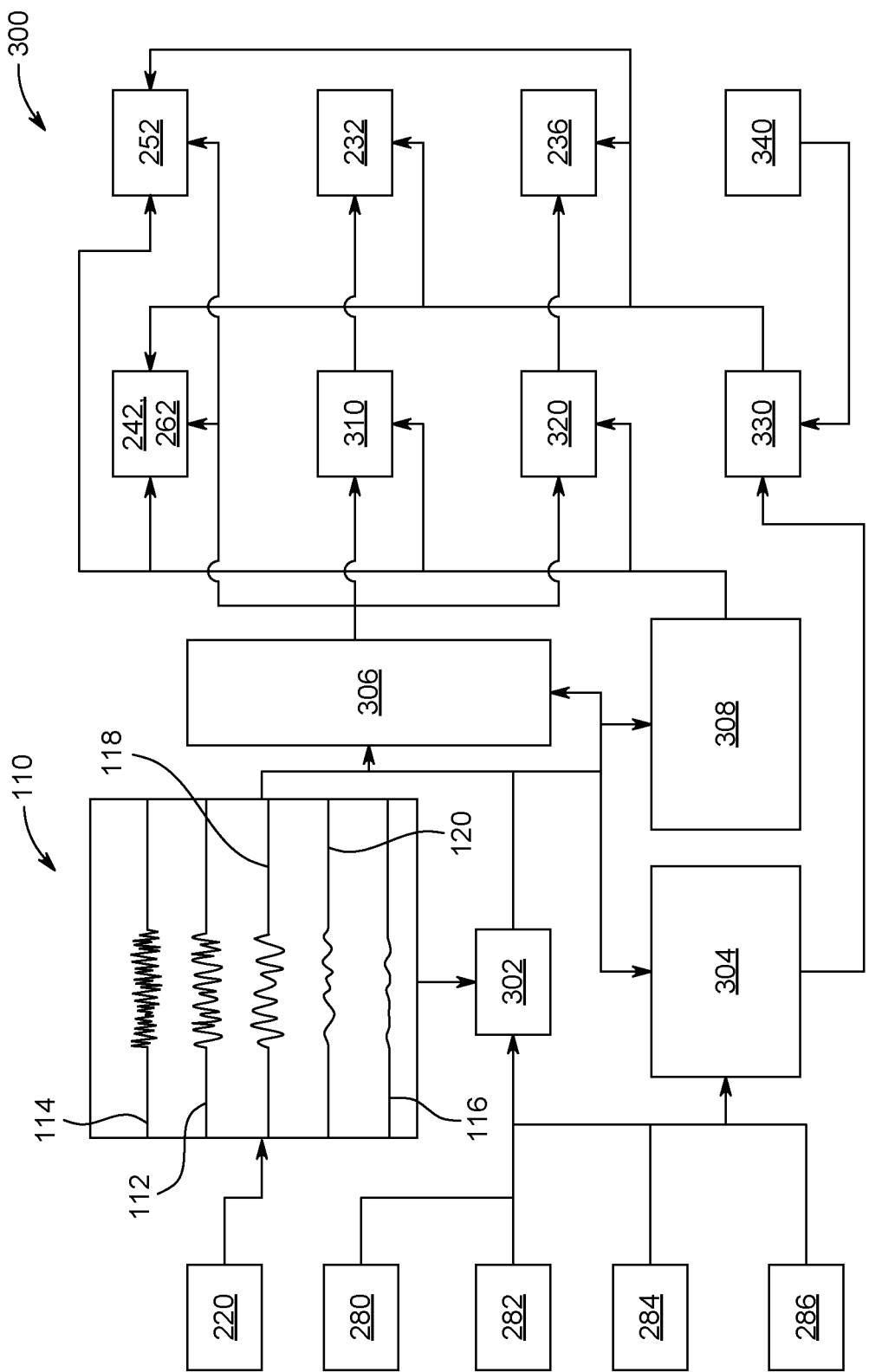
FIG. 5 is a schematic block diagram of a control unit of the stimulation system shown in FIG. 1, according to an exemplary embodiment.
Figure 6:
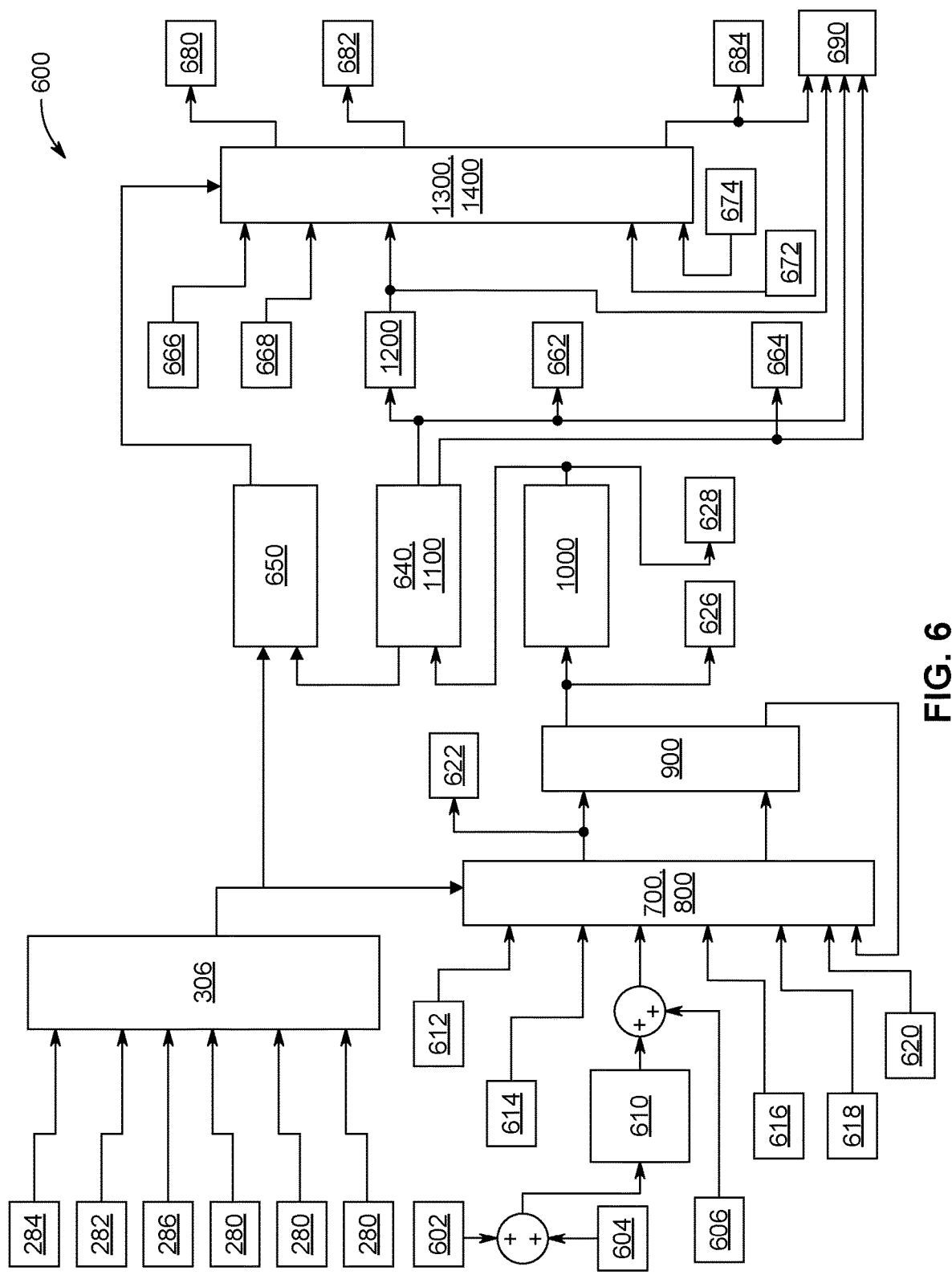
FIG. 6 is a schematic block diagram of a signal processing unit of the control unit shown in FIG. 5, according to an exemplary embodiment.
Figure 7:
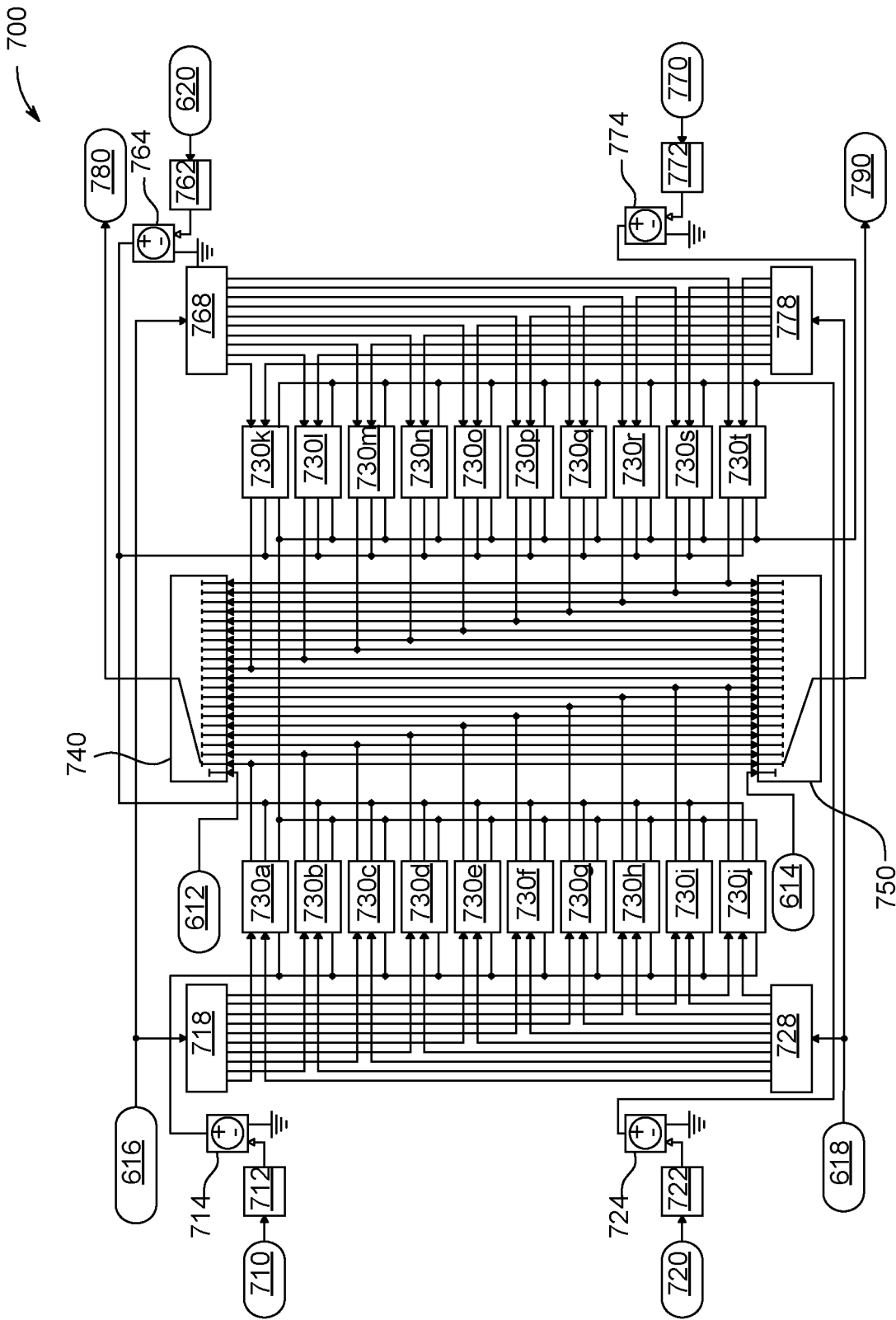
FIG. 7 is a schematic block diagram of an electrode multiplexer unit of the control unit shown in FIG. 5, according to an exemplary embodiment.
Figure 8:
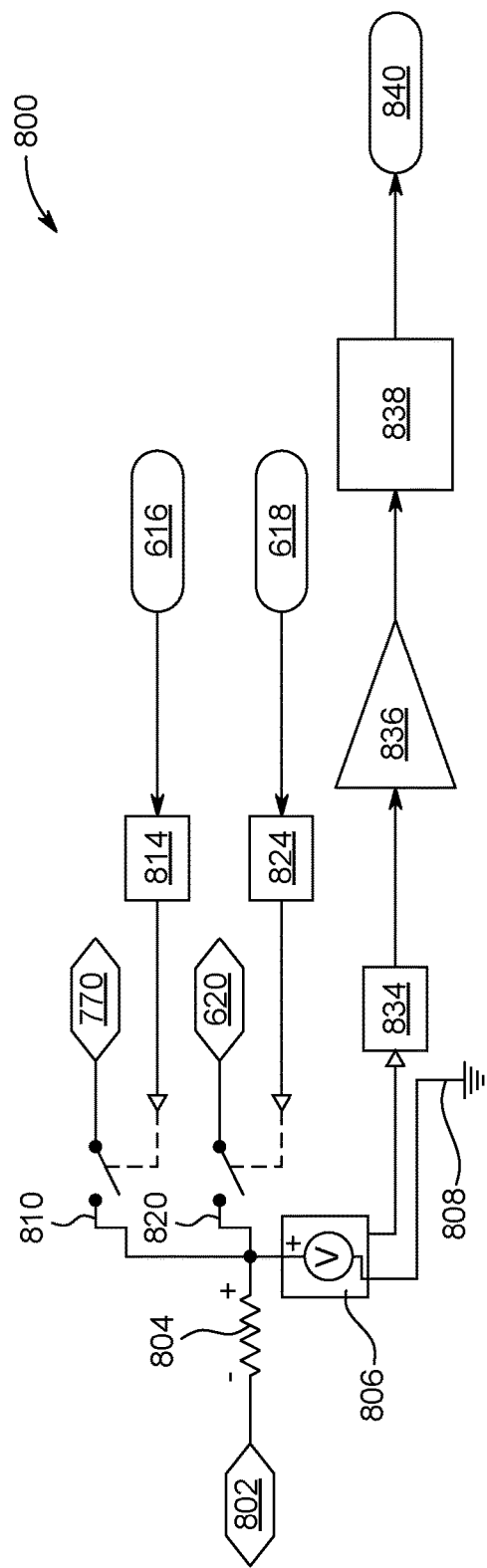
FIG. 8 is a schematic block diagram of an electrode detection unit of the control unit shown in FIG. 5, according to an exemplary embodiment.
Figure 9:
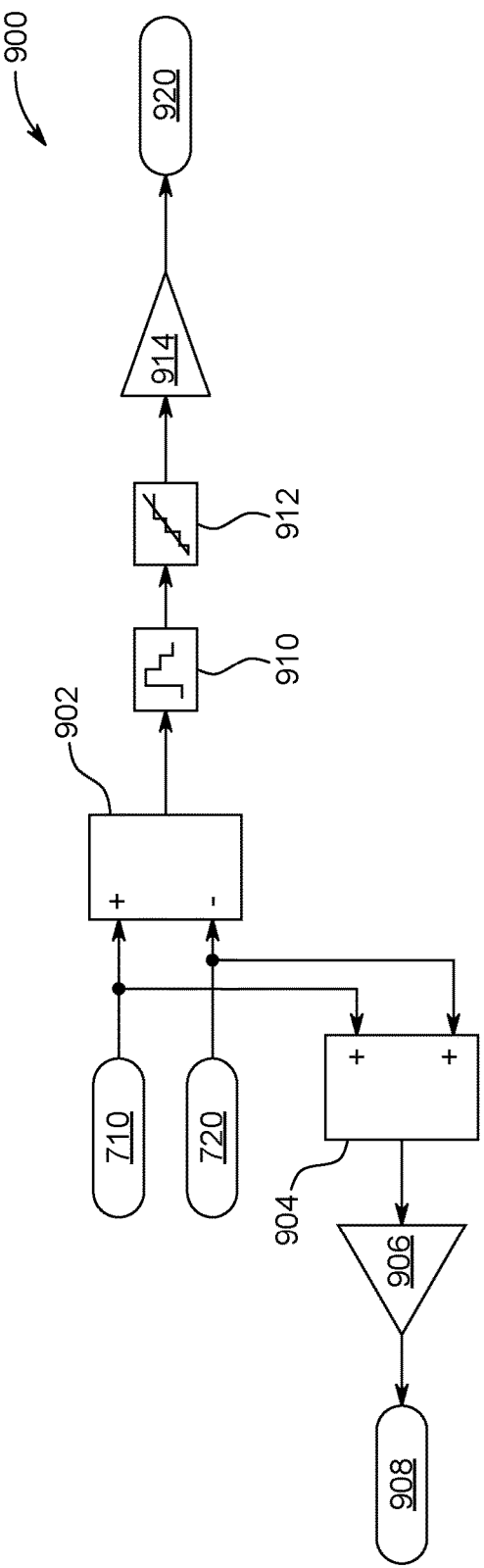
FIG. 9 is a schematic block diagram of an electrode signal conditioning unit of the control unit shown in FIG. 5, according to an exemplary embodiment.

FIGS. 5-16 illustrate control unit 300 of stimulation system 100, according to various exemplary embodiments. FIG. 5 is a schematic block diagram of control unit 300 of stimulation system 100 shown in FIG. 1, according to an exemplary embodiment. FIG. 6 is a schematic block diagram of signal processing unit 600 of control unit 300 shown in FIG. 5, according to an exemplary embodiment. FIG. 7 is a schematic block diagram of electrode multiplexer unit 700 of control unit 300 shown in FIG. 5, according to an exemplary embodiment. FIG. 8 is a schematic block diagram of electrode detection unit 800 of control unit 300 shown in FIG. 5, according to an exemplary embodiment. FIG. 9 is a schematic block diagram of electrode signal conditioning unit 900 of control unit 300 shown in FIG. 5, according to an exemplary embodiment.

Figure 10:
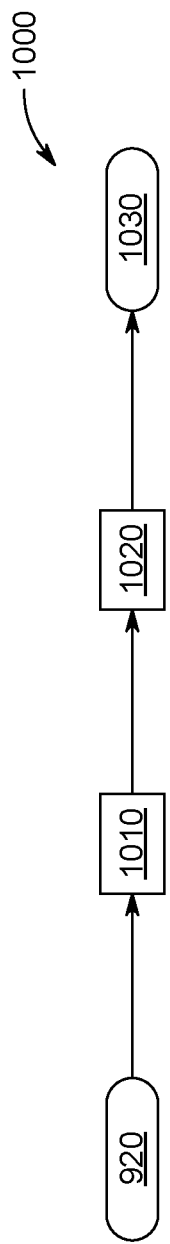
FIG. 10 is a schematic block diagram of a FFT unit of the control unit shown in FIG. 5, according to an exemplary embodiment.
Figure 11:
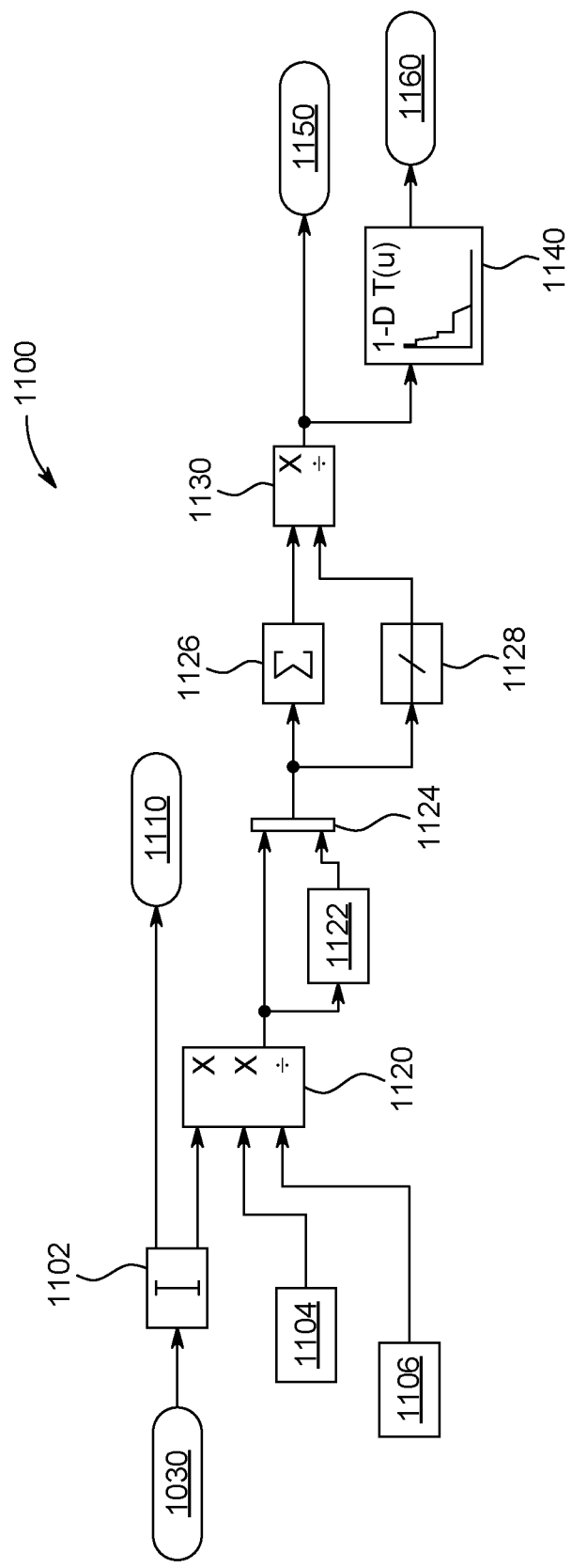
FIG. 11 is a schematic block diagram of a peak frequency unit of the control unit shown in FIG. 5, according to an exemplary embodiment.
Figure 12:
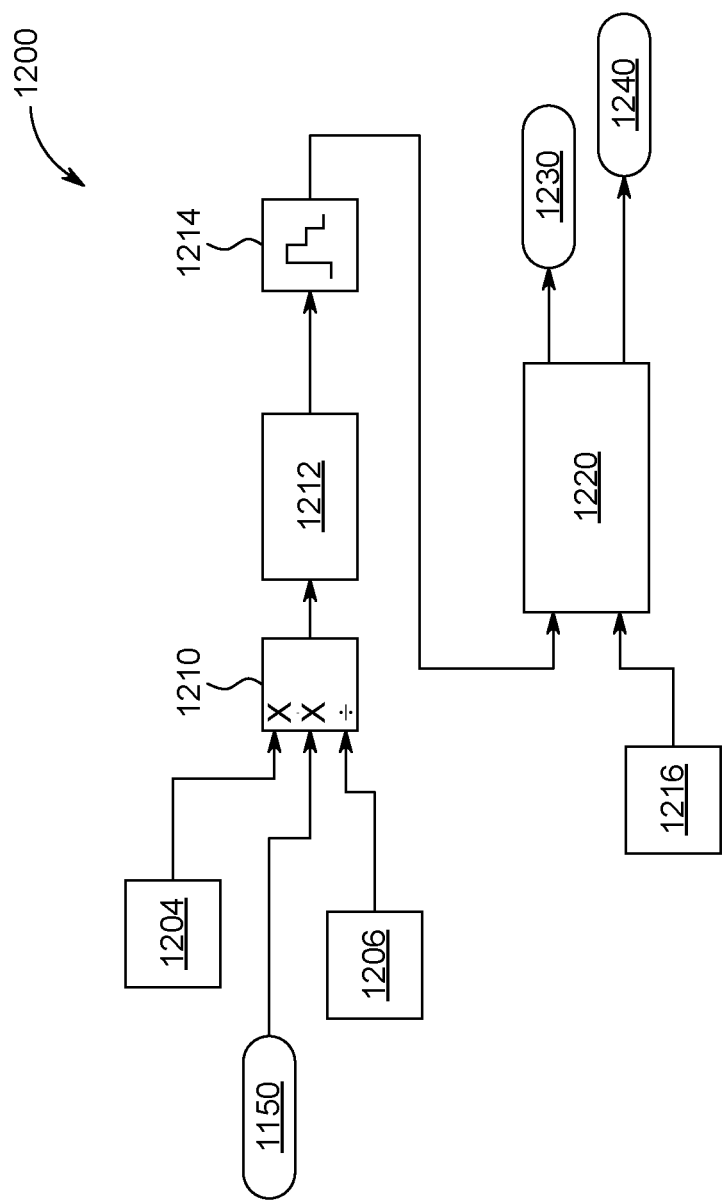
FIG. 12 is a schematic block diagram of an oscillator unit of the control unit shown in FIG. 5, according to an exemplary embodiment.

FIG. 10 is a schematic block diagram of FFT unit 1000 of control unit 300 shown in FIG. 5, according to an exemplary embodiment. FIG. 11 is a schematic block diagram of peak frequency unit 1100 of control unit 300 shown in FIG. 5, according to an exemplary embodiment. FIG. 12 is a schematic block diagram of oscillator unit 1200 of control unit 300 shown in FIG. 5, according to an exemplary embodiment.

Figure 13:
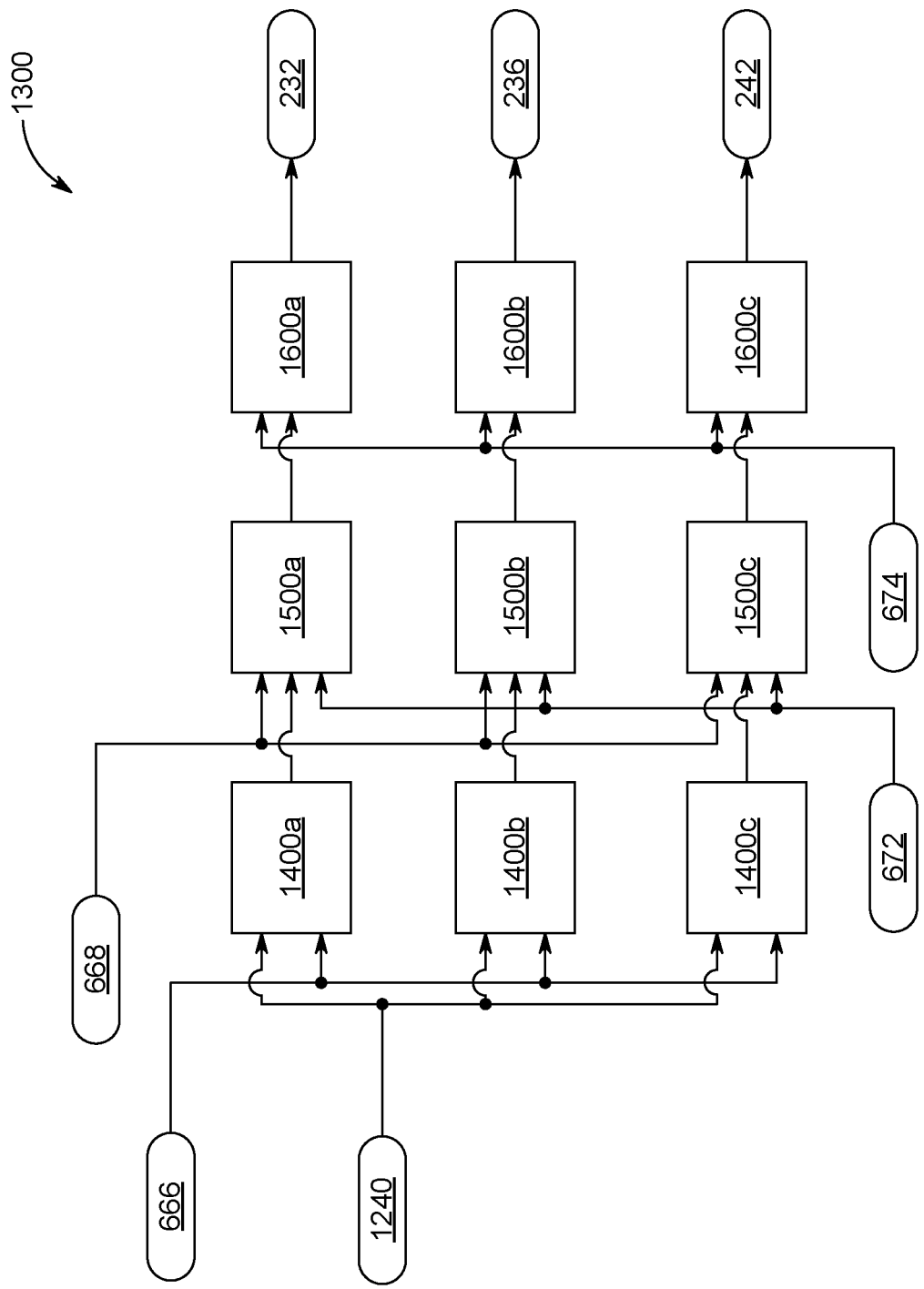
FIG. 13 is a schematic block diagram of a pulse shaping unit of the control unit shown in FIG. 5, according to an exemplary embodiment.
Figure 14:
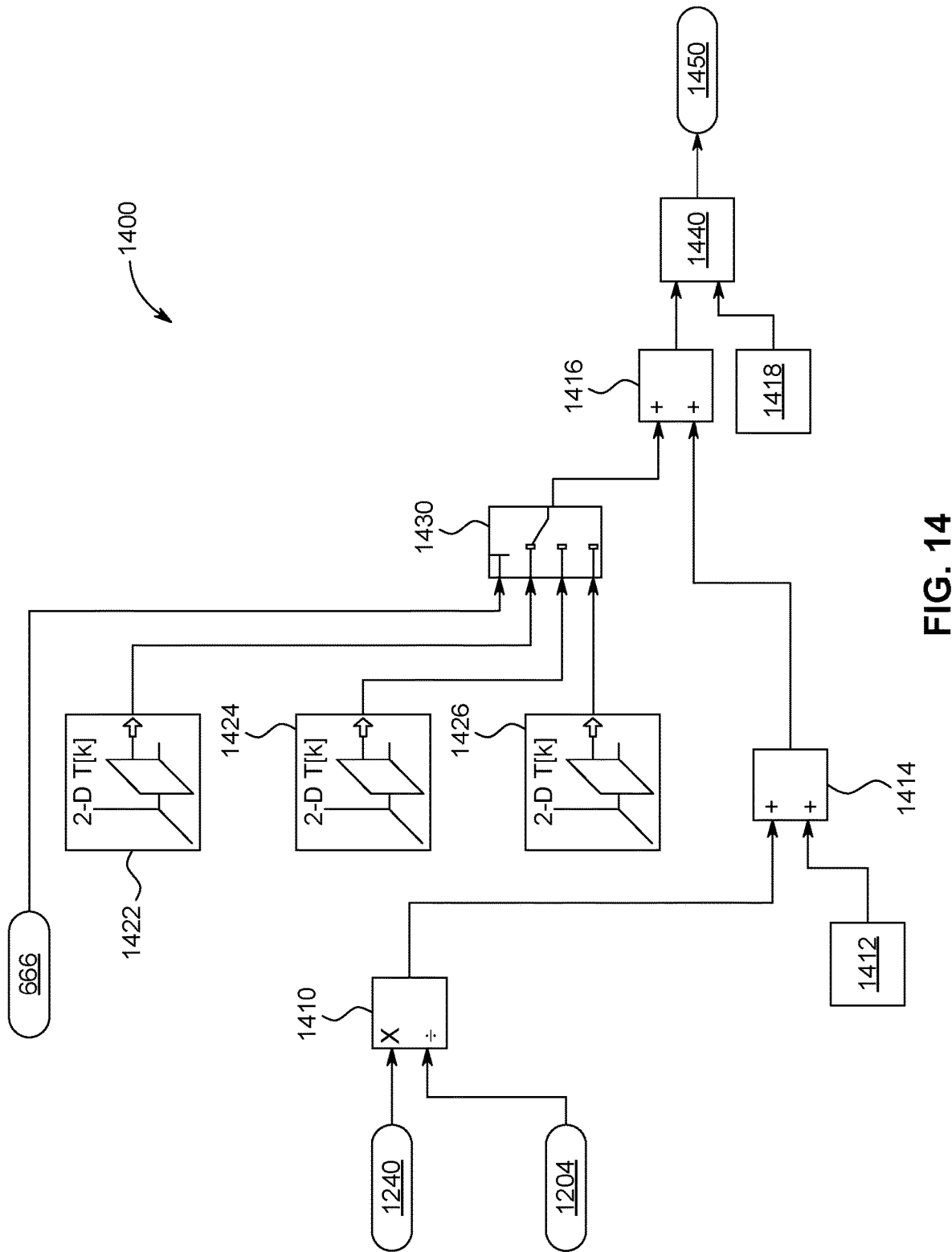
FIG. 14 is a schematic block diagram of a phase matrix unit of the control unit shown in FIG. 5, according to an exemplary embodiment.
Figure 15:
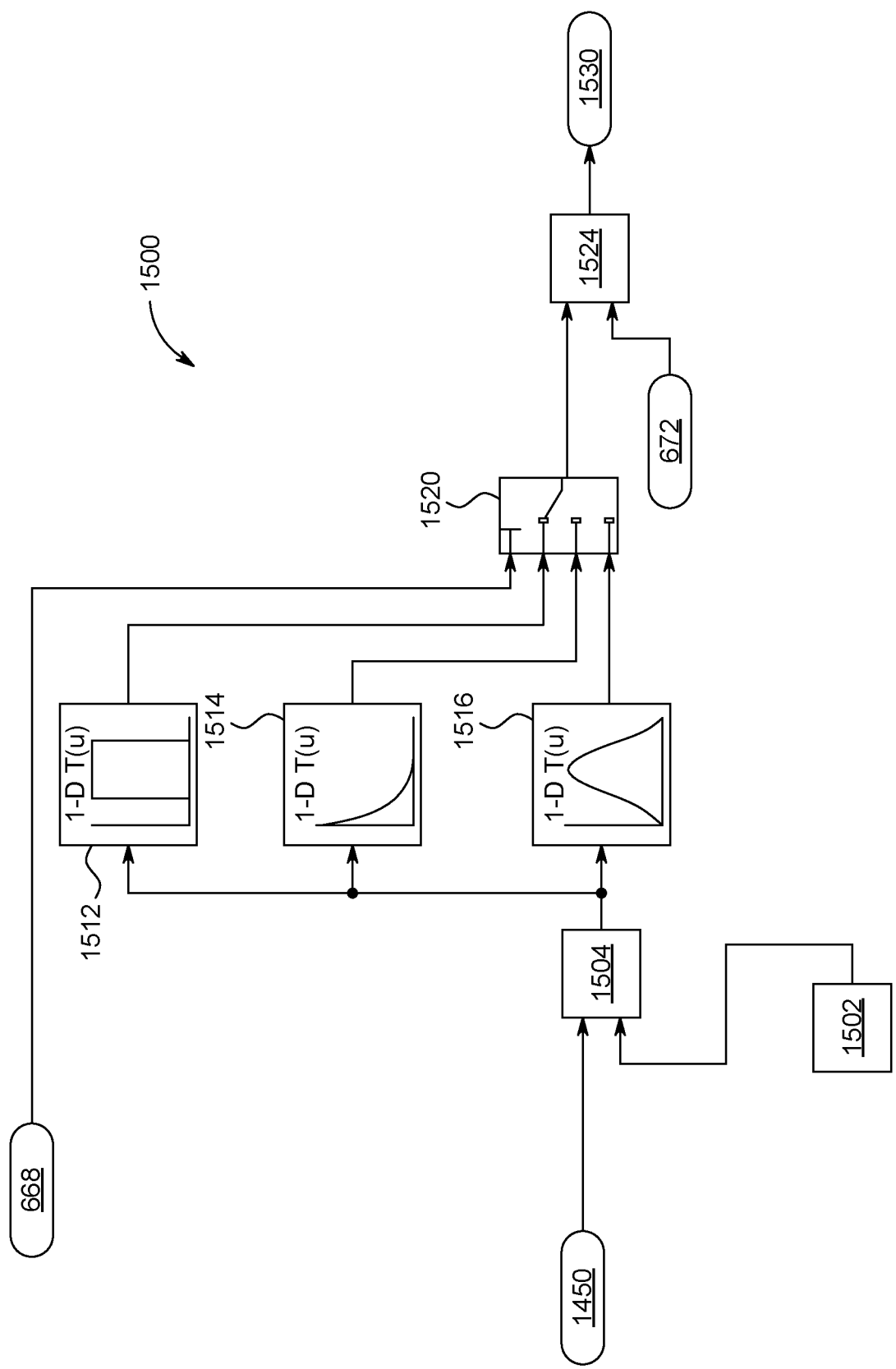
FIG. 15 is a schematic block diagram of a wave matrix unit of the control unit shown in FIG. 5, according to an exemplary embodiment.
Figure 16:
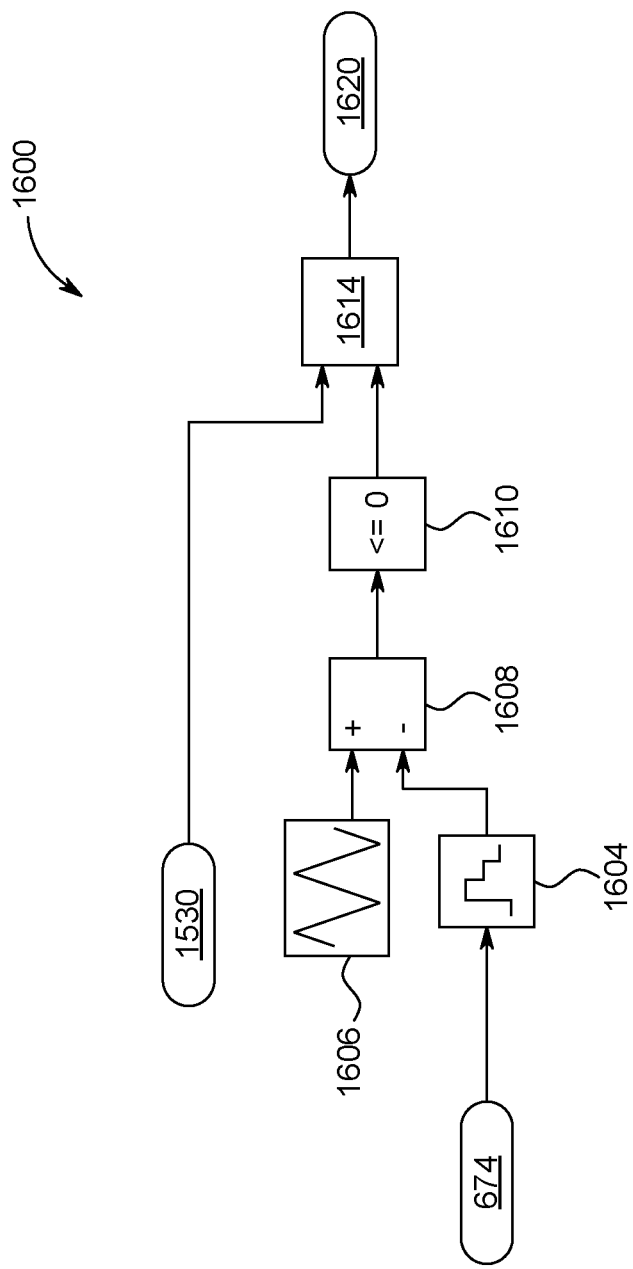
FIG. 16 is a schematic block diagram of a PWM unit of the control unit shown in FIG. 5, according to an exemplary embodiment.

FIG. 13 is a schematic block diagram of pulse shaping unit 1300 of control unit 300 shown in FIG. 5, according to an exemplary embodiment. FIG. 14 is a schematic block diagram of phase matrix unit 1400 of control unit 300 shown in FIG. 5, according to an exemplary embodiment. FIG. 15 is a schematic block diagram of wave matrix unit 1500 of control unit 300 shown in FIG. 5, according to an exemplary embodiment. FIG. 16 is a schematic block diagram of PWM unit 1600 of control unit 300 shown in FIG. 5, according to an exemplary embodiment.

Although control unit 300 is shown in FIG. 5 as a stand-alone apparatus and/or system, the embodiments of this disclosure can be used with other apparatuses and/or systems, such as, but not limited to, stimulation system 100, processor 170, smart phone 180, and/or stimulation apparatus 200. In some embodiments, control unit 300 can include signal processing unit 600, electrode multiplexer unit 700, electrode detection unit 800, electrode signal conditioning unit 900, FFT unit 1000, peak frequency unit 1100, oscillator unit 1200, pulse shaping unit 1300, phase matrix unit 1400, wave matrix unit 1500, and/or PWM unit 1600.

As shown in FIG. 5, control unit 300 can include circadian rhythm detector 302, wireless communication controller 304, biological synchronization controller 306, pulse modulation controller 308, first spatial wave controller 310, second spatial wave controller 320, voltage controller 330, voltage supply 340. Control unit 300 can be configured to control one or more emitter arrays (e.g., first and second light emitter arrays 232, 236 of headpiece 210, third light emitter array 242 of eyepiece 240, acoustic emitter array 252 of earpiece 250, fourth light emitter array 262 of nosepiece 260) of stimulation apparatus 200 based on measured EEG signals (e.g., local EEG signal 130, local EEG signal 140, global EEG signal 150) for treatment of a neurological abnormality of patient 102. Control unit 300 can be further configured to generate a sequence of optical macro pulses (e.g., macro pulse 1702 shown in FIG. 19, spatial wave 2000 shown in FIG. 20, spatial wave 2100 shown in FIG. 21), each having a defined shape, based on the measured EEG signals (e.g., local EEG signal 130, local EEG signal 140, global EEG signal 150).

As shown in FIG. 5, circadian rhythm detector 302 can be coupled to brain waves 110 of patient 102 measured by electrode array 220, tremor sensor 280, pulse sensor 282, temperature sensor 284, $SpO_2$ sensor 286, wireless communication controller 304, biological synchronization controller 306, and pulse modulation controller 308. Circadian rhythm detector 302 can be configured to determine an awake-sleep cycle of patient 102 based on the received brain waves 110 of patient 102 (e.g., alpha waves 112, beta waves 114, gamma waves 116, delta waves 118, theta waves 120) measured by electrode array 220 and send the determined awake-sleep cycle to wireless communication controller 304, biological synchronization controller 306, and/or pulse modulation controller 308. In some embodiments, circadian rhythm detector 302 can include brain state detector 640 and/or brain state filter tracking bank 650. For example, circadian rhythm detector 302 can determine the physical state of patient 102 (e.g., alpha state, gamma state, etc.) based on previous data of brain waves 110 of patient 102 and/or a library of brain wave 110 signatures (e.g., alpha waves 112, beta waves 114, gamma waves 116, delta waves 118, theta waves 120).

Wireless communication controller 304 can be coupled to transceiver 161, electrode array 220, tremor sensor 280, pulse sensor 282, temperature sensor 284, SpO$_2$ sensor 286, circadian rhythm detector 302, biological synchronization controller 306, pulse modulation controller 308, and voltage controller 330. Wireless communication controller 304 can be configured to transfer data and/or electrical signals to biological synchronization controller 306, pulse modulation controller 308, and voltage controller 330 based on received signals from transceiver 161, electrode array 220, tremor sensor 280, pulse sensor 282, temperature sensor 284, SpO$_2$ sensor 286, and circadian rhythm detector 302. In some embodiments, wireless communication controller 304 can communicate with processor 170, smart device 180, and/or stimulation apparatus 200. For example, wireless communication controller 304 can communicate wirelessly (e.g., RF, Bluetooth, WiFi, etc.) with transceiver 161 to receive and send data. In some embodiments, wireless communication controller 304 can include a control application (app) for control of various programs and/or stimulation routines. For example, the control application (app) can be utilized on smart device 180 and inputs and/or data can be sent to and from wireless communication controller 304.

Biological synchronization controller 306 can be coupled to electrode array 220 (e.g., brain waves 110 of patient 102), third light emitter array 242, acoustic emitter array 252, fourth light emitter array 262, circadian rhythm detector 302, wireless communication controller 304, pulse modulation controller 308, first spatial wave controller 310, and second spatial wave controller 320. Biological synchronization controller 306 can be configured to determine peak brain wave 110 frequencies of patient 102 received from electrode array 220 and synchronize with oscillator unit 1200 to control third light emitter array 242, acoustic emitter array 252, fourth light emitter array 262, first spatial wave controller 310, and/or second spatial wave controller 320. In some embodiments, peak brain wave 110 frequencies can be based on a FFT of the measured EEG signals. For example, FFT unit 1000 can convert measured EEG signals of electrode array 220 to peak frequencies. In some embodiments, biological synchronization controller 306 can include signal processing unit 600 shown in FIG. 6, electrode multiplexer unit 700 shown in FIG. 7, electrode detection unit 800 shown in FIG. 8, electrode signal conditioning unit 900 shown in FIG. 9, FFT unit 1000 shown in FIG. 10, peak frequency unit 1100 shown in FIG. 11, and/or oscillator unit 1200 shown in FIG. 12.

Pulse modulation controller 308 can be coupled to electrode array 220 (e.g., brain waves 110 of patient 102), third light emitter array 242, acoustic emitter array 252, fourth light emitter array 262, circadian rhythm detector 302, wireless communication controller 304, pulse modulation controller 308, first spatial wave controller 310, and second spatial wave controller 320. Pulse modulation controller 308 can be configured to modulate a pulse shape, a frequency, a pulse width, a duty cycle, an envelope, a time between sequential pulses, a time between sequential envelopes, and/or a gain based on EEG signals (e.g., local EEG signal 130, local EEG signal 140) from electrode array 220 and generate a pulse shape and/or a sequence of macro pulses to control third light emitter array 242, acoustic emitter array 252, fourth light emitter array 262, first spatial wave controller 310, and/or second spatial wave controller 320. In some embodiments, pulse modulation controller 308 can include pulse shaping unit 1300, phase matrix unit 1400, wave matrix unit 1500, and/or PWM unit 1600.

First spatial wave controller 310 can be coupled to first light emitter array 232, biological synchronization controller 306, and pulse modulation controller 308. First spatial wave controller 310 can be configured to receive data signals from biological synchronization controller 306 and pulse modulation controller 308 to generate a pulse shape and/or a sequence of macro pulses to control first light emitter array 232. In some embodiments, first spatial wave controller 310 can control first light emitter array 232 to generate radiation as a spatial moving wave of radiation based on the measured EEG signals (e.g., from electrode array 220). For example, first spatial wave controller 310 can control first light emitter array 232 (e.g., VIS wavelength, about 670 nm) to emit a spatial moving wave (e.g., similar to spatial wave 2000 shown in FIGS. 20A-20D and spatial wave 2100 shown in FIGS. 21A-21D). In some embodiments, first spatial wave controller 310 can include pulse shaping unit 1300, phase matrix unit 1400, wave matrix unit 1500, and/or PWM unit 1600.

Second spatial wave controller 320 can be coupled to second light emitter array 236, biological synchronization controller 306, and pulse modulation controller 308. Second spatial wave controller 320 can be configured to receive data signals from biological synchronization controller 306 and pulse modulation controller 308 to generate a pulse shape and/or a sequence of macro pulses to control second light emitter array 236. In some embodiments, second spatial wave controller 320 can control second light emitter array 236 to generate radiation as a spatial moving wave of radiation based on the measured EEG signals (e.g., from electrode array 220). For example, second spatial wave controller 320 can control second light emitter array 236 (e.g., NIR wavelength, about 850 nm) to emit a spatial moving wave (e.g., similar to spatial wave 2000 shown in FIGS. 20A-20D and spatial wave 2100 shown in FIGS. 21A-21D). In some embodiments, second spatial wave controller 320 can include pulse shaping unit 1300, phase matrix unit 1400, wave matrix unit 1500, and/or PWM unit 1600.

Voltage controller 330 can be coupled to first light emitter array 232, second light emitter array 236, third light emitter array 242, acoustic emitter array 252, fourth light emitter array 262, and wireless communication controller 304. Voltage controller 330 can be configured to provide power conditioning and voltage control to first light emitter array 232, second light emitter array 236, third light emitter array 242, acoustic emitter array 252, and/or fourth light emitter array 262 to emit radiation. In some embodiments, voltage controller 330 can include a DC-to-DC converter, for example, for an external voltage power source (e.g., 120 V outlet). In some embodiments, voltage controller 330 can receive voltage from a portable and/or rechargeable voltage source. For example, as shown in FIG. 5, voltage controller 330 can be coupled to battery 340 (e.g., rechargeable) for a portable stimulation system 100.

As shown in FIG. 6, signal processing unit 600 can include brain wave simulator 610, electrode multiplexer unit 700, electrode detection unit 800, electrode signal conditioning unit 900, FFT unit 1000, brain state detector 640, peak frequency unit 1100, brain state filter tracking bank 650, oscillator unit 1200, pulse shaping unit 1300, phase matrix unit 1400, and/or monitoring unit 690. Signal processing unit 600 can be configured to support biological synchronization controller 306 and sample measured EEG signals from electrode array 220 (e.g., from optimized first and second electrodes 224, 228) at a sampling rate (e.g., 500 Hz). Signal processing unit 600 can be further configured to convert the sampled EEG signals to a FFT (e.g., by FFT unit 1000) to produce an EEG frequency spectrum (e.g., at a real-time frame rate of 2.56 sec). Signal processing unit 600 can be further configured to analyze the produced EEG frequency spectrum to determine brain states of patient 102 (e.g., brain waves 110) and synchronize oscillator unit 1200 (e.g., NCO) to output peak (dominant) frequencies and amplitudes corresponding to each brain state of patient 102 (e.g., alpha waves 112, beta waves 114, gamma waves 116, delta waves 118, theta waves 120).

In some embodiments, signal processing unit 600 can generate synchronized outputs (e.g., from oscillator unit 1200) to first light emitter array 232, second light emitter array 236, third light emitter array 242, acoustic emitter array 252, fourth light emitter array 262, first spatial wave controller 310, and/or second spatial wave controller 320 based on the produced EEG frequency spectrum. In some embodiments, signal processing unit 600 can utilize predistortion (e.g., technique to improve linearity and reduce interference) of the 2D spatial wave phase matrix (e.g., spatial wave 2000 shown in FIG. 20) to ensure wave coherence at the applied penetration depth into patient 102. In some embodiments, signal processing unit 600 can be coupled to control unit 300, processor 170, and/or stimulation apparatus 200. For example, control unit 300 can include signal processing unit 600.

As shown in FIG. 6, brain wave simulator 610 can be coupled to summed (adder circuit) cycled brain states 602 and reference signal 604 (e.g., 1) to receive a brain state cycle signal. The brain state cycle signal can be outputted and summed (adder circuit) with reference signal 606 (e.g., 0) and sent to electrode multiplexer unit 700 and electrode detection unit 800. Electrode multiplexer unit 700 and electrode detection unit 800 can be coupled to first electrode input node 612 (channel select), second electrode input node 614 (channel select), electrode ground register 616, electrode test register 618, digital signal processor (DSP) 620, and/or electrode signal conditioning unit 900. Electrode multiplexer unit 700 and electrode detection unit 800 can be configured to sample measured EEG signals from electrode array 220 (e.g., from optimized first and second electrodes 224, 228). In some embodiments, electrode multiplexer unit 700, electrode detection unit 800, and electrode signal conditioning unit 900 can share a certain electrode signal (e.g., center electrode 770 of electrode array 220) to reduce noise.

Electrode signal conditioning unit 900 can be coupled to electrode multiplexer unit 700 and electrode detection unit 800 to receive first and second output nodes (EEG signals) and output sampled EEG signals to FFT unit 1000. Electrode signal conditioning unit 900 can be configured to condition the sampled EEG signals and convert the analog electrode signals to digital signals (e.g., via analog-to-digital converter). FFT unit 1000 can be coupled to electrode signal conditioning unit 900 to receive sampled EEG digital signals and output an EEG frequency spectrum to brain state detector 640 and peak frequency unit 1100. FFT unit 1000 can be configured to convert the sampled EEG signals to a FFT to produce an EEG frequency spectrum (e.g., at a real-time frame rate of 2.56 sec).

Brain state detector 640 and peak frequency unit 1100 can be coupled to FFT unit 1000 to receive the EEG frequency spectrum and output peak (dominant) frequencies and the detected brain state to monitoring unit 690, brain state filter tracking bank 650, and oscillator unit 1200. Brain state detector 640 and peak frequency unit 1100 can be configured to analyze the produced EEG frequency spectrum to determine brain states of patient 102 (e.g., brain waves 110) and synchronize oscillator unit 1200 (e.g., NCO) to output peak (dominant) frequencies and amplitudes corresponding to each brain state of patient 102 (e.g., alpha waves 112, beta waves 114, gamma waves 116, delta waves 118, theta waves 120).

Brain state filter tracking bank 650 can be coupled to biological synchronization controller 306, brain state detector 640, and peak frequency unit 1100 to receive the measured EEG signals from electrode array 220 and detected brain state of patient 102 to store the correlated data and compare the detected brain state to a library of brain states (e.g., brain waves 110) of patient 102 and output the filtered detected brain state to pulse shaping unit 1300 and phase matrix unit 1400. Oscillator unit 1200 can be coupled to brain state detector 640 and peak frequency unit 1100 to receive output peak (dominant) frequencies and amplitudes corresponding to each brain state of patient 102 (e.g., alpha waves 112, beta waves 114, gamma waves 116, delta waves 118, theta waves 120) and output peak (dominant) frequencies and amplitudes to pulse shaping unit 1300 and phase matrix unit 1400.

Pulse shaping unit 1300 and phase matrix unit 1400 can be coupled to brain state filter tracking bank 650, oscillator unit 1200 (phase input), spatial wave input 666, pulse shape input 668, gain input 672 (e.g., 1), and pulse width input 674 (e.g., 50% duty cycle) and output a spatial wave (e.g., similar to spatial wave 2000 shown in FIGS. 20A-20D and spatial wave 2100 shown in FIGS. 21A-21D) to first light emitter array viewer 680, second light emitter array viewer 682, third light emitter array viewer 684, and monitoring unit 690. Pulse shaping unit 1300 and phase matrix unit 1400 can be configured to control first light emitter array 232, second light emitter array 236, third light emitter array 242, acoustic emitter array 252, and/or fourth light emitter array 262 to generate radiation as a spatial moving wave of radiation (e.g., similar to spatial wave 2000 shown in FIGS. 20A-20D and spatial wave 2100 shown in FIGS. 21A-21D). In some embodiments, spatial wave input 666 can include a center-to-perimeter waveform, a side-to-side waveform, a front-to-back waveform, and/or a combination thereof. In some embodiments, pulse shape input 668 can include a raised cosine, an exponential, a square wave, and/or a combination thereof.

As shown in FIG. 7, electrode multiplexer unit 700 can include first demultiplexer 718, second demultiplexer 728, first electrode channels 730a-730j, second electrode channels 730k-730t, first multiplexer 740, second multiplexer 750, third demultiplexer 768, and fourth demultiplexer 778. Electrode multiplexer unit 700 can be configured to support biological synchronization controller 306 and sample measured EEG signals from electrode array 220 (e.g., from optimized first and second electrodes 224, 228) for a selected electrode matrix map of patient 102. In some embodiments, electrode multiplexer unit 700 can be coupled to control unit 300, processor 170, and/or stimulation apparatus 200. For example, control unit 300 can include electrode multiplexer unit 700.

First demultiplexer 718 can be coupled to electrode ground register 616 and first electrode channels 730a-730j. Second demultiplexer 728 can be coupled to electrode test register 618 and first electrode channels 730a-730j. First electrode channels 730a-730j can be coupled to first electrode input 710, DSP 620, and center electrode 770. First electrode input 710 can pass through selector switch 712 and voltage sensor 714 before being received by first electrode channels 730a-730j. DSP 620 can pass through selector switch 762 and voltage sensor 764 before being received by first electrode channels 730a-730j. Center electrode 770 (e.g., electrode in center of electrode array 220 of headpiece 210 shown in FIG. 2) can pass through selector switch 772 and voltage sensor 774 before being received by first electrode channels 730a-730j.

Third demultiplexer 768 can be coupled to electrode ground register 616 and second electrode channels 730k-730t. Fourth demultiplexer 778 can be coupled to electrode test register 618 and second electrode channels 730k-730t. Second electrode channels 730k-730t can be coupled to second electrode input 720, DSP 620, and center electrode 770. Second electrode input 720 can pass through selector switch 722 and voltage sensor 724 before being received by second electrode channels 730k-730t. DSP 620 can pass through selector switch 762 and voltage sensor 764 before being received by second electrode channels 730k-730t. Center electrode 770 (e.g., electrode in center of electrode array 220 of headpiece 210 shown in FIG. 2) can pass through selector switch 772 and voltage sensor 774 before being received by second electrode channels 730k-730t.

First multiplexer 740 can be coupled to first electrode input node 612, first electrode channels 730a-730j, and second electrode channels 730k-730t. Second multiplexer 750 can be coupled to second electrode input node 614, first electrode channels 730a-730j, and second electrode channels 730k-730t. First multiplexer 740 outputs first multiplexer electrode output 780 for first and second electrode channels 730a-730t based on first electrode input node 612 (channel select). Second multiplexer 750 outputs second multiplexer electrode output 790 for first and second electrode channels 730a-730t based on second electrode input node 614 (channel select).

As shown in FIG. 8, electrode detection unit 800 can include electrode 802 (e.g., similar to first electrode 224 shown in FIGS. 2 and 2A), resistor 804, voltage sensor 806, ground reference 808, first switch 810, second switch 820, gain amplifier 836, and anti-aliasing filter 838. Electrode detection unit 800 can be configured to support biological synchronization controller 306 and detect EEG signals (e.g., brain waves 110) of patient 102 from electrode array 220 for first and second electrode channels 730a-730t. In some embodiments, electrode detection unit 800 can be coupled to control unit 300, processor 170, and/or stimulation apparatus 200. For example, control unit 300 can include electrode detection unit 800.

Electrode 802 can be coupled to resistor 804 (current to voltage), voltage sensor 806, first switch 810, and second switch 820. First switch 810 can be controlled by center electrode 770 and electrode ground register 616 passed through selector switch 814. Second switch 820 can be controlled by DSP 620 and electrode test register 618 passed through selector switch 824. In some embodiments, first and second switches 810, 820 can test electrode 802 (e.g., first and second electrodes 224, 228) in electrode array 220 to be measured. For example, a test current can be injected into electrode 802 via activation of electrode test register 618 and electrode 802 can be grounded via activation of electrode ground register 616.

Voltage sensor 806 measures a voltage from selected electrode 802 (e.g., about 1-2 µV in amplitude) that is passed through selector switch 834 and input into gain amplifier 836. Gain amplifier 836 amplifies the voltage signal of electrode 802 by several orders of magnitude. In some embodiments, gain amplifier 836 can be a differential amplifier with a gain of about 128,000 (with negative input by center electrode 770). The amplified output from gain amplifier 836 is input into anti-aliasing filter 838 that increases a signal-to-noise ratio (SNR) of the signal and restricts the bandwidth of the signal before outputting sampled electrode output 840. In some embodiments, anti-aliasing filter 838 can include a $5^{th}$ order band pass filter of about 0.01 Hz to about 95 Hz and upper frequency out-of-band attenuation of about 100 dB.

As shown in FIG. 9, electrode signal conditioning unit 900 can include adder-subtractor circuit 902, adder circuit 904, averaging amplifier 906, analog ground signal 908, sampling circuit 910, analog-to-digital converter (ADC) 912, and gain amplifier 914. Electrode signal conditioning unit 900 can be configured to support biological synchronization controller 306 and receive the multiplexed sampled EEG signals from first and second multiplexers 740, 750 and condition and convert the analog electrode signals to digital signals (e.g., via analog-to-digital converter) to produce sampled filtered EEG output 920. In some embodiments, electrode signal conditioning unit 900 can be coupled to control unit 300, processor 170, and/or stimulation apparatus 200. For example, control unit 300 can include electrode signal conditioning unit 900.

First and second electrode inputs 710, 720 can be passed through adder-subtractor circuit 902 and input into sampling circuit 910 (e.g., at a 500 Hz sampling rate). Sampled signals can be input into ADC 912 (e.g., 16-bit converter, Vmin=−0.256, Vmax=0.256). Output from ADC 912 can be input into gain amplifier 914 to produce sampled filtered EEG output 920. In some embodiments, gain amplifier 914 can be a differential amplifier with a negative gain of about 50,000 (with negative input by analog ground signal 908) to provide a µV scale. First and second electrode inputs 710, 720 can be passed through adder circuit 904 and input to averaging amplifier (e.g., gain of 0.5) to produce analog ground signal 908. In some embodiments, analog ground signal 908 can be center electrode 770 and be used in electrode multiplexer unit 700 as a ground reference to selected electrodes of electrode array 220.

As shown in FIG. 10, FFT unit 1000 can include FFT converter 1010 and FFT spectrum generator 1020. FFT unit 1000 can be configured to support biological synchronization controller 306 and convert the sampled EEG signals to FFT signals to produce EEG frequency spectrum 1030. In some embodiments, FFT unit 1000 can be coupled to control unit 300, processor 170, and/or stimulation apparatus 200. For example, control unit 300 can include FFT unit 1000.

FFT converter 1010 can receive sampled filtered EEG output 920 and convert sampled filtered EEG output 920 to a FFT function, where the FFT function is defined for X and Y of length n:

$$Y(k) = \sum_{j=1}^{n} X(j) W_n^{-(j-1)(k-1)}, \text{ where } W_n = e^{(-2\pi i)/n} \text{ is one of n roots of unity.}$$

FFT converter 1010 can output each FFT function over time to FFT spectrum generator 1020 to produce EEG frequency spectrum 1030. In some embodiments, a sample rate can be about 200 Hz and a frame length can be about 512 samples that can produce a FFT transform every 2.56 sec (e.g., in real-time).

As shown in FIG. 11, peak frequency unit 1100 can include sorter 1102, first multiplier-divider circuit 1120, tapped delay 1122, vector concatenation circuit 1124, summer circuit 1126, divider circuit 1128, second multiplier-divider circuit 1130, and 1-dimensional (1D) lookup table 1140. Peak frequency unit 1100 can be configured to support biological synchronization controller 306 and analyze the produced EEG frequency spectrum 1030 to determine brain states of patient 102 (e.g., brain waves 110) and synchronize oscillator unit 1200 (e.g., NCO) to output peak (dominant) frequencies 1150 corresponding to each brain state of patient 102 (e.g., alpha waves 112, beta waves 114, gamma waves 116, delta waves 118, theta waves 120). In some embodiments, peak frequency unit 1100 can be coupled to control unit 300, processor 170, and/or stimulation apparatus 200. For example, control unit 300 can include peak frequency unit 1100.

Sorter 1102 can receive EEG frequency spectrum 1030 and determine a maximum (peak) frequency value 1110. In some embodiments, sorter 1102 can utilize a moving average of EEG frequency spectrum 1030 to determine a maximum value. In some embodiments, sorter 1102 can determined a peak frequency derived index that can be mapped onto 1D lookup table 1140 to determine brain state 1160. First multiplier-divider circuit 1120 can receive peak frequency value 1110, reference value 1104 (e.g., 100), and reference FFT length (e.g., 256) and pass the output through tapped delay 1122 and vector concatenation circuit 1124. Vector concatenation circuit 1124 can join the different (delayed) frequency bands (e.g., delta waves 118 of about 0.1-4 Hz, theta waves 120 of about 4-8 Hz, alpha waves 112 of about 8-12 Hz, beta waves 114 of about 12-30 Hz, gamma waves 116 of about 30-140 Hz) together and pass the output through summer circuit 1126 (e.g., sum of elements) and divider circuit 1128 (e.g., width). Summer circuit 1126 output and divider circuit 1128 output and input to second multiplier-divider circuit 1130 to determine peak frequency 1150. Peak frequency 1150 can also be sent to 1D lookup table 1140 to determined brain state 1160. In some embodiments, 1D lookup table 1140 can be part of brain state filter tracking bank 650 shown in FIG. 6. In some embodiments, brain state 1160 can be part of brain state detector 640 shown in FIG. 6.

As shown in FIG. 12, oscillator unit 1200 can include multiplier-divider circuit 1210, phase accumulator 1212, sampling circuit 1214, phase lookup table 1216, and oscillator 1220. Oscillator unit 1200 can be configured to support biological synchronization controller 306 and output peak (dominant) frequencies, phases, and amplitudes corresponding to each brain state of patient 102 (e.g., alpha waves 112, beta waves 114, gamma waves 116, delta waves 118, theta waves 120) to, for example, pulse shaping unit 1300 and/or phase matrix unit 1400. In some embodiments, oscillator unit 1200 can include a voltage controlled oscillator (VCO) or a numerically controlled oscillator (NCO). In some embodiments, oscillator unit 1200 can be coupled to control unit 300, processor 170, and/or stimulation apparatus 200. For example, control unit 300 can include oscillator unit 1200.

Multiplier-divider circuit 1210 can receive peak frequency 1150, reference phase value 1204 (e.g., 16-bit), reference clock frequency 1206 (e.g., 4 kHz) and pass the output to phase accumulator 1212 (e.g., 16-bit). Phase accumulator 1212 can accumulate the phase increment and pass the output to sampling circuit 1214 (e.g., based on 4 kHz reference clock frequency 1206). Sampling circuit 1214 can pass the phase increment to oscillator 1220 that also receives input from phase lookup table 1216 (e.g., finite set of entries). Oscillator 1220 can quantize the results of the phase increment and select corresponding values from phase lookup table 1216 and output sinusoidal waveform 1230 and phase 1240. In some embodiments, oscillator 1220 can include a NCO, for example, having optimized hardware description language (HDL), a latency of six cycles, and a frequency resolution of about 0.061 Hz. In some embodiments, phase lookup table 1216 can contain a finite set of values and, in its normal mode of operation, oscillator 1220 can allow phase accumulator 1212 numeric values to overflow and wrap around. In some embodiments, brain wave frequencies (e.g., brain waves 110) can be synthesized with high fidelity by selecting a frequency resolution $\Delta f=1/$ (sample time·$2^N$) Hz, where sample time is 1/(reference clock frequency 1206) and N is the phase accumulator 1212 word length. For example, phase accumulator 1212 word length N can be about 16 and reference clock frequency 1206 can be about 4 kHz, which corresponds to a frequency resolution of about 0.061 Hz.

As shown in FIG. 13, pulse shaping unit 1300 can include first phase matrix unit 1400a, second phase matrix unit 1400b, third phase matrix unit 1400c, first wave matrix unit 1500a, second wave matrix unit 1500b, third wave matrix unit 1500c, first PWM unit 1600a, second PWM unit 1600b, and third PWM unit 1600c. Pulse shaping unit 1300 can be configured to support pulse modulation controller 308, first spatial wave controller 310, and/or second spatial wave controller 320 and control a shape, a phase, and a pulse width of pulses and/or a sequence of macro pulses to first light emitter array 232, second light emitter array 236, third light emitter array 242, acoustic emitter array 252, and/or fourth light emitter array 262 to generate radiation as a spatial moving wave of radiation (e.g., similar to spatial wave 2000 shown in FIGS. 20A-20D and spatial wave 2100 shown in FIGS. 21A-21D). In some embodiments, pulse shaping unit 1300 can be coupled to control unit 300, processor 170, and/or stimulation apparatus 200. For example, control unit 300 can include pulse shaping unit 1300.

First, second, and third phase matrix units 1400a, 1400b, 1400c can receive spatial wave input 666 and phase 1240 and output phase matrices to respective first, second, and third wave matrix units 1500a, 1500b, 1500c. First, second, and third wave matrix units 1500a, 1500b, 1500c can receive phase matrices from first, second, and third phase matrix units 1400a, 1400b, 1400c, pulse shape input 668, and gain input 672 and output wave matrices to respective first, second, and third PWM units 1600a, 1600b, 1600c. First, second, and third PWM units 1600a, 1600b, 1600c can receive wave matrices from first, second, and third wave matrix units 1500a, 1500b, 1500c and pulse width input 674 and output PWM signals to respective first light emitter array 232, second light emitter array 236, and third light emitter array 242. In some embodiments, pulse shaping unit 1300 can output PWM signals to respective acoustic emitter array 252 and/or fourth light emitter array 262 to generate radiation as a spatial moving wave of radiation (e.g., similar to spatial wave 2000 shown in FIGS. 20A-20D and spatial wave 2100 shown in FIGS. 21A-21D). For example, PWM signals to acoustic emitter array 252 and/or fourth light emitter array 262 can be equivalent to third light emitter array 242 PWM signals.

In some embodiments, first, second, and third phase matrix units 1400a, 1400b, 1400c can control a 2-dimensional (2D) wave propagation direction. For example, first, second, and third phase matrix units 1400a, 1400b, 1400c can adjust a 2D wave propagation direction based on spatial wave input 666 (e.g., center-to-perimeter direction, a side-to-side direction, a front-to-back direction, a radial direction, an axial direction, a circumferential direction, a helical direction, a spiral direction, a circular direction, an elliptical direction, and/or a combination thereof). In some embodiments, first, second, and third wave matrix units 1500a, 1500b, 1500c can control a pulse envelope shape. For example, first, second, and third wave matrix units 1500a, 1500b, 1500c can adjust a shape of the envelope and a time between sequential envelopes based on pulse shape input 668 (e.g., a rectangular shape, a triangular shape, a Gaussian shape, a non-Gaussian shape, an exponential shape, a raised cosine-based shape, or a combination thereof) based on measured EEG signals. In some embodiments, first, second, and third PWM units 1600a, 1600b, 1600c can control a duty cycle modulation of discrete pulses within a pulse envelope. For example, first, second, and third PWM units 1600a, 1600b, 1600c can adjust a frequency and/or a duty cycle of a sequence of discrete pulses based on pulse width input 674 in order to reduce heating of tissues of patient 102. For example, first, second, and third PWM units 1600a, 1600b, 1600c can adjust a frequency and/or a duty cycle of a sequence of discrete pulses based on pulse width input 674 in order to control a penetration depth of the radiation into the patient's tissues As shown in FIG. 14, phase matrix unit 1400 can include multiplier-divider circuit 1410, first adder circuit 1414, second adder circuit 1416, first 2D phase matrix 1422, second 2D phase matrix 1424, third 2D phase matrix 1426, switch selector 1430, and modulo circuit 1440. Phase matrix unit 1400 can be configured to support pulse modulation controller 308, first spatial wave controller 310, and/or second spatial wave controller 320 and control a phase and a direction of propagation of pulses and/or a sequence of macro pulses to first light emitter array 232, second light emitter array 236, third light emitter array 242, acoustic emitter array 252, and/or fourth light emitter array 262 to generate radiation as a spatial moving wave of radiation (e.g., similar to spatial wave 2000 shown in FIGS. 20A-20D and spatial wave 2100 shown in FIGS. 21A-21D). In some embodiments, one or more spatial moving waves of radiation (e.g., similar to spatial wave 2000 shown in FIGS. 20A-20D and spatial wave 2100 shown in FIGS. 21A-21D) can change in time and be dynamically applied to individual emitters in first light emitter array 232, second light emitter array 236, third light emitter array 242, acoustic emitter array 252, and/or fourth light emitter array 262. For example, the spatial moving waves of radiation can be synchronously changing in time. For example, the spatial moving waves of radiation can be independently changing in time. In some embodiments, phase matrix unit 1400 can be coupled to control unit 300, processor 170, and/or stimulation apparatus 200. For example, control unit 300 can include phase matrix unit 1400.

Multiplier-divider circuit 1410 can receive phase 1240 and reference phase value 1204 (e.g., 16-bit) and pass the output to first adder circuit 1414. First adder circuit 1414 can sum the output from multiplier-divider circuit 1410 and reference value 1412 and pass the output to second adder circuit 1416. Switch selector 1430 can receive and select first 2D phase matrix 1422, second 2D phase matrix 1424, or third 2D phase matrix 1426 based on spatial wave input 666 and pass the output to second adder circuit 1416. Second adder circuit 1416 can sum the output from switch selector 1430 and first adder circuit 1414 and pass the output to modulo circuit 1440. Modulo circuit 1440 can receive output from second adder circuit 1416 and second reference value 1418 to output phase matrix 1450. In some embodiments, modulo circuit 1440 accounts for phase wrapping by modulo operating the synthesized phase with the pattern period.

As shown in FIG. 15, wave matrix unit 1500 can include first multiplier circuit 1504, first 1D wave matrix 1512, second 1D wave matrix 1514, third 1D wave matrix 1516, switch selector 1520, and second multiplier circuit 1524. Wave matrix unit 1500 can be configured to support pulse modulation controller 308, first spatial wave controller 310, and/or second spatial wave controller 320 and control a waveform of pulses and/or a sequence of macro pulses to first light emitter array 232, second light emitter array 236, third light emitter array 242, acoustic emitter array 252, and/or fourth light emitter array 262 to generate radiation as a spatial moving wave of radiation (e.g., similar to spatial wave 2000 shown in FIGS. 20A-20D and spatial wave 2100 shown in FIGS. 21A-21D). In some embodiments, wave matrix unit 1500 can be coupled to control unit 300, processor 170, and/or stimulation apparatus 200. For example, control unit 300 can include wave matrix unit 1500.

First multiplier circuit 1504 can receive phase matrix 1450 and reference phase value 1502 (e.g., 8-bit) and pass the output to first 1D wave matrix 1512, second 1D wave matrix 1514, and third 1D wave matrix 1516. Switch selector 1520 can receive and select first 1D wave matrix 1512, second 1D wave matrix 1514, and third 1D wave matrix 1516 based on pulse shape input 668 and pass the output to second multiplier circuit 1524. Second multiplier circuit 1524 can receive the output from switch selector 1520 and gain input 672 to amplify the signal and output wave matrix 1530.

In some embodiments, wave matrix unit 1500 can utilize a pulse shape lookup table based on phase matrix 1450. For example, the pulse shape lookup table can include a rectangular shape, a triangular shape, a Gaussian shape, a non-Gaussian shape, an exponential shape, a raised cosine-based shape, a combination thereof, or any other envelope shape. In some embodiments, pulse shape input 668 can control a pulse shape of the envelope. For example, pulse shape input 668 can select a rectangular shape, a triangular shape, a Gaussian shape, a non-Gaussian shape, an exponential shape, a raised cosine-based shape, or a combination thereof. In some embodiments, gain input 672 can control a peak pulse amplitude of the envelope.

As shown in FIG. 16, PWM unit 1600 can include sampling circuit 1604, waveform circuit 1606, adder-subtractor circuit 1608, filter 1610, and multiplier 1614. PWM unit 1600 can be configured to support pulse modulation controller 308, first spatial wave controller 310, and/or second spatial wave controller 320 and discretize wave matrix 1530 into a sequence of PWM filling pulses (e.g., similar to PWM filling pulses 1702a, 1702b, 1702c of macro pulse 1702 shown in FIG. 19) that can follow the shape and the envelope of the spatial wave (e.g., similar to spatial wave 2000 shown in FIGS. 20A-20D and spatial wave 2100 shown in FIGS. 21A-21D). In some embodiments, PWM unit 1600 can be coupled to control unit 300, processor 170, and/or stimulation apparatus 200. For example, control unit 300 can include PWM unit 1600. In some embodiments, wave matrix 1530 can include PWM filling pulses to allow for higher intensities and thereby deeper penetration depths (e.g., about 40 mm) with reduced heating to patient 102 (e.g., lower than about 102° F.).

Adder-subtractor circuit 1608 can receive pulse width input 674 passed through sampling circuit 1604 and reference waveform (e.g., a triangular wave) from waveform circuit 1606 and pass the output to filter 1610 (e.g., less than or equal to 0). Multiplier 1614 can receive the output from filter 1610 and wave matrix 1530 (e.g., amplitude) to discretize wave matrix 1530 and output PWM filling pulses 1620. In some embodiments, pulse width input 674 can include a duty cycle of 0%, 25%, 50%, 75%, and/or 100%.

Exemplary Pulsed (PWM) Waveform

Figure 17:
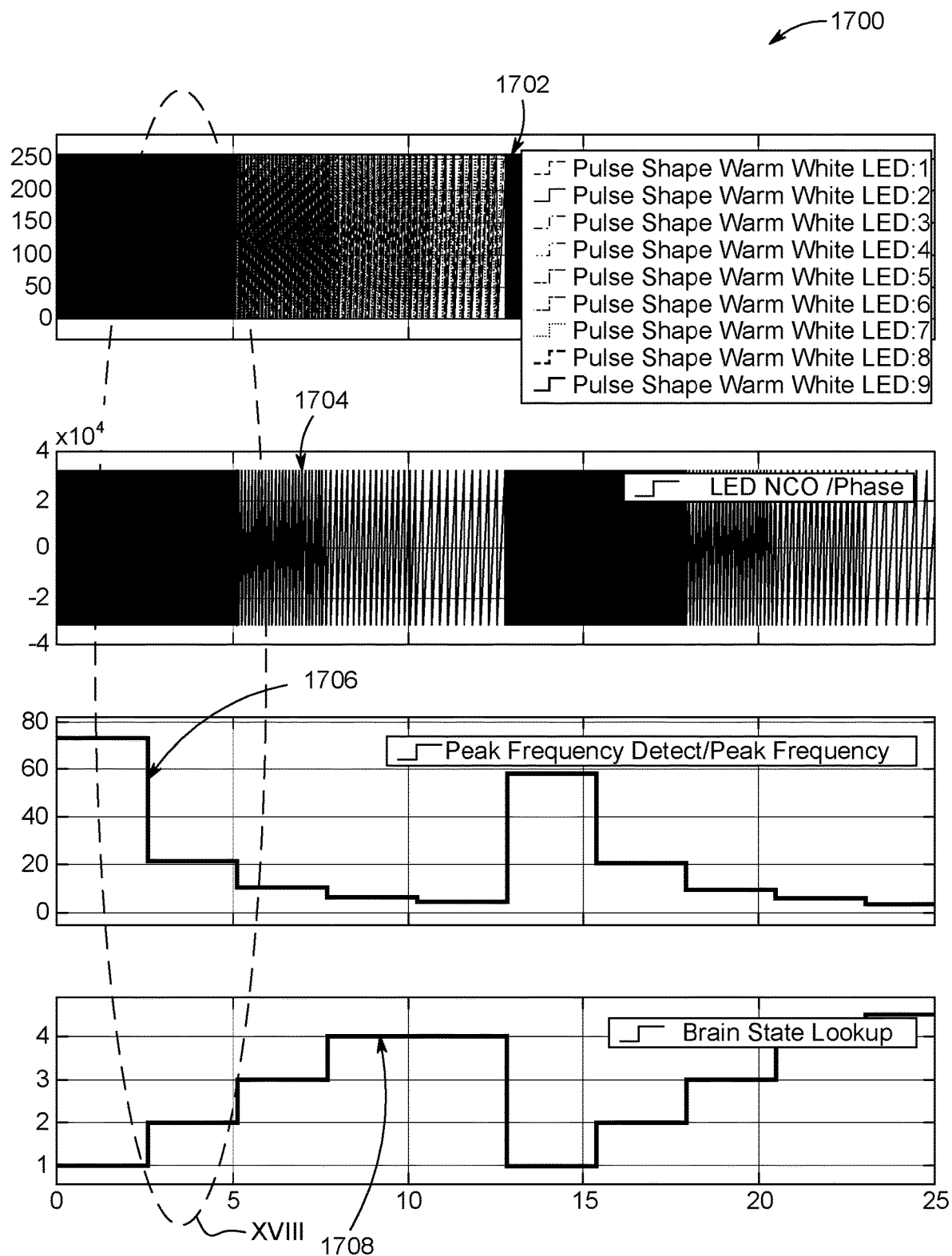
FIG. 17 is a schematic illustration of a pulsed (PWM) waveform of a pulsed emitter array, according to an exemplary embodiment.
Figure 18:
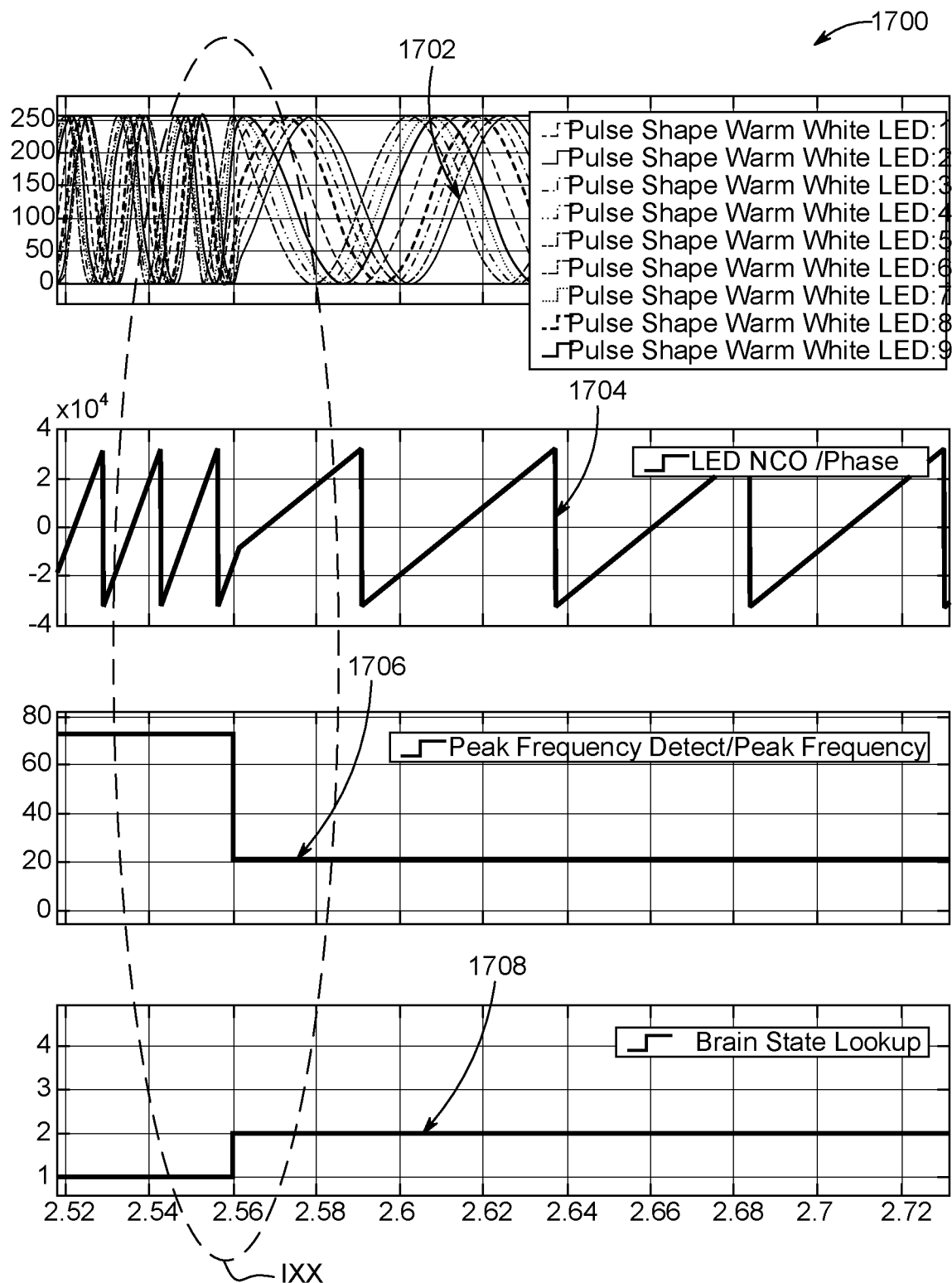
FIG. 18 is an enhanced view of the pulsed (PWM) waveform shown in FIG. 17, according to an exemplary embodiment.

FIGS. 17-19 illustrate pulsed (PWM) waveform 1700, according to various exemplary embodiments. FIG. 17 is a schematic illustration of pulsed (PWM) waveform 1700 of a pulsed emitter array (e.g., third light emitter array 242) of stimulation apparatus 200, according to an exemplary embodiment. FIG. 18 is an enhanced view of pulsed (PWM) waveform 1700 (denoted by dashed ellipse - - - XVIII - - - in FIG. 17) shown in FIG. 17, according to an exemplary embodiment. FIG. 19 is an enhanced view of pulsed (PWM) waveform 1700 (denoted by dashed ellipse - - - IXX - - - in FIG. 18) shown in FIG. 18, according to an exemplary embodiment.

Although pulsed (PWM) waveform 1700 is shown in FIGS. 17-19 as a stand-alone waveform and/or system, the embodiments of this disclosure can be used with other apparatuses and/or systems, such as, but not limited to, stimulation system 100, processor 170, smart phone 180, stimulation apparatus 200, electrode array 220, first light emitter array 232, second light emitter array 236, third light emitter array 242, acoustic emitter array 252, and/or fourth light emitter array 262.

As shown in FIGS. 17-19, pulsed (PWM) waveform 1700 can include macro pulse 1702, oscillator phase 1704, peak frequency 1706, and brain state 1708. In some embodiments, macro pulse 1702 can be based on PWM filling pulses 1620 that are based on pulse shape input 668 and wave matrix 1530. For example, as shown in FIG. 17, macro pulse 1702 can be based on a raised cosine (e.g., selected by pulse shape input 668). In some embodiments, macro pulse 1702 can include PWM filling pulses. For example, as shown in FIG. 19, macro pulse 1702 can include PWM filling pulses 1702a, 1702b, 1702c. In some embodiments, oscillator phase 1704 can be based on phase 1240 from oscillator unit 1200. For example, as shown in FIG. 17, oscillator phase 1704 can change for each different detected peak frequency 1706.

In some embodiments, peak frequency 1706 can be based on peak frequencies 1150 from peak frequency unit 1100. For example, peak frequency 1706 can correspond to a maximum value for a given brain state 1708 (e.g., gamma waves 116, beta waves 114, alpha waves 112, theta waves 120, delta waves 118). In some embodiments, brain state 1708 can be based on output from brain state detector 640. For example, brain state 1708 can be based on measured EEG signals from brain waves 110 of patient 102 and a brain state lookup table (e.g., brain state filter tracking bank 650). In some embodiments, pulsed (PWM) waveform 1700 can be applied in a pulsed emitter array of stimulation apparatus 200. For example, as shown in FIGS. 17-19, pulsed (PWM) waveform 1700 can be applied in third light emitter array 242 (e.g., broadband warm white light) as a 3×3 light emitter array with a raised cosine pulse shape.

Exemplary Spatial Waves

FIGS. 20A-20D and 21A-21D illustrate spatial waves 2000, 2100, according to various exemplary embodiments. FIGS. 20A-20D are a schematic illustration of spatial wave 2000 of a pulsed emitter array (e.g., first light emitter array 232) of stimulation apparatus 200 over increments of π/4, according to an exemplary embodiment. FIGS. 21A-21D are a schematic illustration of spatial wave 2100 of a pulsed emitter array (e.g., first light emitter array 232) of stimulation apparatus 200 over increments of π/4, according to an exemplary embodiment.

Although spatial waves 2000, 2100 are shown in FIGS. 20A-20D and 21A-21D as stand-alone waves and/or systems, the embodiments of this disclosure can be used with other apparatuses and/or systems, such as, but not limited to, stimulation system 100, processor 170, smart phone 180, stimulation apparatus 200, electrode array 220, first light emitter array 232, second light emitter array 236, third light emitter array 242, acoustic emitter array 252, and/or fourth light emitter array 262.

As shown in FIGS. 20A-20D, spatial wave 2000 can include π/4 phase increments 2000A-2000D. Spatial wave 2000 can be based on phase matrix 1450 and wave matrix 1530. In some embodiments, spatial wave 2000 can include a moving wave of emission that changes over time based on the selected phase (e.g., phase matrix 1450) and pulse shape (e.g., wave matrix 1530). For example, as shown in FIGS. 20A-20D representing π/4 phase increments 2000A-2000D, spatial wave 2000 can change (propagate) over time based on phase matrix 1450 having a center-to-perimeter propagation phase and wave matrix 1530 having a raised cosine-based shape. In some embodiments, spatial wave 2000 can be applied in a pulsed emitter array of stimulation apparatus 200. For example, as shown in FIGS. 20A-20D, spatial wave 2000 can be applied in first light emitter array 232 (e.g., VIS wavelength, about 670 nm) as a 16×16 light emitter array with a center-to-perimeter propagation and a raised cosine-based shape.

As shown in FIGS. 21A-21D, spatial wave 2100 can include π/4 phase increments 2100A-2100D. Spatial wave 2100 can be based on phase matrix 1450 and wave matrix 1530. In some embodiments, spatial wave 2100 can include a moving wave of emission that changes over time based on the selected phase (e.g., phase matrix 1450) and pulse shape (e.g., wave matrix 1530). For example, as shown in FIGS. 21A-21D representing π/4 phase increments 2100A-2100D, spatial wave 2100 can change (propagate) over time based on phase matrix 1450 having a side-to-side propagation phase and wave matrix 1530 having a sinusoidal shape. In some embodiments, spatial wave 2100 can be applied in a pulsed emitter array of stimulation apparatus 200. For example, as shown in FIGS. 21A-21D, spatial wave 2100 can be applied in first light emitter array 232 (e.g., VIS wavelength, about 670 nm) as a 16×16 light emitter array with a side-to-side propagation and a sinusoidal shape.

Exemplary Treatment Flow Diagram

Figure 22:
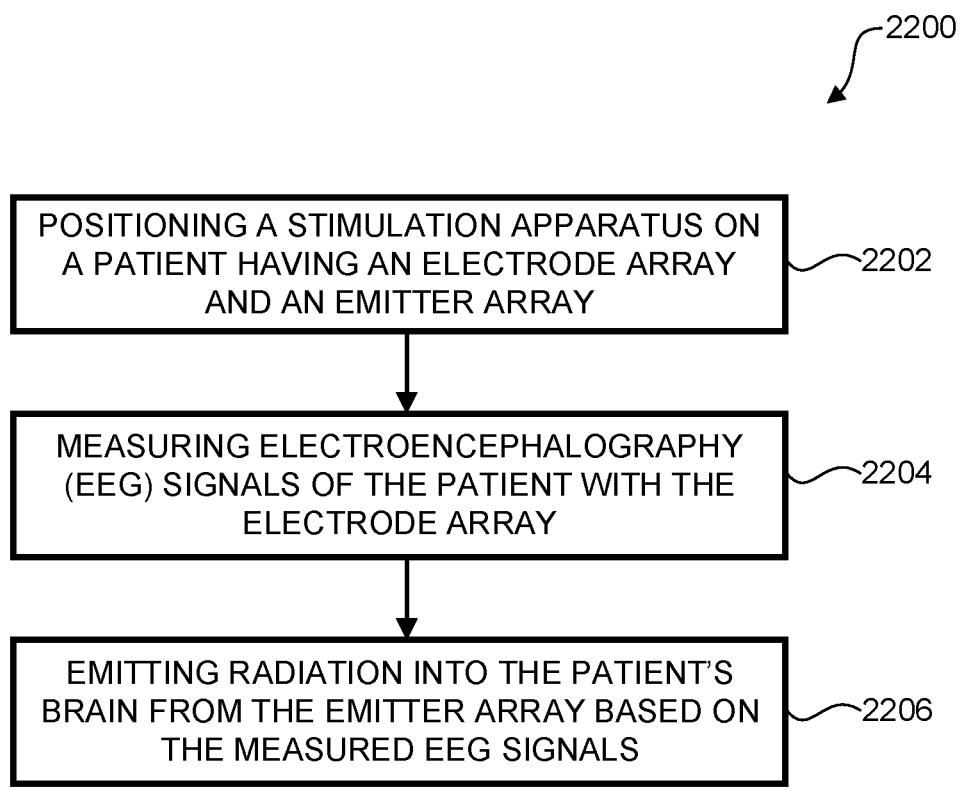
FIG. 22 illustrates a flow diagram for treatment of a neurological abnormality, according to an exemplary embodiment.

FIG. 22 illustrates treatment flow diagram 2200 for treatment of a neurological abnormality, according to an exemplary embodiment. It is to be appreciated that not all steps in FIG. 22 are needed to perform the disclosure provided herein. Further, some of the steps can be performed simultaneously, sequentially, and/or in a different order than shown in FIG. 22. Treatment flow diagram 2200 shall be described with reference to FIGS. 1-5, 17-19, 20A-20D, and 21A-21D. However, treatment flow diagram 2200 is not limited to those example embodiments.

In step 2202, as shown in the example of FIGS. 1 and 2, stimulation apparatus 200 of stimulation system 100 can be positioned on patient 102, where stimulation apparatus 200 includes electrode array 220, first light emitter array 232, second light emitter array 236, third light emitter array 242, acoustic emitter array 252, and/or fourth light emitter array 262.

In step 2204, as shown in the example of FIGS. 1, 2, and 5, electrode array 220 can measure EEG signals (e.g., brain waves 110) of patient 102. In some embodiments, the measuring can include measuring a local EEG signal obtained from an electrode in electrode array 220. For example, as shown in FIGS. 1 and 2, local EEG signal 130 can be obtained from first electrode 224 of first electrode array 222. In some embodiments, the measuring includes measuring a global synthesized EEG signal obtained from a combination of local EEG signals obtained from electrodes in electrode array 220. For example, as shown in FIGS. 1 and 2, global synthesized EEG signal 150 can be obtained from first and second local EEG signals 130, 140 from first and second electrode arrays 222, 226, respectively. In some embodiments, the measuring can include individually taking measurements of each electrode in electrode array 220. For example, as shown in FIGS. 2 and 5, measurements can be taken individually from first and second electrodes 224, 228. In some embodiments, the measuring can include individually controlling each electrode in electrode array 220. For example, as shown in FIGS. 2 and 5, first and second electrodes 224, 228 can be individually controlled.

In some embodiments, treatment flow diagram 2200 can further include filtering a global synthesized EEG signal in a pre-determined frequency range. For example, global synthesized EEG signal 150 can be filtered in a gamma wave 116 range of about 30-140 Hz. In some embodiments, treatment flow diagram 2200 can further include filtering a global synthesized EEG signal by a specific signal processing algorithm. For example, global synthesized EEG signal 150 can be filtered by a fast Fourier transform (FFT) algorithm, a discrete Fourier transform (DFT) algorithm, a Goertzel algorithm, a Bluestein's algorithm, a Cooley-Tukey algorithm, a Rader's algorithm, a fractional Fourier transform (FRFT) algorithm, a finite impulse response (FIR) algorithm, an infinite impulse response (IIR) algorithm, an adaptive filter algorithm, a Wiener filter algorithm, a Kalman filter algorithm, or a combination thereof. In some embodiments, treatment flow diagram 2200 can further include measuring tremors, pulse, temperature, and/or $SpO_2$ of patient 102 with a sensor affixed to patient 102. For example, as shown in FIG. 1, stimulation system 100 can include tremor sensor 280, pulse sensor 282, temperature sensor 284, and $SpO_2$ sensor 286.

In step 2206, as shown in the example of FIGS. 1, 2, 5, 17-19, 20A-20D, 21A-21D, first light emitter array 232, second light emitter array 236, third light emitter array 242, acoustic emitter array 252, and/or fourth light emitter array 262 can emit radiation into the brain of patient 102 based on the measured EEG signals for treatment of a neurological abnormality. In some embodiments, the emitting includes emitting a sequence of optical macro pulses (e.g., macro pulse 1702), each having a defined shape, based on the measured EEG signals. For example, macro pulse 1702 can have an envelope and can be composed of a sequence of PWM fillings pulses 1702a, 1702b, 1702c, etc.

In some embodiments, the emitting includes individually controlling each emitter in the emitter array. For example, as shown in FIGS. 2 and 5, first light emitter 234, second light emitter 238, third light emitter 244, acoustic emitter 254, and/or fourth light emitter 264 can be individually controlled. In some embodiments, the emitting includes uniform emission for all emitters in the emitter array. For example, as shown in FIGS. 2 and 17-19, each third light emitter 244 of third light emitter array 242 can emit radiation of the same intensity and frequency (e.g., warm white light). In some embodiments, the emitting includes static emission based on different emissions from different emitters in the emitter array. For example, as shown in FIG. 2, first and second light emitter arrays 232, 236 can emit static emission from first light emitter 234 (e.g., VIS wavelength, about 670 nm) and second light emitter 238 (e.g., NIR wavelength, about 850 nm) of different intensities.

In some embodiments, treatment flow diagram 2200 can further include determining an awake-sleep cycle of patient 102 based on measured EEG signals from electrode array 220. For example, as shown in FIG. 5, circadian rhythm detector 302 can determined the awake-sleep cycle of patient 102. In some embodiments, treatment flow diagram 2200 can further include adjusting a pulse shape of emitted radiation based on a determined awake-sleep cycle in an awake configuration and/or in a sleep configuration. For example, as shown in FIGS. 3, 4, and 17-19, macro pulse 1702 can be adjusted by pulse shape input 668 during awake configuration 10 and/or during sleep configuration 20. In some embodiments, treatment flow diagram 2200 can treat amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

In some embodiments, treatment flow diagram 2200 can further include increasing mitochondria activity on a brain outer periphery of patient 102 via stimulation system 100. For example, mitochondria activity can be measured by a lower alpha synuclein in the blood stream or tear duct of patient 102. In some embodiments, treatment flow diagram 2200 can further include increasing oxygenation of patient 102 via stimulation system 100. For example, oxygenation of patient 102 can be monitored by $SpO_2$ sensor 286. In some embodiments, treatment flow diagram 2200 can further include stimulating stem cell swarms (growth) via stimulation system 100. For example, stem cell swarms can be measured by DaTscan (DAT) and/or magnetic resonance imaging (MRI) to assess dopamine containing neurons. In some embodiments, treatment flow diagram 2200 can further include increasing neuroplasticity in the substantia nigra growth and/or outer brain gray matter via stimulation system 100. For example, neuroplasticity can be measured by DAT and/or MRI. In some embodiments, treatment flow diagram 2200 can further include reducing tremors via stimulation system 100. For example, tremors of patient 102 can be monitored by tremor sensor 280. In some embodiments, treatment flow diagram 2200 can further include increasing fine motor skills via stimulation system 100. For example, fine motor skills can be measured by the Unified Parkinson's Disease Rating Scale (UPDRS). In some embodiments, treatment flow diagram 2200 can further include stimulating glial cell production via stimulation system 100. For example, glial cell production can be measured by a decrease in amyloid beta plaque the brain of patient 102 and/or alpha synuclein in the blood stream and/or tear duct of patient 102.

Exemplary Optimized Treatment Flow Diagram

Figure 23:
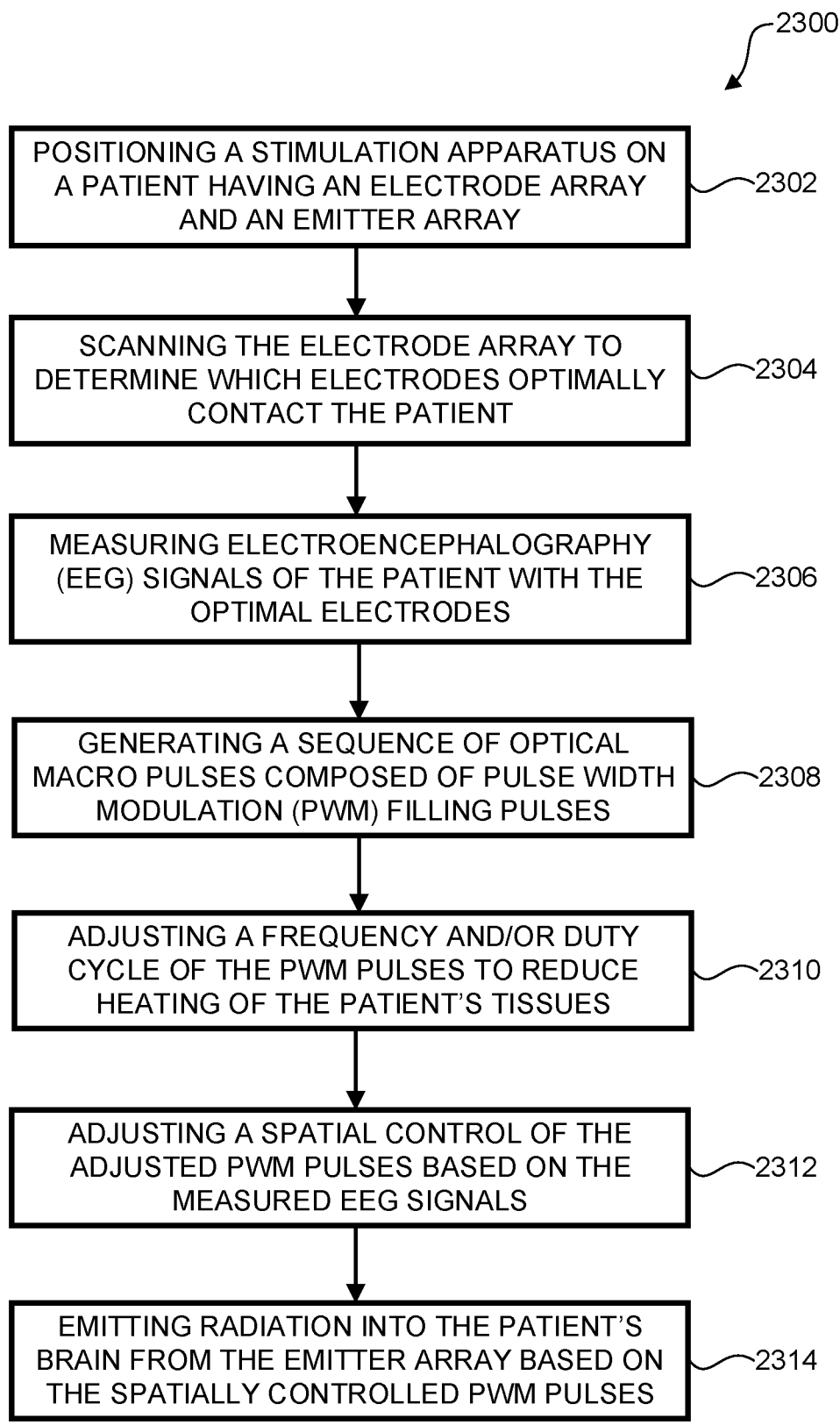
FIG. 23 illustrates a flow diagram for treatment of a neurological abnormality, according to an exemplary embodiment.

FIG. 23 illustrates optimized treatment flow diagram 2300 for optimized treatment of a neurological abnormality, according to an exemplary embodiment. It is to be appreciated that not all steps in FIG. 23 are needed to perform the disclosure provided herein. Further, some of the steps can be performed simultaneously, sequentially, and/or in a different order than shown in FIG. 23. Optimized treatment flow diagram 2300 shall be described with reference to FIGS. 1-5, 17-19, 20A-20D, and 21A-21D. However, optimized treatment flow diagram 2300 is not limited to those example embodiments.

In step 2302, as shown in the example of FIGS. 1 and 2, stimulation apparatus 200 of stimulation system 100 can be positioned on patient 102, where stimulation apparatus 200 includes electrode array 220, first light emitter array 232, second light emitter array 236, third light emitter array 242, acoustic emitter array 252, and/or fourth light emitter array 262.

In step 2304, as shown in the example of FIGS. 2, 2A, and 5, electrode array 220 can be scanned to determine which electrodes optimally contact patient 102. In some embodiments, optimally contacted electrodes are based on a resistance value between patient 102 and contacted electrodes and/or an amplitude of measured EEG signals from first and second electrodes 224, 228 of electrode array 220.

In step 2306, as shown in the example of FIGS. 1, 2, and 5, electrode array 220 can measure EEG signals (e.g., brain waves 110) of patient 102 with the optimally contacted electrodes of electrode array 220.

In step 2308, as shown in the example of FIGS. 1, 2, 5, and 17-19, control unit 300 of stimulation system 100 can generate a sequence of macro pulses 1702 composed of PWM filling pulses 1702a, 1702b, 1702c, etc.

In step 2310, as shown in the example of FIGS. 1, 2, 5, and 17-19, a frequency and/or a duty cycle of PWM filling pulses 1702a, 1702b, 1702c, etc. can be adjusted to reduce a heating (surface temperature) of tissues of patient 102.

In step 2312, as shown in the example of FIGS. 1, 2, 5, 17-19, 20A-20D, and 21A-21D, a spatial control (e.g., spatial waves 2000, 2100) of the adjusted PWM filling pulses (e.g., 1702a, 1702b, 1702c, etc. shown in FIG. 19) can be adjusted based on the measured EEG signals.

In step 2314, as shown in the example of FIGS. 1, 2, 5, 17-19, 20A-20D, 21A-21D, first light emitter array 232, second light emitter array 236, third light emitter array 242, acoustic emitter array 252, and/or fourth light emitter array 262 can emit radiation into the brain of patient 102 based on the spatially controlled PWM pulses (e.g., spatial waves 2000, 2100) for treatment of a neurological abnormality.

It is to be understood that the phraseology or terminology herein is for the purpose of description and not of limitation, such that the terminology or phraseology of the present specification is to be interpreted by those skilled in relevant art(s) in light of the teachings herein.

The following examples are illustrative, but not limiting, of the embodiments of this disclosure. Other suitable modifications and adaptations of the variety of conditions and parameters normally encountered in the field, and which would be apparent to those skilled in the relevant art(s), are within the spirit and scope of the disclosure.

While specific embodiments have been described above, it will be appreciated that the embodiments can be practiced otherwise than as described. The description is not intended to limit the scope of the claims.

It is to be appreciated that the Detailed Description section, and not the Summary and Abstract sections, is intended to be used to interpret the claims. The Summary and Abstract sections can set forth one or more but not all exemplary embodiments as contemplated by the inventor(s), and thus, are not intended to limit the embodiments and the appended claims in any way.

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the embodiments that others can, by applying knowledge within the skill of the art, readily modify and/or adapt for various applications such specific embodiments, without undue experimentation, without departing from the general concept of the embodiments. Therefore, such adaptations and modifications are intended to be within the meaning and range of equivalents of the disclosed embodiments, based on the teaching and guidance presented herein.

The breadth and scope of the embodiments should not be limited by any of the above-described exemplary embodiments, but should be defined only in accordance with the following claims and their equivalents.

What is claimed is:

1. A system for treatment of a neurological disorder and/or disease, the system comprising:
   a stimulation apparatus comprising:
      a sensor array comprising a plurality of sensors and configured to dynamically measure electroencephalography (EEG) signals of a patient; and
      an emitter array comprising a plurality of emitters and configured to dynamically emit radiation into the patient based on the measured EEG signals for treatment of the neurological disorder and/or disease; and
   a control unit coupled to the stimulation apparatus and configured to synchronously measure the EEG signals from the sensor array and emit radiation from the emitter array within a real time closed loop at a period of 2.56 seconds or less.

2. The system of claim 1, wherein the emitted radiation is composed of a sequence of optical macro pulses, each having a defined shape, based on the measured EEG signals.

3. The system of claim 2, wherein each optical macro pulse is composed of a sequence of pulse width modulation (PWM) filling pulses.

4. The system of claim 3, wherein the control unit adjusts a frequency and a duty cycle of the sequence of PWM filling pulses to reduce heating of the patient's tissues and to control a penetration depth of the radiation into the patient's tissues.

5. The system of claim 2, wherein each optical macro pulse has an envelope and the control unit adjusts a shape of the envelope and a time between sequential envelopes of the optical macro pulses based on the measured EEG signals.

6. The system of claim 5, wherein the shape of the envelope comprises a rectangular shape, a triangular shape, a Gaussian shape, an exponential shape, a raised cosine-based shape, or a combination thereof.

7. The system of claim 1, wherein the control unit comprises a spatial wave controller coupled to the emitter array and configured to synchronously modulate a spatial moving wave of radiation in four-dimensions within the real time closed loop.

8. The system of claim 1, wherein a sensor in the sensor array has a conical shape comprising a plurality of sub-sensors.

9. The system of claim 1, wherein the EEG signals are based on a local EEG signal obtained from a sensor in the sensor array.

10. The system of claim 1, wherein the EEG signals are based on a global synthesized EEG signal obtained from a combination of local EEG signals obtained from sensors in the sensors array.

11. The system of claim 10, wherein the global synthesized EEG signal is filtered in a pre-determined frequency range and/or by a specific signal processing algorithm.

12. The system of claim 1, wherein the control unit is configured to determine peak brain wave frequencies of the patient based on the measured EEG signals.

13. The system of claim 12, wherein the peak brain wave frequencies of the patient are determined based on a fast Fourier transform (FFT) of the measured EEG signals.

14. The system of claim 1, wherein the control unit comprises a circadian rhythm detector configured to determine an awake-sleep cycle of the patient based on the measured EEG signals.

15. The system of claim 14, wherein, in an awake configuration, the control unit adjusts the shape of the sequence of optical macro pulses based on the determined awake-sleep cycle.

16. The system of claim 14, wherein, in a sleep configuration, the control unit adjusts the shape of the sequence of optical macro pulses based on the determined awake-sleep cycle.

17. The system of claim 1, wherein the neurological disorder and/or disease comprises amyloidopathy, amyloidosis, tauopathy, Parkinson's disease, cerebral amyloid angiopathy, familial amyloid polyneuropathy, Huntington's disease, Alzheimer's disease, dementia, depression, neurological sexual function disease, trauma, tremors, insomnia, delirium, seizures, or a combination thereof.

18. The system of claim 1, wherein the stimulation apparatus comprises a headpiece affixed to the patient's head, and the EEG signals comprise transcranial EEG signals.

19. The system of claim 18, wherein the stimulation apparatus further comprises:
a second sensor array configured to dynamically measure second transcranial EEG signals of the patient; and
a second emitter array configured to dynamically emit second radiation into the patient based on the measured second transcranial EEG signals for treatment of the neurological disorder and/or disease.

20. The system of claim 19, wherein a frequency range of radiation emitted by the second emitter array is different than a frequency range of radiation emitted by the emitter array.

21. The system of claim 18, wherein the stimulation apparatus further comprises an eyepiece affixed to the patient's eye and comprising a third emitter array configured to dynamically emit warm white light radiation based on the measured transcranial EEG signals.

22. The system of claim 18, wherein the stimulation apparatus further comprises an earpiece affixed to the patient's ear and comprising an acoustic emitter array configured to dynamically emit acoustic radiation based on the measured transcranial EEG signals.

23. The system of claim 18, wherein the stimulation apparatus further comprises a nosepiece affixed to the patient's nose and comprising a fourth emitter array configured to dynamically emit fourth radiation based on the measured transcranial EEG signals.

24. The system of claim 1, further comprising a sensor coupled to the control unit and affixed to the patient, wherein the sensor comprises a tremor sensor, an accelerometer, a pulse sensor, a temperature sensor, an oxygen saturation ($SpO_2$) sensor, or a combination thereof.

25. The system of claim 1, wherein the real time closed loop is within a biological time constant of a brain state of the patient.

26. The system of claim 25, wherein the biological time constant is less than about 25 ms.

* * * * *